United States Patent
Suzuki et al.

(10) Patent No.: US 6,271,238 B1
(45) Date of Patent: Aug. 7, 2001

(54) ACETAMIDE DERIVATIVES AND PROTEASE INHIBITORS

(75) Inventors: Yoshikazu Suzuki, Tokyo; Koichi Ishida, Ibaraki, both of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/254,123

(22) PCT Filed: Sep. 5, 1997

(86) PCT No.: PCT/JP97/03132

§ 371 Date: Mar. 1, 1999

§ 102(e) Date: Mar. 1, 1999

(87) PCT Pub. No.: WO98/09949

PCT Pub. Date: Mar. 12, 1998

(30) Foreign Application Priority Data

Sep. 6, 1996 (JP) .................................................. 8-255335

(51) Int. Cl.[7] .................... A61K 31/506; A61K 31/513; A61P 11/06; C07D 239/36
(52) U.S. Cl. ............................. 514/269; 544/319
(58) Field of Search ................ 514/269; 544/319

(56) References Cited

U.S. PATENT DOCUMENTS

| | | | |
|---|---|---|---|
| 5,221,752 | 6/1993 | Someno et al. | 548/540 |
| 5,441,960 | 8/1995 | Bernstein et al. | 544/319 |
| 5,455,271 | * 10/1995 | Yuan et al. | 514/654 |
| 5,948,785 | * 9/1999 | Akahoshi et al. | 544/319 |

FOREIGN PATENT DOCUMENTS

| | | |
|---|---|---|
| 364344 | * 4/1990 | (EP) . |
| 528633 | 2/1993 | (EP) . |
| 93/21209 | 10/1993 | (WO) . |
| 93/21214 | 10/1993 | (WO) . |
| 96/33974 | 10/1996 | (WO) . |

* cited by examiner

*Primary Examiner*—Richard L. Raymond
*Assistant Examiner*—Venkataraman Balasubramanian
(74) *Attorney, Agent, or Firm*—Nields & Lemack

(57) ABSTRACT

The present invention relates to novel acetamide compounds having a substituted heterocyclic group and consecutive dicarbonyl structures, for example, 1-pyrimidinylacetamide compounds, and these compounds have inhibitory activity on chymotrypsin type proteases and are useful as inhibitors for said enzymes, particularly as chymase inhibitors. The novel acetamide compounds of the present invention are shown in formula (I) below:

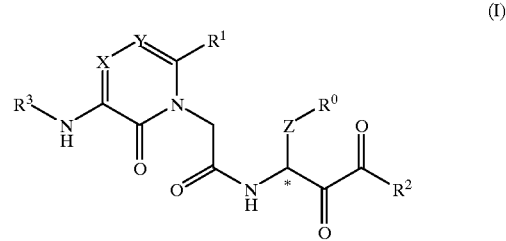

(I)

wherein $R^0$ is substituted or unsubstituted phenyl; $R^1$ is aryl or heteroaryl which may be substituted or unsubstituted; $R^2$ is substituted or unsubstituted alkyl, arylalkyl, or heteroarylalkyl; $R^3$ is hydrogen; acyl group; sulfonyl group; isocyanate group; thiourea; a lower alkyl or a substituted lower alkyl; aryl (1–7C) alkyl, heteroaryl (1–7C) alkyl, aryl and heteroaryl; X represents a carbon atom and Y represents a nitrogen atom; and Z is a polymethylene group wherein a hydrogen atom in the polymethylene may be replaced.

21 Claims, No Drawings

ACETAMIDE DERIVATIVES AND PROTEASE INHIBITORS

TECHNICAL FIELD

The present invention relates to novel acetamide derivatives having a substituted heterocyclic group and consecutive dicarbonyl structures, for example 1-pyrimidinylacetamide compounds, 4-pyrazinylacetamide compounds, 4-triazinylacetamide compounds etc., and relates to inhibitors for chymotrypsin type proteases, particularly chymase inhibitors. The present compounds are useful as a preventive or therapeutic agent for diseases in which chymotrypsin type proteases are considered to, generally participate. For example, chymotrypsin type proteases are considered to participate directly or indirectly in diseases such as asthma, allergy, inflammations, rheumatism, hypertension, heart failure, myocardial infarction, cardiac hypertrophy, vascular injuries accompanied by angiogenesis and atheroma, nephritis and renal insufficiency etc. The present invention encompasses intermediates useful for synthesis of heterocyclic amide compounds having consecutive dicarbonyl structures, a process, for producing the heterocyclic amide compounds, and a pharmaceutical composition containing such heterocyclic amide compounds as the active ingredient, and a method of using the same.

BACKGROUND OF THE INVENTION

It is known that chymase belongs to chymotrypsin type proteases in serine proteases and is a cytotoxic protein accumulated in secretory granules in mast cells and released upon stimulation. Further, it is recently reported in Circ. Res., 66, 883 (1994) that chymase possesses the action of converting angiotensin I into angiotensin II involved in blood pressure regulation in vivo. Further, it is also known that a chymase inhibitor inhibits release of histamine from mast cells (J. Cell. Biochem., 38, 291 (1988)) and release of a cytotoxic protein from eosinophils (Arch. Biochem. Biophys., 312, 67, (1994)). That is, it is known generally at present that chymase is involved not only in cytotoxicity but also in release of various mediators in vivo.

Further, the action of chymase varies depending on the type of animal, and it is reported that there is a great difference in the action particularly between human or dog and rodent (Proc. Natl. Acad. Sci. USA, 84, 364 (1987)).

As a compound inhibiting chymase, only an inhibitor for chymotrypsin as a digestive enzyme is known at present and is not satisfactory in inhibitory activity, selectivity of inhibition toward other proteases, stability of the compound in vivo, toxicity etc. and it has not been developed as a pharmaceutical composition. Accordingly, there is demand for a highly safe chymase inhibitor which at low concentration, selectively inhibits chymase.

DISCLOSURE OF THE INVENTION

Under these circumstances, the present inventors made extensive studies to find chymase inhibitors in order to solve the above problems, and as a result, they arrived at the present invention.

That is, the present invention relates to the following items (1) to (30):

(1) Novel acetamide derivatives represented by the following chemical formula (I) or pharmacologically acceptable salts thereof.

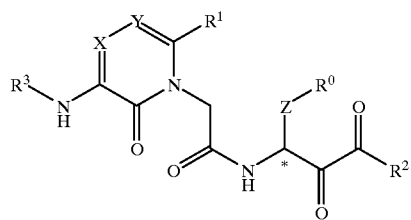

(I)

wherein $R^0$ is a phenyl group whose ring may have one or more substituent groups selected from group A defined below (group A; group A represents halogen, nitro, a hydroxyl group, a lower alkoxy group, a lower alkyl group, or a halogen-substituted lower alkyl group);

$R^1$ is (i) aryl, (ii) heteroaryl or (iii) $C_{1-6}$, straight-chain, branched or cyclic alkyl group, which may independently have one or more substituent groups defined with respect to group A; or $R^1$ may independently have one or more substituent groups selected from group B consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$ and $P(O) (OR_a)_2$ on the above groups (i) to (iii) (among which $R_a$ to $R_c$ are independently hydrogen, lower alkyl or substituted lower alkyl; or $R_a$ to $R_c$ are independently aryl (1–7C) alkyl, heteroaryl (1–7C) alkyl, aryl and heteroaryl, among which the aryl or heteroaryl ring may have one or more, usually 1 to 3, substituent groups selected from the above-defined group A. The substituted lower alkyl has 1 to 3 atoms or groups selected from halogen, nitro and hydroxyl group as substituent group); or $R^1$ may have the following defined one or more of cyclic group G as a substituent group on the above groups (i) to (iii) (cyclic group G; cyclic group G represents a heterocyclic group consisting of a 5- or 6-membered ring containing 1 to 3 oxygen or nitrogen atoms and may have a substituent group);

$R^2$ represents (1–8C) alkyl, aryl (1–7C) alkyl, heteroaryl (1–7C) alkyl, and aryl; or $R^2$ represents the above-defined group B or (1–8C) alkyl having group B as a substituent group; or (1–8C) alkyl having the above-defined cyclic group G as a substituent group;

$R^3$ is hydrogen; or $R^3$ is (i) $D(CH_2)_{0-3}.CO$, (ii) D.CO.E.CO or (iii) $D.SO_2.E.CO$ as an acyl group; or $R^3$ is $D(CH_2)_{0-3}.SO_2$ or $D.COE.SO_2$ as a sulfonyl group (wherein group D represents hydrogen, a 1–6C straight-chain, branched or cyclic alkyl group, aryl group, halogeno lower alkyl, halogeno lower alkoxy, amino, lower alkoxyamino, halogeno lower alkylamino, $R_bR_cN$, $R_bR_cN.O$, $R_aO$, $R_a$, $R_aOCO$, $R_bR_cNCO$, $R_aSO_2NR_b$, $R_bS$ and the above-defined group G; and group E represents a divalent crosslinking group containing 1 to 6 carbon atoms); or $R^3$ is an urea group represented by group $R_bR_cNCO$; or $R^3$ is thiourea represented by $R_bR_cN.CS$; or $R^3$ is $R_a$;

X and Y independently represent a nitrogen atom or a carbon atom and may be substituted by groups represented by $R_a$ to $R_c$; and Z represents a polymethylene group wherein hydrogen atoms on the polymethylene group may independently be replaced by $R_a$ and $R_b$.

(2) Novel acetamide derivatives according to the above item (1) or pharmacologically acceptable salts thereof, wherein $R^2$ in formula (I) represents the followings:

$R^2$ is a (1–8C) alkyl, aryl (1–7C) alkyl, heteroaryl (1–7C) alkyl and aryl; or $R^2$ is the above-defined group B (provided that when Y is a nitrogen atom and X is a carbon atom in formula (I), $R^2$ represents groups other than $OR_a$ or $NR_bR_c$), or (1–8C) alkyl having the group B as a substituent group; or (1–8C) alkyl having the above-defined cyclic group G as a substituent group.

(3) Novel acetamide derivatives according to the above item (1) or (2) or pharmacologically acceptable salts thereof, wherein the cyclic group G represents a group selected from the group consisting of pyridyloxy, 2-oxo-1,2-dihydropyridine-1-yl, pyrimidyloxy, pyrazyloxy, pyridazyloxy, piperazine-1-yl optionally having a lower alkyl or aryl lower alkyl group at the 4-position, pyrrolidine-1-yl, piperidine-1-yl, 4-morpholine-4-yl, and pyrrole-1-yl.

(4) Novel acetamide derivatives according to the above item (1) or pharmacologically acceptable salts thereof, wherein the respective symbol in formula (I) represents the followings:

$R^0$ is a phenyl group whose ring may have 1 to 5 substituent groups selected from group A consisting of halogen, a hydroxyl group, a lower alkoxy group, a lower alkyl group, and a trifluoromethyl group;

$R^1$ is phenyl, thienyl, furyl, pyridyl, pyrrolyl or a C1–6 straight-chain, branched or cyclic alkyl group which may independently have one or more substituent groups defined above for group A; or $R^1$ may have one or more substituent groups selected from group B consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$, and $P(O)(OR_a)_2$ on the above phenyl, thienyl, furyl, pyridyl, pyrrolyl or C1–6 straight-chain, branched or cyclic alkyl group (among which $R_a$ to $R_c$ are independently hydrogen and lower alkyl; or $R_a$ to $R_c$ are independently aryl (1–7C) alkyl, heteroaryl (1–7C) alkyl, aryl and heteroaryl, wherein the aryl or heteroaryl ring may have one or more substituent groups selected from group A); or $R^1$ may have one or more of cyclic group G selected from the group consisting of pyridyloxy, 2-oxo-1,2-dihydropyridine-1-yl, pyrimidyloxy, pyrazyloxy, pyridazyloxy, piperazine-1-yl optionally having a lower alkyl or aryl lower alkyl group at the 4-position, pyrrolidine-1-yl, piperidine-1-yl, 4-morpholine-4-yl, and pyrrole-1-yl as a substituent group on the above phenyl, thienyl, furyl, pyridyl, pyrrolyl or C1–6 straight-chain, branched or cyclic alkyl group;

$R^2$ represents (1–4C) alkyl, aryl (1–3C) alkyl, heteroaryl (1–3C) alkyl, and aryl; or $R^2$ represents the above-defined group B or (1–3C) alkyl having group B as a substituent group; or (1–3C) alkyl having the above-defined cyclic group G as a substituent group;

$R^3$ is hydrogen; or $R^3$ is (i) $D(CH_2)_{0-3}.CO$, (ii) $D.CO.E.CO$ or (iii) $D.SO_2.E.CO$ as an acyl group; or $R^3$ is $D(CH_2)_{0-3}.SO_2$ and $D.CO.E.SO_2$ as a sulfonyl group; or $R^3$ is thiourea represented by $R_bR_cN.CS$; or $R^3$ is $R_a$ (wherein group D represents hydrogen, a 1–6C straight-chain, branched or cyclic alkyl group, trifluoromethyl, 2,2,2-trifluoroethoxy, amino, methoxyamino, 2,2,2-trifluoroethylamino, $R_bR_cN$, $R_bR_cN.O$, $R_aO$, $R_a$, $R_aOCO$, $R_bR_aNCO$, $R_aSO_2NE$, $R_aS$ or the above-defined group G. Group E represents a divalent benzene nucleus., a divalent heteroaryl nucleus, 1,4-piperazine-di-yl, and a C1–6 straight-chain, branched or cyclic divalent aliphatic crosslinking group);

X and Y independently represent a nitrogen atom or a carbon atom and may be substituted with the groups represented by $R_a$ to $R_c$; and Z represents —$CH_2$— wherein the 2 hydrogen atoms may independently be replaced by $R_a$ and $R_b$.

(5) Novel acetamide derivatives according to the above items (1) to (4) or pharmacologically acceptable salts thereof, wherein the following respective symbol in formula (I) represents the followings:

$R^0$ is a phenyl group which may have 1 to 3 substituent groups selected from halogen, a hydroxyl group, a lower alkoxy group, a lower alkyl group, and a trifluoromethyl group as group A on the ring;

$R^1$ is a phenyl group which may independently have one or more of the above-defined group A on the ring; or $R^1$ may have one or more substituent groups selected from group B consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$ and $P(O)(OR_a)_2$;

$R^2$ represents (1–4C) alkyl, aryl (1–3C) alkyl, heteroaryl (1–3C) alkyl, and aryl; or $R^2$ represents the above-defined group B or (1–3C) alkyl having group B as a substituent group; or (1–3C) alkyl having the following defined cyclic group G as a substituent group. Here, group G represents cyclic group G selected from the group consisting of pyridyloxy, 2-oxo-1,2-dihydropyridine-1-yl, pyrimidyloxy, pyrazyloxy, pyridazyloxy, piperazine-1-yl optionally having a lower alkyl group or an aryl (1–7C) alkyl group at the 4-position, pyrrolidine-1-yl, piperidine-1-yl, 4-morpholine-4-yl, and pyrrole-1-yl;

$R^3$ is hydrogen; or $R^3$ is (i) $D(CH_2)_{0-3}.CO$, (ii) $D.CO.E.CO$ or (iii) $D.SO_2.E.CO$ as an acyl group, or $D.(CH_2)_{0-3}.SO_2$ and $D.CO.E.SO_2$ as a sulfonyl group (wherein group D represents hydrogen, a 1–6C straight-chain, branched or cyclic alkyl group, trifluoromethyl, 2,2,2-trifluoroethoxy, 2,2,2-trifluoroethylamino, $COOR_a$, $CONR_bR_c$, $NR_bR_c$, or group G defined above); or $R^3$ is thiourea represented by $R_bR_cN.CS$; or group E independently represents a divalent benzene nucleus, a divalent heteroaryl nucleus, 1,4-piperazine-di-yl, a divalent cyclohexyl group, and a divalent 1,4-cyclohexadienyl group); or $R^3$ is $R_a$;

X and Y independently represent a nitrogen atom or an unsubstituted carbon atom; and Z represents —$CH_2$— wherein the 2 hydrogen atoms may independently be replaced by $R_a$ and $R_b$.

(6) Novel acetamide derivatives according to the above items (1) to (5) or pharmacologically acceptable salts thereof, wherein the following respective symbol in formula (I) represents the followings:

$R^0$ is an unsubstituted phenyl group or a substituted phenyl group with 1 or 2 substituent groups selected from halogen, lower alkyl, hydroxy, lower alkoxy, and lower acyloxy, $R^1$ is an unsubstituted phenyl group, $R^2$ is an unsubstituted phenyl group, an unsubstituted (1–8C) alkyl, or a substituted (1–8C) alkyl group having a substituent group selected from carboxyl, lower acyloxy, phenyl, pyrrolidine-1-yl, pyridyl, pyridyloxy, 2-oxo-1,2-dihydropyridine-1-yl, pyrimidyloxy, pyrazyloxy, pyridazyloxy, or a lower alkyl-substituted piperazine-1-yl or a lower alkyl-substituted piperazine-1-yl-carbonyl, and morpholino, $R^3$ is hydrogen, a lower acyl group, formyl, sulfamoyl, lower alkylsulfonyl, aryl lower alkylsulfonyl, heteroarylsulfonyl, trifluoromethylsulfonyl or tetrahydrofuroyl, X is an unsubstituted carbon atom, Y is a nitrogen atom, and Z is —$CH_2$—.

(7) Novel acetamide derivatives according to the above items (1) to (6) or pharmacologically acceptable salts thereof, wherein the following respective symbol in formula (I) represents the followings:

$R^0$ is an unsubstituted phenyl group, $R^1$ is an unsubstituted phenyl group, $R^2$ is an unsubstituted (1–8C) alkyl or a (1–8C) alkyl group having a substituent group selected from pyrrolidine-1-yl, pyridyloxy, 2-oxo-1,2-dihydropyridine-1-yl, pyrimidyloxy, pyrazyloxy, pyridazyloxy, lower alkyl-substituted piperazine-1-yl or a lower alkyl-substituted piperazine-1-yl carbonyl, X is an unsubstituted carbon atom, Y is a nitrogen atom, and Z is —$CH_2$—.

(8) Novel acetamide derivatives according to the above items (1) to (7) or pharmacologically acceptable salts thereof, wherein $R^3$ in formula (I) is a group selected from hydrogen, lower alkylcarbonyl, lower alkoxycarbonyl, acyl, sulfonyl and sulfamoyl.

(9) Novel acetamide derivatives according to the above item (1) or pharmacologically acceptable salts thereof, wherein the following respective symbol in formula (I) represents the followings:

$R^0$ is an unsubstituted phenyl group or a lower alkoxy-substituted phenyl group, $R^1$ is an unsubstituted phenyl group, $R^2$ is a lower alkoxy, $R^3$ is hydrogen or a lower alkoxycarbonyl, X is an unsubstituted carbon atom, Y is a nitrogen atom, and Z is —$CH_2$—.

(10) Novel acetamide derivatives or pharmacologically acceptable salts thereof, wherein the following respective symbol in formula (I) represents the followings:

$R^0$ is an unsubstituted phenyl group, $R^1$ is an unsubstituted phenyl group, $R^2$ is 3-(2-oxo-1,2-dihydropyridine-1-yl)propyl, $R^3$ is a group selected from hydrogen, t-butyloxycarbonyl, formyl, acetyl, lower alkylsulfonyl, aryl lower alkylsulfonyl, heteroarylsulfonyl, trifluoromethylsulfonyl, lower alkylaminosulfonyl, aryl lower alkylaminosulfonyl, heteroaryl lower alkylaminosulfonyl, and heteroarylaminosulfonyl, X is an unsubstituted carbon atom, Y is a nitrogen atom, and Z is —$CH_2$—.

(11) Novel acetamide derivatives or pharmacologically acceptable salts thereof, wherein the following respective symbol in formula (I) represents the followings:

$R^0$ is an unsubstituted phenyl group, $R^1$ is an unsubstituted phenyl group, $R^2$ is 3-(2-pyridyloxy)propyl, $R^3$ is a group selected from hydrogen, t-butyloxycarbonyl, formyl, acetyl, lower alkylsulfonyl, aryl lower alkylsulfonyl, heteroarylsulfonyl, trifluoromethylsulfonyl, lower alkylaminosulfonyl, aryl lower alkylaminosulfonyl, heteroaryl lower alkylaminosulfonyl, and heteroarylaminosulfonyl, X is an unsubstituted carbon atom, Y is a nitrogen atom, and Z is —$CH_2$—.

(12) 2-(5-Amino-6-oxo-2-phenyl-1,6-dihydropyrimidine-1-yl)-N-{2,3-dioxo-1-(3-fluorophenyl) methyl}butyl-acetamide or pharmacologically acceptable salts thereof.

(13) 2-(5-Amino-6-oxo-2-phenyl-1,6-dihydropyrimidine-1-yl)-N-{2,3-dioxo-6-(4-morpholine-4-yl)-1-phenylmethyl}-hexylacetamide or pharmacologically acceptable salts thereof.

(14) 2-(5-Amino or t-butyloxycarbonylamino or acetylamino-6-oxo-2-phenyl-1,6-dihydropyrimidine-1-yl)-N-{2,3-dioxo-1-phenylmethyl-6-(2-oxo-1,2-dihydropyridine-1-yl)}hexyl-acetamide or pharmacologically acceptable salts thereof.

(15) 2-(5-Amino or t-butyloxycarbonylamino or benzylsulfonyl amino or formylamino or benzylaminosulfonylamino or 4-pyridylmethyloxycarbonylamino or acetylamino-6-oxo-2-phenyl-1,6-dihydropyrimidine-1-yl )-N-{2,3-dioxo-6 (2-pyridyloxy)-1-phenylmethyl}hexylacetamide or pharmacologically acceptable salts thereof.

(16) (A) 2-(5-t-Butyloxycarbonylamino-6-oxo-2-phenyl-1,6-dihydropyrimidine) -1-yl)-N-{2-methoxycarbonyl-1-(4-hydroxyphenyl)methyl-2-oxo}ethylacetamide, (B) 2-(5-t-butyloxycarbonylamino-6-oxo-2-phenyl-1,6-dihydropyrimidine-1-yl)-N-{2-methoxycarbonyl-1-(3-fluoro-4-hydroxyphenyl)methyl-2-oxo}ethylacetamide, (C) 2-(5-amino-6-oxo-2-phenyl-1,6-dihydropyrimidine-1-yl)-N-(2-oxo2-phenylcarbamoyl-1-phenylmethyl) ethylacetamide, (D) 2-(5-amino-6-oxo-2-phenyl-1,6-dihydropyrimidine-1-yl)-N-(2-benzylcarbamoyl-2-oxo-1-phenylmethyl)ethylacetamide, (E) 2-(5-amino-6-oxo-2-phenyl-1,6-dihydropyrimidine-1-yl)-N-(2-oxo-2-phenylethylcarbamoyl-1-phenylmethyl) ethyl-acetamide, (F) 2-(5-t -butyloxycarbonylamino-6-oxo2-phenyl-1,6-dihydropyrimidine-1-yl)-N-{2-methoxycarbonyl-1-(4-methyloxyphenyl)methyl-2-oxo}ethylacetamide, (G) 2-(5-t-butyloxycarbonylamino-6-oxo-2-phenyl-1,6-dihydropyrimidine-1-yl)-N-(2-oxo-2-phenylethylcarbamoyl-1-phenylmethyl)ethylacetamide, (H) 2-(5-6-oxo-2-phenyl-1,6-dihydropyrimidine-1-yl)-N-{2-methoxycarbonyl-1-(4-methyloxyphenyl)methyl-2-oxo}ethyl acetamide, or pharmacologically acceptable salts thereof.

(17) (A) 2-(5-Amino-6-oxo-2-phenyl-1,6-dihydropyrimidine-1-yl)-N-(2,3-dioxo-1-phenylmethyl)butylacetamide, (B) 2-(5-amino-6-oxo-2-phenyl-1,6-dihydropyrimidine-1-yl)-N-(2,3-dioxo-6-phenyl-1-phenylmethyl)hexylacetamide, (C) 2-(5amino-6-oxo-2-phenyl-1,6-dihydropyrimidine-1-yl)-N-(2,3-dioxo-5-phenyl-1-phenylmethyl)pentylacetamide, (D) 2-(5-amino-6-oxo-2-phenyl-1,6-dihydropyrimidine-1-yl)-N-(2,3dioxo-1-phenylmethyl)heptylacetamide, (E) 2-(5-amino-6-oxo-2-phenyl-1,6-dihydropyrimidine-1-yl)-N-(2,3-dioxo-3-phenyl-1-phenylmethyl)propylacetamide, (F) 2-(5-amino-6-oxo-2-phenyl-1,6-dihydropyrimidine-1-yl)-N-(6-carboxyl-2,3-dioxo-1-phenylmethyl)hexylacetamide, (G) 2-(5-amino-6-oxo-2-phenyl-1,6-dihydropyrimidine-1-yl)-N-{2,3-dioxo-1-(3-fluoro-4-hydroxyphenyl)methyl}butylacetamide, (H) 2-(5-amino-6-oxo-2-phenyl-1,6-dihydropyrimidine-1-yl)-N-{2,3-dioxo-1-(3-fluorophenyl)methyl}butylacetamide, (I) 2-(5-amino-6-oxo-2-phenyl-1,6-dihydropyrimidine-1-yl)-N-{2,3-dioxo-1-(3-chlorophenyl)methyl}butylacetamide, (J) 2-(5-amino-6-oxo-2-phenyl-1,6-dihydropyrimidine-1-yl)-N-{2,3-dioxo-1-(3-methylphenyl)methyl}butylacetamide, (K) 2-(5-amino-6-oxo-2-phenyl-1,6-dihydropyrimidine-1-yl)-N-{2,3-dioxo-1-(4-fluorophenyl)methyl}butylacetamide, (L) 2-(5-amino-6-oxo-2-phenyl-1,6-dihydropyrimidine-1-yl)-N-{2,3-dioxo-1-(4-chlorophenyl)methyl}butylacetamide, (M) 2-(5-amino-6-oxo-2-phenyl-1,6 -dihydropyrimidine-1-yl)-N-{2,3-dioxo-6-ethoxycarbonyl-1-(3-fluorophenyl) methyl}hexylacetamide, (N) 2-(5-amino-6-oxo-2-phenyl-1,6-dihydropyrimidine-1-yl)-N-{1-(3-fluorophenyl)methyl-7-(4-methylpiperazine-1-yl)-2,3,7-trioxo}heptylacetamide, (O) 2-(5-amino-6-oxo-2-phenyl-1,6-dihydropyrimidine-1-yl)-N-{2,3-dioxo-6-(4-morpholine-4-yl)-1-phenylmethyl}hexylacetamide, (P) 2-(5-amino-6-oxo-2-phenyl-1,6-dihydropyrimidine-1-yl)-N-{2,3-dioxo-6-(2-oxo-1,2dihydropyridine-1-1yl)-1phenyl-methyl}hexylacetamide, (Q) 2-(5-amino-6-oxo-2-phenyl-1,6-dihydropyrimidine-1-yl)-N-{2,3-dioxo-1-phenylmethyl-6-(2-pyridyloxy)}hexylacetamide, (R) 2-(2-amino-3-oxo-5-phenyl-3,4-dihydropyrazine-4-yl)-N-(2-methoxycarbonyl-2-oxo-1-phenylmethyl)ethylacetamide, (S) 2-(6-amino-5-oxo-3phenyl-4,5-dihydro-1,2,4triazin-4yl)-N-(2-methoxycarbonyl-2-oxo-1-phenylmethyl)ethylacetamide, (T) 2-(5-t-butyloxycarbonylamino-6-oxo-2-phenyl-1,6-dihydropyrimidine-1-yl)-N-(2,3-dioxo-1-phenylmethyl)butylacetamide, (U) 2-(5-t-butyloxycarbonylamino-6-oxo-2-phenyl-1,6-dihydropyrimidine-1-yl)-N-(2,3-di-oxo-1-phenylmethyl)hexylacetamide, (V) 2-(5-t-butyloxycarbonylamino-6-oxo-2-phenyl-1,6-dihydropyrimidine-1-yl)-N-(2,3-dioxo-1-phenylmethyl)heptylacetamide, (W) 2-{5-(3-tetrahydrofuroylamino)-6-oxo-2-phenyl-1,6-dihydropyrimidine-1-yl}-N-(2,3-dioxo-6-phenyl-1-phenylmethyl)-hexylacetamide, (X) 2-(5-amino-6-oxo-2-phenyl-1,6-dihydropyrimidine- 1-yl)-N-{2,3-dioxo-1-(2-fluorophenyl) methyl}butylacetamide, or pharmacologically acceptable salts thereof.

(18) Salts of novel acetamide derivatives according to the above item (1), wherein the pharmacologically acceptable salts are selected from (A) alkali metal salts, alkaline earth metal salts, aluminum salts, ammonium salts or salts obtained from organic bases forming pharmaceutically acceptable cations when the novel acetamide derivatives of formula (I) are acidic compounds and (B) acid-added salts formed by using an acid forming pharmaceutically acceptable anions when the novel acetamide derivatives of formula (I) are basic compounds.

(19) A pharmaceutical composition comprising the novel acetamide derivative of the above items (1) to (18) or pharmacologically acceptable salt thereof as an active ingredient.

(20) A novel protease inhibitor comprising the novel acetamide derivative of the above items (1) to (19) or pharmacologically acceptable salt thereof as an active ingredient.

(21) A novel chymase inhibitor comprising the novel acetamide derivative of the above items (1) to (20) or pharmacologically acceptable salt thereof as an active ingredient.

(22) A novel mast cell degranulation inhibitor or a mast cell histamine release inhibitor comprising the novel acetamide derivative of the above items (1) to (18) or pharmacologically acceptable salt thereof as an active ingredient.

(23) A novel eosinophil activation inhibitor or an eosinophil active oxygen release inhibitor comprising the novel acetamide derivative of the above items (1) to (18) or pharmacologically acceptable salt thereof as an active ingredient.

(24) A process for producing the novel acetamide derivatives of the above items (1) to (18) or pharmacologically acceptable salts thereof, which comprises the following step (A) or (B):

(A) in synthesis of the novel acetamide derivatives of formula (I), the step of oxidizing the alcohol of formula (II):

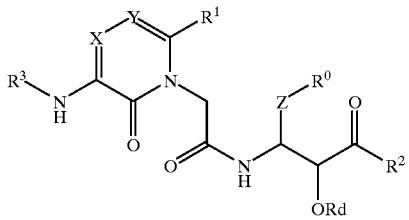

(II)

after removal of an alcohol protective group if present, to convert it into the novel acetamide derivative of formula (I) wherein $R_d$ is hydrogen or a protective group for a hydroxyl group, or (B) the step of condensation between the compound of formula (III) or the compound of formula (IV) wherein $R^{3'}$ is hydrogen:

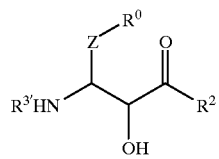

(III)

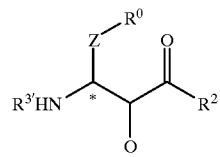

(IV)

wherein $R^3$ in formula (III) or (IV) has the same meaning as $R^{3'}$ defined in the above item (1), and the compound of formula (V):

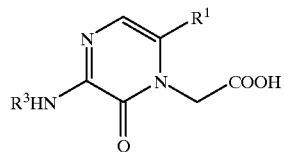

(V)

or the compound of formula (VI):

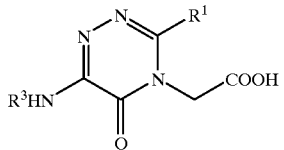

(VI)

(In the formulas mentioned above, $R^0$, $R^1$, $R^2$, X, Y and Z have the same meaning as defined in the above item (1).)

(25) Compounds of formula (II) according to the above item (24) and salts thereof, wherein $R^0$, $R^1$, $R^2$, $R^3$, X, Y and Z are the groups defined in the above item (1).

(26) Compounds of formula (III) according to the above item (24) and salts thereof, wherein $R^0$, $R^2$, and Z are the groups defined in the above item (1), and $R^{3'}$ is the group defined in the above item (24).

(27) Compounds of formula (IV) according to the above item (24) and salts thereof, wherein $R^0$, $R^2$ and Z are the groups defined in the above item (1), and $R^{3'}$ is the group defined in the above item (24).

(28) Compounds of formula (V) according to the above item (24) and salts thereof, wherein $R^1$, $R^3$, X and Y are the groups defined in the above item (1).

(29) Compounds of formula (VI) according to the above item (24) and salts thereof, wherein $R^1$ and $R^3$ are the groups defined in the above item (1).

(30). 3-$R^{3'}$-5-($R_2$CO)-2,2-di-lower alkyl-4-($R^0$-Z) oxazolidine i.e. a ketone derivative of oxazolidine or salts thereof wherein $R^0$, $R^2$ and Z are the groups defined in claim 1, and $R^{3'}$ has the same meaning as $R^3$ defined in claim 1.

BEST MODE FOR CARRYING OUT THE INVENTION

The present invention relates to novel acetamide derivatives having a substituted heterocyclic group and consecutive dicarbonyl structures, for example 1-pyrimidinylacetamide compounds, 1-pyrazinylacetamide compounds, and 4-triazinylacetamide compounds etc., and protease inhibitors comprising these compounds or salts thereof (referred to hereinafter as the present compounds) as an active ingredient possess an inhibitory action on the leukocyte activation of mast cell, eosinophils etc. as well as an inhibitory action on production of angiotensin II, and for example, they are expected as an agent for treating or preventing diseases such as asthma, allergy, inflammations, rheumatism, hypertension, heart failure, myocardial infarction, cardiac hypertrophy, vascular injuries accompanied by angiogenesis and atheroma, nephritis and renal insufficiency.

In the present specification, the following definitions are used unless otherwise specified.

Group A represents a group selected from the group consisting of halogen, hydroxyl group, a lower alkoxy group, a lower alkyl group and a halogen-substituted lower alkyl group.

Group B represents a group selected from the group consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$ and $P(O)(OR_a)_2$.

$R_a$ to $R_c$ independently represent a group selected from hydrogen, lower alkyl, aryl (1–7C) alkyl, heteroaryl (1–7C) alkyl, aryl and heteroaryl, among which the aryl or heteroaryl ring may have one or more substituent groups selected from the group A defined above.

Cyclic group G represents a heterocyclic group consisting of a 5-or 6-membered ring containing 1 to 3 oxygen or nitrogen atoms and may have a substituent group.

Group D represents hydrogen, a 1–6C straight-chain, branched or cyclic alkyl group, halogeno lower alkyl such as trifluoromethyl etc., halogeno lower alkoxy such as 2,2,2-trifluoroethoxy etc., lower alkoxyamino such as methoxyamino etc., halogeno lower alkylamino such as 2,2,2-trifluoroethylamino etc. , $R_bR_cN$, $R_bR_cN.O$, $R_aO$, $R_a$, $R_aOCO$, $R_bR_cNCO$, $R_aSO_2NR_b$, $R_aS$ and the above-defined group G.

Group E represents a divalent crosslinked group containing 1 to 6 carbon atoms and may contain 1 to 3 heteroatoms selected from oxygen, nitrogen and sulfur, for example a divalent benzene nucleus such as phenylene, a divalent heteroaryl nucleus such as heteroarylene, 1,4-piperazine-di-yl, and a divalent C1–6 straight-chain or branched aliphatic crosslinking group such as methylene, dimethylene, trimethylene, 2-methyltrimethylene group or an alicyclic crosslinking group such as cyclohexylene, 1,4-cyclohexadienylene etc.

Halogen means fluorine, chlorine, bromine and iodine.

The alkyl chain in the alkyl and alkoxy is a straight-chain, branched or cyclic alkyl, and the number of carbon atoms therein is preferably 1 to 20.

The lower alkyl and lower alkoxy are branched or straight-chain groups each containing I to 6 carbon atoms. The lower acyloxy is the one in which the number of carbon atoms in the alkyl chain attached to the carbonyl group is 1 to about 6. The aryl represents a phenyl group or, carbon rings and heterocarbon rings formed of 9 to 10 ring-constitutional atoms, at least one ring of them which are fused at the ortho-position is an aromatic ring. The heteroaryl contains 2 to 4 heteroatoms selected from the group consisting of carbon, oxygen, nitrogen and sulfur and represents a monocyclic he aromatic ring formed of 5 to 6 ring-constitutional atoms or a heterobicyclic ring formed of about 8 to 10 ring-constitutional atoms in a ring fused at the ortho-position.

By the carbon atom substituted asymmetrically at the position of the chiral center indicated by "*" in formula I, the compound of formula (I) is present as a single optical isomer or a racemate. If the compound of formula (I) possesses an additional one chiral element, the compound of formula (I) is present as a single diastereomer or a mixture of diastereomers. There is the possibility that any of these compounds can be isolated. The compounds of formula (I) in the present invention include those ranging from an individual diastereomer to a mixture of diastereomers and further the compounds of formula (I) include those ranging from an individual enantiomer to a mixture of enantiomers.

As can be understood by those skilled in the art, the consecutive dicarbonyl structures in formula (I) can be present as a solvate, particularly a hydrate. Accordingly, a solvate of the compound of formula (I) is included in the present invention.

The compound of formula (I) can indicate a variety of polymorphism such as solvate tautomer, in addition to the above-described solvate. Accordingly, the present invention encompasses any compounds having inhibitory action on chymotrypsin-like enzyme regardless of whether they are in any form of polymorphism such as racemate, optical isomer or solvate.

In the following items, the groups are specifically illustrated but these are shown for mere illustrative purposes and are not intended to be restrictive.

Preferable examples of group A are fluorine, chlorine, bromine, nitro, a hydroxyl group, methyl, ethyl and methoxy.

Examples of $R_a$, $R_b$ or $R_c$ are hydrogen and a lower alkyl such as methyl, ethyl, propyl, butyl, isopropyl etc., aryl (1–7C) alkyl such as benzyl, phenethyl, phenylpropyl etc., heteroaryl (1–7C) alkyl such as pyridylmethyl, pyridylethyl, pyridylpropyl, furylmethyl, furylethyl, furylpropyl etc.y aryl such as phenyl, halogen-substituted phenyl etc., and heteroaryl such as pyridyl, pyrimidyl, furyl and thienyl.

Examples of $OR_a$ in group B or group D etc. are hydroxy, methoxy, ethoxy, propyloxy, isopropyloxy, butoxy, benzyloxy, pyridylmethyloxy, phenoxy, pyridyloxy, pyrrolidinoxy etc.

Examples of $COOR_a$ in group B or group D etc. are methoxycarbonyl, ethoxycarbonyl, propyloxycarbonyl, isopropyloxycarbonyl, butoxycarbonyl, benzyloxycarbonyl, pyridylmethyloxycarbonyl, phenoxycarbonyl etc.

Examples of $CONR_bR_c$ in group B or group D etc. are dimethylaminocarbonyl, methylethylaminocarbonyl, diethylaminocarbonyl, dipropylaminocarbonyl etc.

Examples of $NR_bR_c$ in group B or group D etc. are monomethylamino, dimethylamino, methylethylamino, diethylamino, dipropylamino etc.

Examples of $NR_bCHO$ in group B etc. are formylamino, formylmethylamino etc. Examples of $NR_bCOR_a$ in group B etc. are methylcarbonylamino, ethylcarbonylamino, propylcarbonylamino, methylcarbonylmethylamino etc. Examples of $SO_2OR_a$ in group B etc. are sulfonic acid group etc. Examples of $SO_2R_a$ in group B etc. are methylsulfonyl, ethylsulfonyl, propylsulfonyl, butylsulfonyl, t-butylsulfonyl, benzylsulfonyl, toluenesulfonyl, benzenesulfonyl, formaminobenzenesulfonyl, nitrobenzenesulfonyl, methoxybenzenesulfonyl, pyridylsulfonyl, pyridylmethylsulfonyl, trifluoromethylsulfonyl etc.

Examples of $CONR_bSO_2R_a$ in group B etc. are methylsulfonylaminocarbonyl, phenylsulfonylaminocarbonyl, phenylmethylaminosulfonylcarbonyl etc. Examples of $P(O)(OR_a)_2$ in group B etc. are diethylphosphono, diphenylphosphono, dibenzylphosphono etc. Preferable examples of group B are methoxy, ethoxy, propyloxy, isopropyloxy, phenylmethyloxy, phenethyloxy, phenylpropyloxy, pyridylmethyloxy, pyridylethyloxy, pyridylpropyloxy, furylmethyloxy, furylethyloxy, furylpropyloxy, pyridyloxyethyloxy, and pyridyloxypropyloxy.

Examples of group G are 5- to 6-membered ring heteroaryl or hetero-atom-containing alicyclic groups of 5- to 6-membered ring, and preferable groups are 4-morpholine-4-yl, 4-methylpiperazine-1-yl, pyrrolidine-1-yl, piperidine-1-yl and 2-oxo-1,2-dihydropyridine-1-yl, and 2-pyridyloxy.

Preferable examples of group D are hydrogen, methyl, cyclohexyl, phenyl, pyridyl, trifluoromethyl, 2,2,2-trifluoroethyloxy, methyloxyamino, 2,2,2-trifluoroethylamino, phenylmethylamino etc.

$D.(CH_2)_{0-3}.CO$ in $R^3$ includes formyl, acetyl, propionyl, cyclopropanecarbonyl, valeryl, butylyl, cyclopropylmethylcarbonyl, pivaloyl, trifluoroacetyl, phenylacetyl, 3-phenylpropionyl, pyridylcarbonyl, benzoyl, tetrahydro-2-furoyl, tetrahydro-3-furoyl, methoxycarbonyl, ethoxycarbonyl, propyloxycarbonyl, isopropyloxycarbonyl, butyloxycarbonyl, t-butyloxycarbonyl, benzyloxycarbonyl, 9-fluorenyloxycarbonyl, 2,2,2-trichloroethoxycarbonyl, allyloxycarbonyl, hydroxyoxalyl etc.

An acyl group of D.CO.E.CO or $D.SO_2.E.CO$ in $R_3$ includes 4-[1-(4-morpholine-1-yl)carbonyl] benzenecarbonyl, 4-[(1-pyrrolidine-1-yl) carbonyl] benzenecarbonyl, 4-[(1-piperidine-1-yl)carbonyl] benzenecarbonyl, phenylsulfonylaminocarbonyl etc.

$D(CH_2)_{0-3}.S)_2$ in $R^3$ includes e.g. toluenesulfonyl, benzenesulfonyl, formaminobenzenesulfonyl, nitrobenzenesulfonyl, methoxybenzenesulfonyl, pyridylsulfonyl, pyridylmethylsulfonyl, methylsulfonyl, ethylsulfonyl, propylsulfonyl, butylsulfonyl, t-butylsulfonyl, benzylsulfonyl, trifluoromethylsulfonyl, phenacylsulfonyl, aminosulfonyl, methylaminosulfonyl, ethylaminosulfonyl, propylaminosulfonyl, isopropylaminosulfonyl, butylaminosulfonyl, t-butylaminosulfonyl, phenylaminosulfonyl, benzylaminosulfonyl, pyridylaminosulfonyl, pyridylmethylaminosulfonyl etc.

$D.CO.E.SO_2$ in $R^3$ includes benzoylaminosulfonyl etc.

The thiourea represented by $R_bR_cN.CS$ in $R^3$ includes methylaminothiocarbonyl, ethylaminothiocarbonyl, propylamino-thiocarbonyl, butylaminothiocarbonyl, isopropylaminothio-carbonyl, valerylaminothiocarbonyl, benzylaminothiocarbonyl etc.

A preferable example of $R^0$ is a phenyl group whose ring may have 1 to 4 substituent groups selected from halogen, nitro, a hydroxyl group, a lower alkoxy group, a lower alkyl group, and a trifluoromethyl group as group A.

A preferable example of $R^1$ is phenyl, furyl, thienyl or pyridyl whose ring may have 1 or 2 substituent groups defined as group A.

Preferable examples of $R^2$ are (1–4C) alkyl, aryl (1–3C) alkyl and G(1–3C) alkyl having the previously defined group G as a substituent group. More preferable examples are methyl, ethyl, propyl, butyl, isopropyl, benzyl, phenethyl, phenylpropyl, pyridylmethyl, pyridylethyl, pyridylpropyl, furylmethyl, furylethyl, furylpropyl, pyridyloxymethyl, pyridyloxyethyl, pyridyloxypropyl, or groups which may have a substituent group selected from methyl, ethyl, propyl, butyl, isopropyl, benzyl or pyridylmethyl at the 4-position, such as piperazine-1-yl-(1–3C) alkyl, piperidine-1-yl-(1–3C) alkyl, 4-morpholine-4-yl-(1–3c) alkyl, 2-pyridyloxy (1–3C) alkyl, pyrrolidine-1-yl-(1–3C) alkyl, 2-oxo-1,2-dihydropyridine-1-yl-(1–3C) alkyl, methoxycarbonyl (0–3C) alkyl, ethoxycarbonyl (0–3C) alkyl, propyloxycarbonyl (0–3C) alkyl, butyloxycarbonyl (0–3C) alkyl, benzyloxycarbonyl (0–3C) alkyl, t-butoxycarbonyl (0–3C) alkyl, phenyloxycarbonyl (0–3C) alkyl, nitrophenyloxycarbonyl (0–3C) alkyl, and bromophenyloxycarbonyl (0–3C) alkyl. More preferable examples are methyl, ethyl, propyl, butyl, phenylpropyl, 4-morpholine-4-yl-(1–3C) alkyl, 2-oxo-1,2-dihydropyridine-1-yl-(1–3C) alkyl, 2pyridyloxy (1–3C) alkyl, ethoxycarbonyl (0–3C) alkyl, and 4-methylpiperazine-1-yl-carbonyl (1–3C) alkyl.

Preferable examples of $R^3$ are hydrogen, formyl, acetyl, propionyl, cyclopropanecarbonyl, valeryl, butyryl, cyclopropylmethylcarbonyl, pivaloyl, trifluoroacetyl, phenylacetyl, 3-phenylpropionyl, pyridylcarbonyl, benzoyl, tetrahydro-2-furoyl, tetrahydro-3-furoyl, methoxycarbonyl, ethoxycarbonyl, propyloxycarbonyl, isopropyloxycarbonyl, butyloxycarbonyl, t-butyloxycarbonyl, benzyloxycarbonyl, 9-fluorenyloxycarbonyl, 2,2,2-trichloroethoxycarbonyl, allyloxycarbonyl, hydroxyoxalyl, 4-[1-(4-morpholine-4-yl)-carbonyl]benzenecarbonyl, 4-[(1-pyrrolidine-1-yl)carbonyl]] benzenecarbonyl, [4-(1-piperidine-1-yl)-carbonyl] benzenecarbonyl, toluenesulfonyl, benzenesulfonyl, formaminobenzenesulfonyl, nitrobenzenesulfonyl, methoxybenzenesulfonyl, pyridylsulfonyl, pyridylmethylsulfonyl, methylsulfonyl, ethylsulfonyl, propylsulfonyl, butylsulfonyl, t-butylsulfonyl, henzylsulfonyl, trifluoromethylsulfonyl, phenacylsulfonyl, aminosulfonyl, methylaminosulfonyl, ethylaminosulfonyl, propylaminosulfonyl, isopropylaminosulfonyl, butylaminosulfonyl, t-butylaminosulfonyl, phenylaminosulfonyl, benzylaminosulfonyl, pyridylaminosulfonyl, pyridylmethylaminosulfonyl, methylaminothiocarbonyl, ethylaminothiocarbonyl, propylaminothiocarbonyl, butylaminothiocarbonyl, isopropylaminothiocarbonyl, valerylaminothiocarbonyl, benzylaminothiocarbonyl, (wherein these groups may have one or two halogen groups or methyl groups on the ring if these groups have phenyl or heteroaryl as a partial structure), methyl, ethyl, propyl, isopropyl, butyl, t-butyl, benzyl, phenethyl, thiazolyl, pyridylmethyl or 5-tetrazolylmethyl (wherein if these groups have phenyl or heteroaryl as a partial structure, one or two halogen groups or methyl groups may be present on the ring).

An element preferable as X and Y is carbon or nitrogen.

A preferable group: of Z is a polymethylene group containing 1 to 3 carbon atoms, more preferably a methylene group.

Particularly preferable groups of the (1–8C) straight-chain and branched alkyl are methyl, ethyl, propyl, isopropyl, butyl, isobutyl, amyl, isoamyl, hexyl, heptyl and octyl. Particularly preferable groups of the cyclic alkyl are cyclopropyl, cyclobutyl, cyclopentyl, and cyclohexyl. Useful groups as alkylene in the aryl (1–7C) alkyl and heteroaryl (1–7C) alkyl are methylene, ethylene, trimethylene, tetramethylene, pentamethylene, hexamethylene and heptamethylene. A particularly preferable group of aryl is phenyl. Particularly useful groups of heteroaryl are pyridyl, pyrimidinyl, furyl and thienyl. Preferable examples of aryl (1–7C) alkyl are phenylmethyl, phenylethyl, phenylpropyl, phenylisopropyl, phenylbutyl, phenylisobutyl, phenylamyl, phenylisoamyl, phenylhexyl, and phenylheptyl, and preferable examples in heteroaryl (1–7C) alkyl are the same as in the case of the phenyl group when the heteroaryl is pyridyl, pyrimidinyl, furyl or thienyl.

Particularly useful groups of lower alkyl are methyl, ethyl, propyl, isopropyl, butyl, isobutyl and t-butyl. Particularly preferable groups of lower alkoxy groups are methoxy, ethoxy, propyloxy, isopropyloxy and butoxy. Particularly preferable groups of halogen are fluorine, chlorine and bromine.

As the particular groups in the compound of formula (I), $R^0$, $R^2$, $R^3$, X, Y, and Z are any of the above, and $R^1$ is phenyl.

One of particular groups-of more specified compounds of formula (I) is compound wherein each symbol has the following meanings.

$R^0$ is a phenyl group whose ring may have 1 to 3 substituent groups selected from halogen, a hydroxyl group, a lower alkoxy group, a lower alkyl group and a trifluoromethyl group as group A.

$R^1$ is a phenyl group whose ring may independently have one or more of the above-defined group A on the ring; or $R^1$ may have one or more substituent groups selected from group B consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$ and $P(O)(OR_a)_2$.

$R^2$ represents pyridyloxy (1–4C) alkyl.

$R^3$ is hydrogen; or $R^3$ is an acyl group of (i) $D.(CH_2)_{0-3}.CO$, (ii) $D.CO.E.CO$ or (iii) $D.SO_2.E.CO$, or a sulfonyl group of $D.(CH_2)_{0-3}SO_2$ and $D.CO.E.SO_2$ (wherein group D represents hydrogen, a C1–6 straight-chain, branched or cyclic alkyl group, trifluoromethyl, 2,2,2-trifluoroethoxy, 2,2,2-trifluoroethylamino, $COOR_a$, $CONR_bR_c$, $NR_bR_c$, or the defined group G; or $R^3$ is thiourea represented by $R_bR_cN.CS$; and group E independently represents phenyl, heteroaryl, 1,4-piperazine-di-yl, cyclohexyl, 1,4-cyclohexadienyl); or $R^3$ is $R_a$.

X and Y independently represent a nitrogen atom or an unsubstituted carbon atom.

Z represents —$CH_2$— wherein the 2 hydrogen atoms may independently be replaced by $R_a$ and $R_b$.

In particular groups of more specified compounds of formula (I), $R^0$ is a phenyl group (the phenyl group may independently have 1 or 2 groups of halogens, hydroxyl groups or methyl groups), $R^2$ is methyl, butyl, phenylpropyl, 4-morpholine-4-yl-propyl, 1-(ethoxycarbonyl)propyl, 4-methylpiperazine-1-yl-propyl, 2-oxo-1,2-dihydropyridine-1-yl-propyl or 2-pyridyloxypropyl, $R^3$ is hydrogen or formyl, X and Y are unsubstituted carbon or nitrogen, and Z is an unsubstituted methylene group. More specifically, $R^0$ is phenyl, 3-fluorophenyl, 4-fluorophenyl, 3,4-difluorophenyl, 3,5-difluorophenyl, or 3-fluoro-4-hydroxyphenyl.

Pharmacologically acceptable salts of the compound of formula (I) are not particularly limited, and when the compound of formula (I) is e.g. an acidic compound, its pharmacologically acceptable salts are alkali metal salts, alkaline earth metal salts, aluminum salts, ammonium salts or those obtained from organic bases forming pharmaceutically acceptable cations such as primary to tertiary lower alkyl s Namines etc.; (B) when the compound of formula (I) is a basic compound, its pharmacologically acceptable salts are acid-added salts formed by using an acid such as hydrochloric acid, sulfuric acid, sulfonic acid, phosphoric acid etc. forming pharmacologically acceptable anions.

The compound of formula (I) can be produced by a method including a known step among chemical techniques for producing structurally analogous heterocyclic compounds or peptide compounds. For example, the objective compound of formula (I) is obtained by condensation between the compound of formula 5 or its derivative activated in the carboxyl group and the compound of formula 3 wherein $R^{3'}$ is hydrogen, to give the compound of formula (II), followed by oxidization thereof and removal of a protective group (Boc(t-butyloxycarbonyl) in scheme 1) for the amino group as necessary, as shown in scheme 1 below.

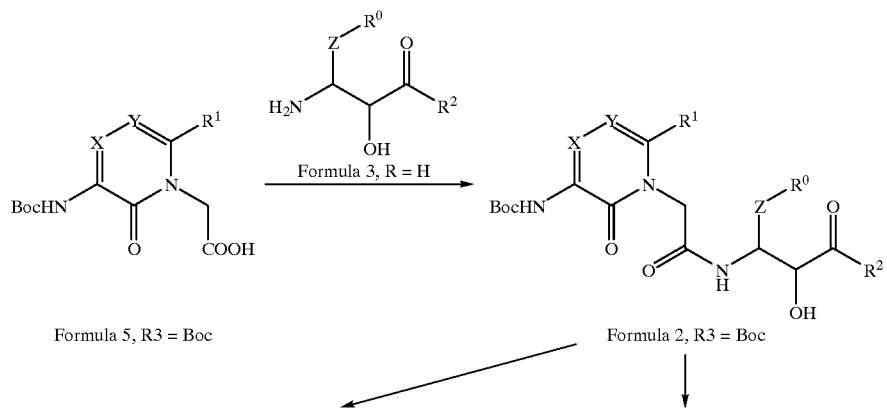

Scheme 1

-continued

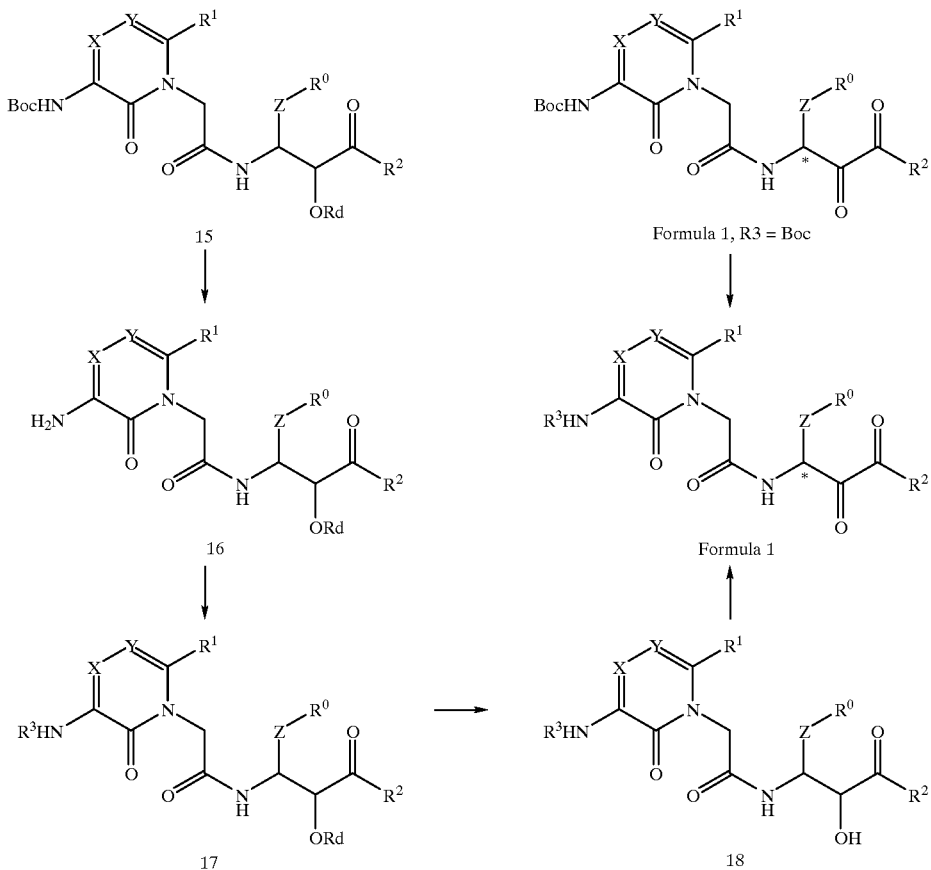

Condensation between the compound of formula (V) or its derivative activated in the carboxyl group and the compound of formula (III) wherein $R^{3'}$ is hydrogen may be conducted in an inert solvent for example a polar solvent such as dimethylformamide, tetrahydrofuran or the like, or in a mixed solvent thereof with a nonpolar solvent, for example at a temperature of about 0 to 80° C., preferably at a temperature of about 0 to 40° C., for about 0.5 to 50 hours. In the reaction, the molar ratio of the compound of formula (V) or its derivative activated in the carboxyl group and the compound of formula (III) wherein $R^{3'}$ is hydrogen is preferably selected such that the compound of formula (III) is used in an excess amount slightly larger than the theoretical amount, but the amount of the compound of formula (III) can be arbitrarily changed in the range of 0.5- to 5-fold excess amount per mol of the compound of formula (V).

Particularly in preparing the compound wherein $R^3$ is a group other than hydrogen, a hydroxyl group in the compound of formula (II) is protected with the protective group Rd to give the compound of formula (XV), and the protective group (Boc in scheme 1) for the amino group is eliminated in e.g. hydrogen chloride/1,4-dioxane solution to give the compound, of formula (XVI), and then the group of the protective group $R^3$ is introduced by a usual manner depending on the type of the group to give the compound of formula (XVII). Deprotection of the hydroxyl group in formula (XVIII) gives the compound of formula (XVIII) followed by oxidation to give the objective compound of formula (I). Rd in formula (XV) may be any protective group used for protecting a hydroxyl group, and acyl group etc. quoted in the definition of $R^3$ are usually used. Preferably, a protective group not removed upon subsequent elimination of the protective group for the amino group is preferably used.

As is evident to those skilled in the art, the starting materials can be synthesized in various synthetic pathways.

For example, for the compound of formula (III) or salts thereof, the corresponding ketone derivative of oxazolidine is subjected in a usual manner to de-protection reaction of the amino group and ring-opening reaction of the oxazolidine, whereby the compound of formula (III) or salts thereof can be easily obtained. In formula (III), $R^{3'}$, independently of $R^3$, has the same meaning as $R^3$ and is preferably a protective group such as acyl group defined for $R^3$ except for the case of condensation with the compound of formula (V) or (VI). The ketone derivative of said oxazolidine can be synthesized as shown in the following steps (1) to (4):

(1) According to the method reported by R. Nishizawa et al. in J. Med. Chem., 20(4), 510–515, 3-amino-2-hydroxy-4-substituted or unsubstituted phenyl butyric acid can be easily synthesized using an amino acid as the starting material.

The amino acid used as the starting material may be a commercial product, e.g. substituted or unsubstituted phenylalanine etc. If not commercially available, conventional amino acid synthesis reaction, for example, the condensation reaction of a commercial acetamide malonic acid ester with substituted benzyl chloride is conducted, and then the ester is subjected to hydrolysis and subsequent decarboxylation reaction, and the amino group is de-protected whereby a desired amino acid, for example, substituted phenylalanine having a substituent group introduced into the aromatic ring, can be obtained.

(2) The 3-amino group of the resulting 3-amino-2-hydroxy-4-substituted or unsubstituted phenylbutyric acid is protected with a suitable protective group such as t-butyloxycarbonyl group etc. and then subjected in a usual manner to condensation reaction with N,O-dimethylhydroxylamine or a salt thereof, whereby 3-N-protected amino-2-hydroxy-4-substituted or unsubstituted phenylbutyric acid-N,O-dimethylhydroxylamide can be obtained.

(3) The resulting amide is treated in a usual manner with e.g. a catalytic amount of p-toluenesulfonic acid in 2,2-dimethoxypropane whereby 3-N-protected-5-(N-methoxy-N-methyl)carbamoyl-2,2-dimethyl-4-substituted or unsubstituted phenylmethyloxazolidine can be easily obtained.

(4) As is apparent to those skilled in the art, the resulting amide is known as an activated amide. Accordingly, it can be easily converted into a ketone derivative in the following operation. Specifically, the oxazolidine subjected to known reaction, e.g. treatment with a Grignard reagent corresponding to a group $R^2$ in an inert solvent in argon atmosphere according to a method disclosed in Japanese Laid-Open Patent Publication No. 143517/1996 as described above, whereby the N,O-dimethylhydroxylamino group is substituted by the group $R^2$, so that the ketone derivative of the oxazolidine having the group $R^2$ introduced into it can be synthesized. The resulting ketone derivative of the oxazolidine and salts thereof can be represented by the following chemical formula (XXV).

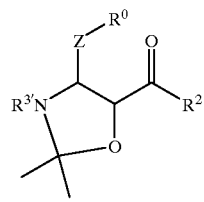

(XXV)

wherein $R^0$, $R^2$ and Z are the groups defined in claim 1, and $R^{3'}$ has the same meaning as $R^3$ defined in claim 1.

3-$R^{3'}$-5-($R^2$CO)-2,2-di-lower alkyl-4-($R^0$-Z) oxazolidine referred to in the present specification has the same meaning as in formula (XXV).

Further, the intermediate of formula (V), i.e. pyrazine-3-one-4-acetic acid (in formula (V), X is nitrogen and Y is carbon), can be synthesized by the pathway shown in scheme 2 according to one of utilizable synthetic pathways. In this scheme, Boc is a t-butyloxycarbonyl group, and CBZ is a benzyloxycarbonyl group.

Scheme 2

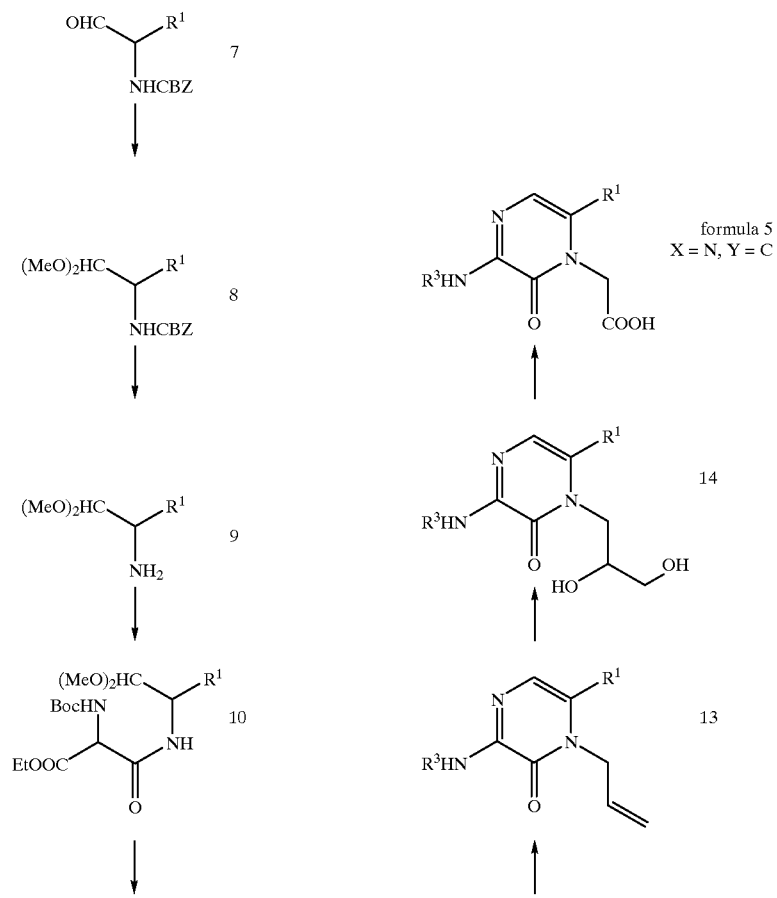

-continued

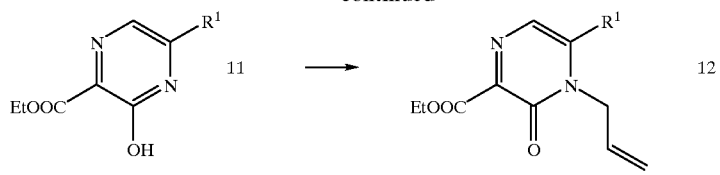

The aldehyde of formula (VII) can be easily synthesized by the synthetic method reported by D. H. Rich et al. in J. Org. Chem. 43(18), 3624–3626 (1978). This aldehyde is treated with a suitable alcohol (methanol in this case) in the presence of an acid catalyst whereby the compound of formula (VIII) can be obtained. The benzyloxycarboxyl group in formula (VIII) is hydrogenolyzed in a usual manner whereby the compound can be easily converted into the compound of formula (IX). The amine of formula (IX) and the t-butyloxycarbonylaminomalonic acid monoester are subjected to condensation in a usual manner whereby the compound of formula (X) can be easily obtained.

The compound of formula (X) can be converted into the compound of formula (XI) by ring-closing reaction of formula (X) using the synthetic method reported by E. Taguchi et al. in Peptide Chemistry, 160–172 (1995). The compound of formula (XI) is treated with a suitable base in the presence of an alkylating reagent such as allyl bromide whereby 4,5-di-substituted-3-pyrazinone-2-carboxylate represented by formula (XII) can be synthesized.

The carboxyl protective group of the compound of formula (XII) is hydrolyzed in a usual manner whereby the compound can be easily converted into carboxylic acid. After this carboxylic acid is purified or not purified in some cases, the compound is treated with diphenylphosphorylazide and a suitable base such as triethylamine in an inert solvent whereby the corresponding isocyanate can be generated. In a simple method as is evident to those skilled in the art, the reaction is conducted in the presence of e.g. t-butyl alcohol whereby the compound of formula (XIII) wherein e.g. $R^3$ is a t-butyloxycarbonyl group can be easily synthesized.

Conversion of the compound of formula (XIII) into the compound of formula (V) can be effected in 3 steps in a usual manner. That is, conversion of the compound of formula (XIII) into the diol of formula (XIV) can be conducted by use of a catalytic amount of osmium tetroxide in the presence of a co-oxidizing agent such as N-methylmorpholine-N-oxide. Then, the compound of formula (XIV) is treated with sodium periodate and then treated with an oxidizing agent such as sodium chlorite whereby the compound of formula (V) can be easily obtained.

The intermediate of formula (V), i.e. pyrimidine-6-one-1-acetic acid (in formula (V), X is carbon and Y is nitrogen), is known according to e.g. Japanese Laid-Open Patent Publication No. 286946/1993, and the unknown compounds can also be produced according to the method described in said literature or the method described above. The intermediate of formula (VI), triazine-5-one-4-acetic acid, can be synthesized in the pathway shown in scheme 3.

Scheme 3

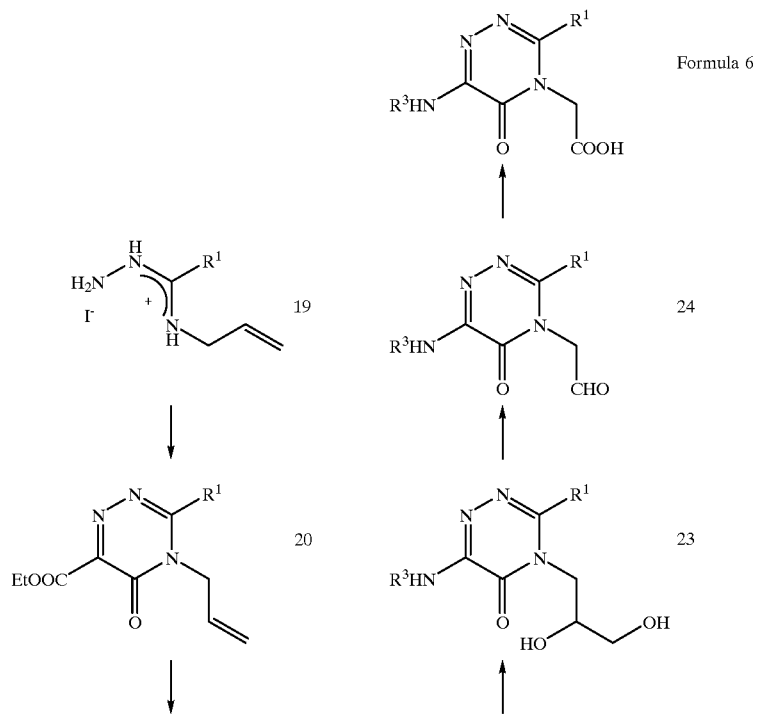

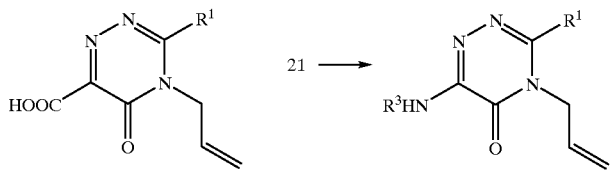

The amidolazone of formula (XIX) can be synthesized by the synthetic method reported by H. J. Metz and H. Neunhoeffer in Chem. Ber. 115, 2807–2818 (1982). This amidolazone can be converted into 3,4-di-substituted-5-triazinone-6-carboxylate of formula (XX) by subjecting it without isolation and purification to ring-forming reaction with diethylketomalonate in the presence of a suitable base. The carboxyl protective group of formula (XX) is hydrolyzed in a usual manner, so that the compound can be converted into 3,4-di-substituted-5-triazinone-6-carboxylic acid of formula (XXI).

The carboxylic acid of formula (XXI) can be converted into the compound of formula (XXII) (in this case, $R^3$=t-butyloxycarbonyl group) by known reaction for example by treating it with diphenylphosphoryl azide and a suitable base such as triethylamine in the presence of t-butyl alcohol. This conversion is known to proceed via isocyanate, so it is evident to those skilled in the art that if amine or the like is used in place of t-butyl alcohol, the compound can be easily converted into the corresponding compound where $R^3$ is a group of urea type.

The conversion of the compound of formula (XXII) into the compound of formula (VI) can be conducted in the same manner as for the conversion of the compound of formula (XIII) into the compound of formula (V).

The steps and the intermediates for producing the compound of formula (I) described above are other aspects of the present invention and these are shown in the steps shown below. The groups used herein are as defined above.

(A) Oxidization reaction of the alcohol of formula (II) into carbonyl group

Oxidation of the compound of formula (II) can be conducted by a conventional method used for oxidizing a hydroxyl group into a carbonyl group, but a method hardly causing side reaction is preferably selected. Usually, it can be obtained by oxidization in an inert solvent, preferably a polar solvent such as dimethylformamide or tetrahydrofuran, a halogeno solvent such as methylene chloride, or a mixed solvent thereof, preferably in the presence of an excess oxidizing agent at a temperature in the range of –10° C. to 100° C., preferably at a temperature in the range of 10° C. to 50° C. or thereabout, more preferably at room temperature or thereabout. A preferable oxidizing agent includes an agent using excess. dimethylsulfoxide and water-soluble carbodiimide and as catalyst pyridinium trifluoroacetate; using 3 compounds of oxalyl chloride, dimethylsulfoxide and a tertiary amine; using pyridinium chlorochromate in methylene chloride and the like.

If the amino group is not stable under reaction conditions for oxidation, introduction of an amino protective group as $R^3$ before oxidation and removal of the protective group after oxidation is preferable or necessary.

(B) Synthetic of the free amino group-containing compound of formula (I)

From a corresponding compound containing a conventional amino-protective group, the amino-protective group may be removed by a conventional method. The conventional removal method includes e.g. removal by treatment with a strong acid such as hydrogen chloride in an inert solvent such as 1,4-dioxane; and removal by heating treatment in the coexistence of p-toluenesulfonic acid in methanol. These reactions can be conducted at a temperature in the range of –10°C. to 100° C., preferably at a temperature in the range of 10° C. to 50° C. or thereabout, more preferably at room temperature or thereabout.

The following compounds can be obtained by condensation between the compound of formula 5 or its derivative activated in the carboxyl group and the compound of formula (III) wherein $R^{3'}$ is hydrogen, but they can be obtained in the following methods.

(C) Synthesis of the compound of formula (I) wherein $R^3$ is an acyl group

From the compound of formula (V) wherein $R^3$ is a t-butoxycarbonyl group, said t-butoxycarbonyl group is removed whereby the primary amino group-containing compound of formula (I) wherein $R^3$ is hydrogen is obtained, and said primary amino group is acylated to give the objective compound. An easy method is acylation using an acid halide corresponding to the acyl group in an inert solvent such as tetrahydrofuran. Another useful method is condensation reaction using a corresponding carboxylic acid and a coupling reagent such as dicyclohexylcarbodiimide, 1-(3-dimethylaminopropyl)-3-ethylcarbodiimide, and its salt etc.

(D) Synthesis of the compound of formula (I) wherein $R^1$ or $R^2$, or $R^2$, has $COOR_a$, $CONR_bR_c$.

The compound can also be obtained by acylation due to condensation reaction between a compound having the group $HOR_a$, $HNR_bR_c$ and the compound of formula (I) having the group COOH (or its activated derivative) on $R^1$ or $R^2$.

(E) Synthesis of the compound of formula (I) wherein $R^3$ is a sulfonyl group

The free amino group-containing compound of formula (I) wherein $R^3$ is hydrogen is sulfonylated with sulfonyl chloride corresponding to the desired compound, so that the desired compound can be obtained. In this case, the reaction can be carried out at room temperature or under cooling on ice in the presence of a tertiary amine in an inert solvent such as tetrahydrofuran. If the sulfonyl chloride is not commercially available, the desired sulfonyl chloride can be synthesized in a method known in the art.

(F) Conventional substitution reaction, by the amine compound of formula (I) wherein $R^3$ is hydrogen, of the eliminating group L in the compound having $R_a$-L having the usual eliminating group L such as halogen, methylsulfonyloxy, trifluoromethylsulfonyloxy, to synthesize the compound of formula (I) wherein $R^3$ is $R_a$ excluding hydrogen (G) Cleavage reaction of a corresponding alkyl ether or acyloxy ester of the compound of formula (I) having a lower alkoxy substituent group or a lower acyloxy substituent group on the aryl or heteroaryl group thereof, to synthesize the compound of formula (I) wherein at least one of $R^1$, $R^2$ and $R^3$ has a hydroxyl group as a substituent group on the aryl or heteroaryl ring A convenient method is hydrolysis of the acyloxy group under acidic or alkaline conditions etc.

(H) Synthesis of the compound of formula (I) wherein $R^1$ or $R^2$ is carboxyl-substituted, or $R^2$ is a carboxyl group ($R_a$ in the group $COOR_a$ is hydrogen)

The compound can be obtained by removing an ester group from the corresponding ester compound having a carboxyl group. This reaction includes hydrolysis with an alkali such as sodium hydroxide, hydrogenolysis in the case of benzyl ester, and decomposition of t-butyl ester under acid conditions etc.

(I) Synthesis of the compound of formula (I) wherein $R^3$ is $R_bR_cNCO$ or $R_bR_cNCS$, and $R_c$ is hydrogen The compound can be obtained in a usual manner by acylating the amino group in the free amino group-containing compound of formula (I) by an isocyanate or thioisocyanate corresponding to the group of formula $R_bNCO$ or $R_bNCS$.

(J) Synthesis of the compound of formula (III) wherein $R^2$ is alkyl, arylalkyl or heteroarylalkyl The compound can be obtained by alkylating the compound of formula (III) having a carboxyl group or its activated derivative by reaction with an alkyl Grignard reagent, arylalkyl Grignard reagent or heteroarylalkyl Grignard reagent having a group corresponding to $R^2$.

(K) Conventional synthesis of the compound of formula (I) or (II)

The compound can be obtained in a usual manner by condensation between the compound of formula (V) or (VI) (or its derivative activated in the COOH in the structural formula) and the compound of formula (IV) or (III) wherein $R^3$ is hydrogen.

(L) The above items (C), (D), (E), (F), (G), (H) and (I) are reactions for preparing the compounds represented by formula (I), and in accordance with these reactions, compounds as intermediates having the same groups as in formulae (III), (IV), (V), and (VI) can be obtained. Condensation of these intermediates can give the compounds of formula (I) similarly. There are cases where it is desired to use a protective group in all the synthetic steps described above. This protective group can be removed at the stage when the final product or the desired compound has been synthesized. As is evident to those skilled in the art, a series of steps leading to the starting material and the final product in the present invention can be modified in suitable consideration of the method of condensation and the method of removing the protective group.

Among the compounds of formula (I) obtained in the manner described above, preferable compounds include the above-described Compound Nos. 72, 73, 74, 75, 76, 77, 78, 79, 80, and 82 etc. Particularly preferable are 79 and 82 etc.

Preferable examples of the compounds of formula (V) are as follows:
2-t-Butyloxycarbonylamino-3-oxo-5-phenyl-3,4-dihydropyrazine-4-yl-acetic acid (in formula (V), X is nitrogen, Y is carbon, $R^3$ is t-butyloxycarbonyl, $R^1$ is phenyl), 5-t-Butyloxycarbonylamino-6-oxo-2-phenyl-1,6-dihydro-1-pyrimidinylacetic acid (in formula (V), X is carbon, Y is nitrogen, $R^3$ is t-butyloxycarbonyl, $R^1$ is phenyl), and 6-t-Butyloxycarbonylamino-5-oxo-3-phenyl-4,5-dihydro-1,2,4-triazinylacetic acid (in formula (V), X and Y both are nitrogen, $R^3$ is t-butyloxycarbonyl, $R^1$ is hydrogen).

Examples of preferable compounds of formula (III) are as follows:
(A) Methyl 3-amino-2-hydroxy-4-(4-hydroxyphenyl)-butyrate
(B) Methyl 3-amino-2-hydroxy-4-(3-fluoro-4-hydroxyphenyl)-butyrate
(C) 3-Amino-2-hydroxy-4-phenyl-propananilide
(D) 3-Amino-2-hydroxy-4-phenyl-N-phenylmethyl-butylamide
(E) 3-Amino-2-hydroxy-4-phenyl-N-phenylethyl-butylamide
(F) Methyl 3-amino-2-hydroxy-4-(4-methyloxyphenyl)-butyrate The following compounds are also cited as preferable compounds.
(A) 2-Amino-3-hydroxy-4-oxo-1-phenylpentane
(B) 2-Amino-1,7-diphenyl-3-hydroxy-4-oxoheptane
(C) 2-Amino-1,6-diphenyl-3-hydroxy-4-oxohexane
(D) 2-Amino-3-hydroxy-4-oxo-1-phenyloctane
(E) 2-Amino-1,4-diphenyl-3-hydroxy-4-oxobutane
(F) 7-Amino-3-hydroxy-5-oxo-8-phenyloctanoic acid
(G) 2-Amino-1-(3-fluoro-4-hydroxyphenyl)-3-hydroxy-4-oxopentane
(H) 2-Amino-1-(3-fluorophenyl)-3-hydroxy-4-oxopentane
(I) 2-Amino-1-(3-chlorophenyl)-3-hydroxy-4-oxopentane
(J) 2-Amino-3-hydroxy-1-(3-methylphenyl)-4-oxopentane
(K) 2-Amino-1-(.4-fluorophenyl)-3-hydroxy-4-oxopentane
(L) 2-Amino-1-(4-chlorophenyl)-3-hydroxy-4-oxopentane
(M) Ethyl 2-amino-1-(3-fluorophenyl)-3-hydroxy-4-oxooctanoate
(N) 2-Amino-1-(3-fluorophenyl)-3-hydroxy-4-oxooctane-(4-methylpiperazine) amide
(O) 2-Amino-3-hydroxy-7-(4-morpholine-4-yl)-4-oxo-1-phenylheptane
(P) 2-Amino-7-(2-oxo-1,2-dihydropyridine-1-yl)-3-hydroxy-4-oxo-1-phenylheptane
(Q) 2-Amino-3-hydroxy-4-oxo-1-phenyl-7-(2-pyridyloxy) heptane
(R) Methyl 3-amino-2-hydroxy-4-phenyl-butyrate If the present compound is used as a chymase inhibitor, it is used alone or mixed with excpients or carriers and administered orally or parenterally as a pharmaceutical composition such as injection, inhalant, tablets, granules, subtle granules, powder, capsules, suppositories, instillations, paste agents, ointments, sprays etc. As excpients or carriers, pharmaceutically acceptable additives are selected and the type and composition are determined according to the administration route and administration method. For example, in the case of an injection, sodium chloride or saccharides such as glucose, mannitol etc. is generally preferable. In the case of oral preparations, starch, lactose, crystalline cellulose, magnesium stearate etc. are preferable.

The content of the present compound in the pharmaceutical composition varies depending on the preparation, but is usually in the range of 0.1 to 100% by weight, preferably 1 to 98% by weight. For example, in the case of an injection, the active ingredient is contained in the range of usually 0.1 to 30% by weight, preferably 1 to 10% by weight. In the case of an oral preparation, the present compound is used with additives in the form of tablets, capsules, powder, granules, liquid, dry syrup etc. The capsules, tablets, granules and powder contain generally 5 to 100% by weight of the active ingredient, preferably 25 to 98% by weight.

Although the dosage is determined depending on the age, weight and symptom of the patient, the object of therapy etc., the therapeutic amount is usually 1 to 100 mg/kg/day for parenteral administration and 5 to 500 mg/kg/day for oral administration.

The present compounds are characterized in that they are low toxic and even the successive administration of the present compounds does not cause high toxic accumulation. For example, even if the present compound is orally administered into a hamster at a dosage of 100 mg/kg twice per day for 3 weeks, no symptom of toxicity was observed.

Hereinafter, the present invention is described by non-limiting examples. Unless otherwise noted, the following procedures were used.
(1) The solvent was concentrated under a reduced pressure of 5 to 20 mmHg in a rotary evaporator in a water bath at a temperature of 50° C. or less;

(2) Silica gel chromatography was conducted using BW-820 MH (Fuji Silicia); preparative thin layer chromatography has used a TLC plate having a thickness of 0.25 or 0.5 mm as necessary (silica gel 60F254, 20×20 cm) (Merck); the elution solvent/developing solvent ratio was indicated in volume/volume;
(3) The melting point was not corrected, and (dec) indicates decomposition; the substance whose melting point was described is a substance synthesized in the method described in the Examples, and even if it was synthesized by the same method, it may show a different melting point from the described value if it has crystalline polymorphism;
(4) The final product was given a satisfactory nuclear magnetic resonance (NMR) spectrum;
In NMR, Gemini-200 (200 MHz) produced by Varian was used and it is described in ppm with tetramethylsilane (TMS) as internal standard substance; customary abbreviations were used for the shapes of detected signals;
(5) Mass spectrum was measured using VG Auto Spec (VG Co., Ltd.) by the EI method or the FAB method;,
(6) Infrared (IR) absorption spectrum was measured by IR spectrophotometer A-202 (Nippon Bunko) using a polystyrene film as standard substance;
(7) In general, TLC was used for monitoring the reaction; the reaction time is merely illustrative and the optimum time is not necessarily described;
(8) The yield is described for explanation, and it does not necessarily agree with amount of the substance synthesized by an optimum method; if a large amount of substance was necessary, its synthesis was repeatedly conducted until a necessary amount of the substance was obtained.

EXAMPLES

Hereinafter, the present invention is described in detail by reference to the Examples, which however are not intended to limit the present invention. The compounds of formula (I) (Tables 1 to 5) and the compounds of formula (II) (Tables 6 to 10) synthesized in the following examples are shown in the tables.

TABLE 1

| Compound No. | R0 | R1 | R2 | R3 | X | Y | Z |
|---|---|---|---|---|---|---|---|
| 37 | Ph | Ph | Me | Boc | C | N | —CH2— |
| 38 | Ph | Ph | Me | HCl.H | C | N | —CH2— |
| 39 | Ph | Ph | —(CH2)3Ph | Boc | C | N | —CH2— |
| 40 | Ph | Ph | —(CH2)3Ph | HCl.H | C | N | —CH2— |
| 41 | Ph | Ph | —(CH2)2Ph | Boc | C | N | —CH2— |
| 42 | Ph | Ph | —(CH2)2Ph | HCl.H | C | N | —CH2— |
| 43 | Ph | Ph | n-Bu | Boc | C | N | —CH2— |
| 44 | Ph | Ph | n-Bu | HCl.H | C | N | —CH2— |
| 45 | Ph | Ph | Ph | Boc | C | N | —CH2— |
| 46 | Ph | Ph | Ph | HCl.H | C | N | —CH2— |

TABLE 2

| Compound No. | R0 | R1 | R2 | R3 | X | Y | Z |
|---|---|---|---|---|---|---|---|
| 47 | Ph | Ph | —(CH2)3COOH | Boc | C | N | —CH2— |
| 48 | Ph | Ph | —(CH2)3COOH | HCl.H | C | N | —CH2— |
| 49 | 3-F-4-OH—Ph | Ph | Me | Boc | C | N | —CH2— |
| 50 | 3-F-4-OH—Ph | Ph | Me | HCl.H | C | N | —CH2— |
| 51 | 3-F—Ph | Ph | Me | Boc | C | N | —CH2— |
| 52 | 3-F—Ph | Ph | Me | HCl.H | C | N | —CH2— |
| 53 | 3-F—Ph | Ph | —(CH2)3COOEt | Boc | C | N | —CH2— |
| 54 | 3-F—Ph | Ph | —(CH2)3COOEt | HCl.H | C | N | —CH2— |
| 55 | 4-F—Ph | Ph | Me | Boc | C | N | —CH2— |
| 56 | 4-F—Ph | Ph | Me | HCl.H | C | N | —CH2— |

TABLE 3

| Compound No. | R0 | R1 | R2 | R3 | X | Y | Z |
|---|---|---|---|---|---|---|---|
| 57 | 4-Cl—Ph | Ph | Me | Boc | C | N | —CH2— |
| 58 | 4-Cl—Ph | Ph | Me | HCl.H | C | N | —CH2— |
| 59 | 3-Me—Ph | Ph | Me | Boc | C | N | —CH2— |
| 60 | 3-Me—Ph | Ph | Me | HCl.H | C | N | —CH2— |

TABLE 3-continued

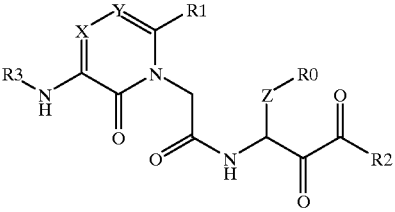

| Compound No. | R0 | R1 | R2 | R3 | X | Y | Z |
|---|---|---|---|---|---|---|---|
| 61 | 3-Cl—Ph | Ph | Me | Boc | C | N | —CH2— |
| 62 | 3-Cl—Ph | Ph | Me | HCl.H | C | N | —CH2— |
| 63 | 2-F—Ph | Ph | Me | Boc | C | N | —CH2— |
| 64 | 2-F—Ph | Ph | Me | HCl.H | C | N | —CH2— |
| 65 | 4-AcO-3-F—Ph | Ph | Me | Boc | C | N | —CH2— |
| 66 | Ph | Ph | OMe | Boc | N | C | —CH2— |
| 67 | Ph | Ph | OMe | HCl.H | N | C | —CH2— |

TABLE 4

| Compound No. | R0 | R1 | R2 | R3 | X | Y | Z |
|---|---|---|---|---|---|---|---|
| 68 | 3-F—Ph | Ph | ![butanoyl-4-methylpiperazine] | Boc | C | N | —CH2— |
| 69 | 3-F—Ph | Ph | ![butanoyl-4-methylpiperazine] | 2HCl.H | C | N | —CH2— |
| 70 | Ph | Ph | ![butyl-morpholine] | Boc | C | N | —CH2— |
| 71 | Ph | Ph | ![butyl-morpholine] | 2HCl.H | C | N | —CH2— |
| 72 | Ph | Ph | ![butyl-2-pyridone] | Boc | C | N | —CH2— |

TABLE 4-continued
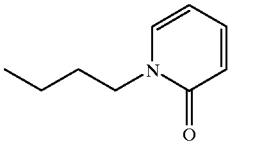
| Compound No. | R0 | R1 | R2 | R3 | X | Y | Z |
|---|---|---|---|---|---|---|---|
| 73 | Ph | Ph | 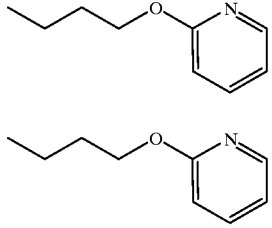 | HCl.H | C | N | —CH2— |
| 74 | Ph | Ph | 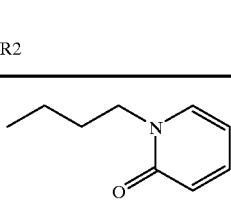 | Boc | C | N | —CH2— |
| 75 | Ph | Ph | 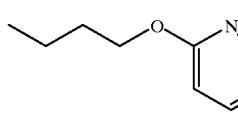 | 2HCl.H | C | N | —CH2— |
TABLE 5
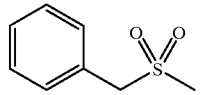
| Compound No. | R0 | R1 | R2 | R3 | X | Y | Z |
|---|---|---|---|---|---|---|---|
| 76 | Ph | Ph | 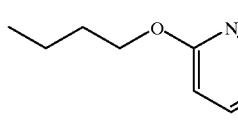 | Ac | C | N | —CH2— |
| 77 | Ph | Ph | 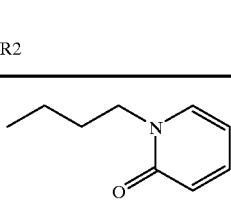 | 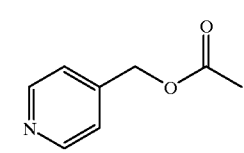 | C | N | —CH2— |
| 78 | Ph | Ph | 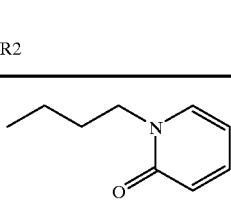 |  | C | N | —CH2— |

TABLE 5-continued

| Compound No. | R0 | R1 | R2 | R3 | X | Y | Z |
|---|---|---|---|---|---|---|---|
| 79 | Ph | Ph | butoxy-pyridine group | HCO | C | N | —CH2— |
| 80 | Ph | Ph | butoxy-pyridine group | Ac | C | N | —CH2— |
| 81 | Ph | Ph | 3-phenylpropyl group | 3-acetyltetrahydrofuran group | C | N | —CH2— |
| 82 | Ph | Ph | butoxy-pyridine group | benzyl methanesulfonamide group | C | N | —CH2— |

TABLE 6

| Compound No. | R0 | R1 | R2 | R3 | Rd | X | Y | Z |
|---|---|---|---|---|---|---|---|---|
| 1 | Ph | Ph | Me | Boc | H | C | N | —CH2— |
| 2 | Ph | Ph | —(CH2)3Ph | Boc | H | C | N | —CH2— |
| 3 | Ph | Ph | —(CH2)2Ph | Boc | H | C | N | —CH2— |
| 4 | Ph | Ph | n-Bu | Boc | H | C | N | —CH2— |
| 5 | Ph | Ph | Ph | Boc | H | C | N | —CH2— |
| 6 | Ph | Ph | —(CH2)3COOEt | Boc | H | C | N | —CH2— |
| 7 | 4-AcO-3-F—Ph | Ph | Me | Boc | H | G | N | —CH2— |
| 8 | 3-F—Ph | Ph | Me | Boc | H | C | N | —CH2— |
| 9 | 3-F—Ph | Ph | —(CH2)3COOEt | Boc | H | C | N | —CH2— |
| 10 | 3-F—Ph | Ph | butyl-(4-methylpiperazinyl)ketone group | Boc | H | C | N | —CH2— |

TABLE 7

| Compound No. | R0 | R1 | R2 | | R3 | Rd | X | Y | Z |
|---|---|---|---|---|---|---|---|---|---|
| 11 | Ph | Ph | (butyl-morpholine) | | Boc | H | C | N | —CH2— |
| 12 | Ph | Ph | (butyl-2-pyridone) | | Boc | H | C | N | —CH2— |
| 13 | Ph | Ph | (butoxy-pyridine) | | Boc | H | C | N | —CH2— |
| 14 | Ph | Ph | OMe | | Boc | H | N | C | —CH2— |
| 15 | 4-F—Ph | Ph | Me | | Boc | H | C | N | —CH2— |
| 16 | 4-Cl—Ph | Ph | Me | | Boc | H | C | N | —CH2— |
| 17 | 3-Me—Ph | Ph | Me | | Boc | H | C | N | —CH2— |
| 18 | 3-Cl—Ph | Ph | Me | | Boc | H | C | N | —CH2— |
| 19 | 3-F-4-OH—Ph | Ph | Me | | Boc | H | C | N | —CH2— |

TABLE 8

| Compound No. | R0 | R1 | R2 | R3 | Rd | X | Y | Z |
|---|---|---|---|---|---|---|---|---|
| 20 | 2-F—Ph | Ph | Me | Boc | H | C | N | —CH2— |
| 21 | Ph | Ph | (butyl-2-pyridone) | Ac | H | C | N | —CH2— |
| 22 | Ph | Ph | (butoxy-pyridine) | Boc | Ac | C | N | —CH2— |

TABLE 8-continued

| Compound No. | R0 | R1 | R2 | (R group structure) | R3 | Rd | X | Y | Z |
|---|---|---|---|---|---|---|---|---|---|
| 23 | Ph | Ph | | butoxy-pyridine | 2HCl.H | Ac | C | N | —CH2— |
| 24 | Ph | Ph | | butoxy-pyridine | benzyl methyl sulfone | Ac | C | N | —CH2— |
| 25 | Ph | Ph | | butoxy-pyridine | benzyl methyl sulfone | H | C | N | —CH2— |
| 26 | Ph | Ph | | butoxy-pyridine | pyridin-4-ylmethyl acetate | Ac | C | N | —CH2— |
| 27 | Ph | Ph | | butoxy-pyridine | pyridin-4-ylmethyl acetate | H | C | N | —CH2 |

TABLE 9

| Compound No. | R0 | R1 | R2 | R3 | Rd | X | Y | Z |
|---|---|---|---|---|---|---|---|---|
| 28 | Ph | Ph | butoxy-pyridine | HCO | Ac | C | N | —CH2— |

TABLE 9-continued

| Compound No. | R0 | R1 | R2 | R3 | Rd | X | Y | Z |
|---|---|---|---|---|---|---|---|---|
| 28 | Ph | Ph | butoxy-pyridine | HCO | H | C | N | —CH2— |
| 30 | Ph | Ph | butoxy-pyridine | Ac | Ac | C | N | —CH2— |
| 31 | Ph | Ph | butoxy-pyridine | Ac | H | C | N | —CH2— |
| 32 | Ph | Ph | —(CH2)3Ph | acetyl-tetrahydrofuran | Ac | C | N | —CH2— |
| 33 | Ph | Ph | —(CH2)3Ph | acetyl-tetrahydrofuran | H | C | N | —CH2— |
| 34 | Ph | Ph | —(CH2)3Ph | Boc | Ac | C | N | —CH2— |

TABLE 10

| Compound No. | R0 | R1 | R2 | R3 | Rd | X | Y | Z |
|---|---|---|---|---|---|---|---|---|
| 35 | Ph | Ph | butoxy-pyridine | benzyl-methanesulfonamide | Ac | C | N | —CH2— |

TABLE 10-continued

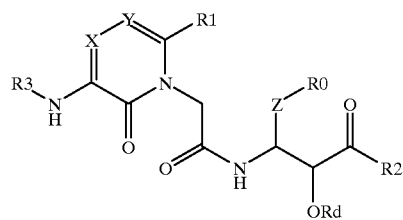

| Compound No. | R0 | R1 | R2 | R3 | Rd | X | Y | Z |
|---|---|---|---|---|---|---|---|---|
| 36 | Ph | Ph |  |  | H | C | N | —CH2— |

The ketone derivatives [compound of formula (XXV)] of oxazolidinone as the intermediate for the compound of formula (III) used in the Examples are shown in Tables 11 and 12.

TABLE 11

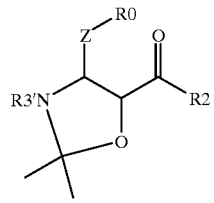

| Intermediate No. | R0 | R2 | R3' | Z |
|---|---|---|---|---|
| 1 | Ph | Me | Boc | —CH2— |
| 2 | Ph | —(CH2)3Ph | Boc | —CH2— |
| 3 | Ph | —(CH2)3Ph | Boc | —CH2— |
| 4 | Ph | n-Bu | Boc | —CH2— |
| 5 | Ph | Ph | Boc | —CH2— |
| 6 | Ph | —(CH2)3COOEt | Boc | —CH2— |
| 7 | 3-F-4-OH—Ph | Me | Boc | —CH2— |
| 8 | 3-F—Ph | Me | Boc | —CH2— |
| 9 | 3-F—Ph | —(CH2)3COOEt | Boc | —CH2— |
| 10 | 3-F—Ph | ![structure](piperazinyl ketone with NMe) | Boc | —CH2— |

TABLE 12

| Intermediate No. | R0 | R2 | R3' | Z |
|---|---|---|---|---|
| 11 | Ph | (butyl-morpholine) | Boc | —CH2— |
| 12 | Ph | (butyl-2-pyridone) | Boc | —CH2— |
| 13 | Ph | (butyloxy-pyridine) | Boc | —CH2— |
| 14 | 4-F—Ph | Me | Boc | —CH2— |
| 15 | 4-Cl—Ph | Me | Boc | —CH2— |
| 16 | 3-Me—Ph | Me | Boc | —CH2— |
| 17 | 3-Cl—Ph | Me | Boc | —CH2— |
| 16 | 2-F—Ph | Me | Boc | —CH2— |

Example 1

Synthesis of 2-(5-t-butyloxycarbonylamino-6-oxo-1,6-dihydro-2-phenyl-1-pyrimidinyl)-N-(2,3-dioxo-1-phenylmethyl) butylacetanlide (Compound No. 37) and 2-(5-amino-6-oxo-1,6-dihydro-2-phenyl-1-pyrimidinyl)-N-(2,3-dioxo-1-phenyl-methyl)butylacetamide hydrochloride (Compound No. 38) was carried out as follows.

(1) (4S,5R)-3-t-butyloxycarbonyl-2,2-dimethyl-5-(1-oxoethyl)-4-phenylmethyloxazolidine (Intermediate No. 1).

(4R,5S)-3-t-butyloxycarbonyl-5-(N-methoxy-N-methyl) carbamoyl-2,2-dimethyl-4-phenylmethyloxazolidine (1.50 g, 3.69 mmol) was dissolved in tetrahydrofuran (40 ml), and a solution of methyl magnesium bromide (0.9 M solution, 4.84 ml, 4.36 mmol) in tetrahydrofuran was added dropwise to it at a temperature of −14° C. for 1 minutes under argon atmosphere. After addition, the reaction solution was stirred at room temperature for 2 hours, and aqueous saturated ammonium chloride was added and the reaction solution was extracted with ethyl acetate. The organic layer was washed successively with saturated aqueous sodium bicarbonate and saturated saline and dried over anhydrous sodium sulfate. The drying agent was removed by filtration, and the filtrate was concentrated under reduced pressure, and the resulting residue was purified by silica gel column chromatography (hexane/ethyl acetate=8/1 to 7/1) whereby the title compound (1.29 g, 98% yield) was obtained.
$^1$H-NMR (CDCl$_3$): 1.15–1.70 (15H, complex), 2.00–2.20 (3H, br. s), 2.70–3.30 (2H, m), 4.16 (1H, br. s), 4.13 –4.14 (1H, m), 7.12–7.39 (5H, m)

The intermediates shown in Tables 11 and 12 were synthesized in the same procedures. The physical properties of the objective compounds are as follows:

Intermediate No. 2: MS;m/z=438 (M+1)
Intermediate No. 3: Ms;m/z=321 (M+1)
Intermediate No. 4: $^1$H-NMR(CDCl$_3$); 0.83 (3H, t, J=7.2 Hz), 1.11–1.33 (2H, m), 1.32–1.57 (2H, m), 1.10–1.60 (6H, m), 1.58 (9H, s), 2.15–2.52 (2H, m), 2.70–3.11 (1H, m), 3.22 (1H, dd, J=2.9, 13.2 Hz), 4.15–4.28 (1H, m), 4.30 –4.48 (1H, m), 7.14 –7.39 (5H, m)
Intermediate No. 5: $^1$H-NMR(CDCl$_3$); 1.29–1.80 (15H, complex), 2.74–3.03 (1H, m), 3.22–3.47 (1H, m), 4.81 (1H, br. d, J=9.7 Hz), 5.01 (1H, br. d, J=14.3 Hz), 7.15–7.89 (10H, complex)
Intermediate No. 6: $^1$H-NMR(CDCl$_3$); 1.23 (3H, t, J=7.1 Hz), 1.41–1.67 (15H, complex), 1.80 (2H, quint, J=7.1 Hz), 2.24 (2H, t, J=7.1 Hz), 2.34–2.73 (2H, m), 2.75–3.12 (1H, m), 3.20 (1H, dd, J=3.3, 13.2 Hz), 4.10 (1H, quint, J=7.1 Hz), 4.18 (1H, br. s), 4.40 (1H, br. s), 7.16–7.36 (5H, m)
Intermediate No. 7: MS; m/z=368 (M+1)
Intermediate No. 8: $^1$H-NMR(CDCl$_3$); 1.12–1.66 (15H, complex), 2.13 (3H, s), 2.70–3.24 (2H, complex), 4.13 (1H, br. s), 4.30–4.53 (1H, m), 6.87–7.06 (3H, complex), 7.20–7.40 (1H, m)
Intermediate No. 9: 1.10–1.63 (15H, complex), 1.24 (3H, t, J=7.1 Hz), 1.83 (2H, quint, J=7.3 Hz), 2.27 (2H, t, J=7.3 Hz), 2.35–3.26 (4H, complex), 4.10 (2H, q, J=7.1 Hz), 4.11–4.19 (1H, m), 4.27–4.55 (1H, m), 6.86–7.06 (3H, complex), 7.19–7.34 (1H, m)
Intermediate No. 10: $^1$H-NMR(CDCl$_3$); 1.10–1.70 (15H, complex), 1.73–1.91 (2H, complex), 2.11–2.70 (11H, complex), 2.74–3.24 (2H, complex), 3.40–3.50 (2H, complex), 3.54–3.65 (2H, complex), 4.10–4.23 (1H, m), 4.25–4.55 (1H, m), 6.86–7.04 (3H, complex), 7.20–7.36 (1H, m)
Intermediate No. 11: $^1$H-NMR(CDCl$_3$); 1.45–1.58 (15H, complex), 1.60–1.75 (2H, complex), 2.18 (2H, br. t), 2.32

(6H, br, t, J=4.8 Hz), 3.14–3.35 (2H, complex), 3.59 (4H, br. s), 4.26 (1H, br. s), 4.42 (1H, br. s), 7.18–7.35 (5H, complex)
Intermediate No. 12: Described below.
Intermediate No. 13: Described below.
Intermediate No. 14: $^1$H-NMR(CDCl$_3$) 1.19–1.57 (1.5H, complex), 2.11 (3H, br. s), 2.70–3.20 (2H, complex), 4.05–4.18 (1H, m), 4.30–4.50 (1H, m), 6.94–7.06 (2H, complex), 7.09–7.29 (3H, complex)
Intermediate No. 15: $^1$H-NMR(CDCl$_3$); 1.18–1.59 (15H, complex), 2.12 (3H, br. s), 2.70–3.21 (2H, complex), 4.09 (1H, br. s), 4.30–4.5 3 (1H, m), 7.09–7.34 (4H, m)
Intermediate No. 16: 1.17–1.6 7 (15H, complex), 2.06 (3H, br. s), 2.32 (3H, s), 2.70–3.07 (1H, m), 3.18 (1H, dd, J=3.0, 13.1 Hz), 4.10–4.27 (1H, m), 4.32–4.54 (1H, m), 6.95–7.13 (3H, complex), 7.13–7.25(1H, m)
Intermediate No. 17: MS; m/z=369 (M+1)
Intermediate No. 18: $^1$H-NMR(CDCl$_3$); 1.53 (9H, s), 2.13 (3H, s), 2.85 (1H, br. s), 3.18 (1H, dd, J=3.2, 13.3 Hz), 4.09–4.17 (1H, m), 4.42 (1H, br. s), 7.21–7.33 (3H, complex), 7.21–7.33 (1H, m)
(2) 2-(5-t-Butyloxycarbonylamino-6-oxo-1,6-dihydro-2-phenyl-1-pyrimidinyl)-N-(2R,3S)-(2-hydroxy3-oxo-1-phenylmethyl)butylacetamide (Compound No. 1).
(4S,5R)-3-t-Butyloxycarbonyl-2,2-dimethyl-5-(1-oxoethyl)-4-phenylmethyloxazolidine (1.29 g, 3.87 mmol) was dissolved in 4 N hydrogen chloride/1,4-dioxane solution (29 ml, 116 mmol), and distilled water (2.9 ml) was added to it and the mixture was stirred at room temperature for 3 hours. The reaction solution was concentrated under reduced pressure, and diethyl ether was added to the resulting residue, and the solid thus precipitated was collected (950 mg). This solid was subjected without further purification to the subsequent condensation reaction.

The solid (950 mg) obtained by the above reaction and 5-t-butyloxycarbonylamino-6-oxo-2-phenyl-1,6-dihydro-1-pyrimidinylacetic acid (1.42 g, 4.14 mmol) were dissolved in a mixed solvent of dimethylformamide (5 ml) and tetrahydrofuran (5 ml), and then 1-(3-dimethylaminopropyl)-3-ethylcarbodiimide hydrochloride (1.03 g, 5.38 mmol), 1-hydroxybenzotriazole.1H$_2$O (825 mg, 5.38 mmol) and 4-methylmorpholine (0.70 ml, 6.37 mmol) were added successively to it in this order under cooling on ice, and the mixture was stirred overnight at room temperature,. The reaction solution was diluted with ethyl acetate and washed successively with 5% aqueous citric acid, saturated aqueous sodium bicarbonate, distilled water and saturated saline. After the organic layer was dried by adding anhydrous sodium sulfate, the drying agent was removed by filtration, and the filtrate was concentrated under reduced pressure. The resulting residue was purified by silica gel column chromatography (chloroform/methanol=60/1 to 30/1), whereby the title compound (1.39 g, 65% yield) was obtained.
$^1$H-NMR (CDCl$_3$): 1.53 (9H, s), 2.06 (3H, s), 2.56–2.81 (2H, s), 3.99 (1H, d, J=4.4 Hz) 4.33 (1H, dd, J=2.5, 4.4 Hz), 4.40 (1H, d, J=15.2 Hz), 4.52 (1H, d, J=15.2 Hz), 4.64 –4.82 (1H, m), 6.67 (1H, d, J=8.8 Hz), 7.05–7.57 (11H, complex), 8.73 (1H, s).
(3) 2-(5-t-Butyloxycarbonylamino-6-oxo-1,6-dihydro-2-phenyl-1-pyrimidinyl)-N-(2,3-dioxo-1-phenylmethyl) butylacetamide (Compound No. 37)

2-(5-t-Butyloxycarbonylamino-6-oxo-1,6-dihydro-2-phenyl-1-pyrimidinyl)-N-(2-hydroxy-3-oxo-1-phenylmethyl)butylacetamide (904.6 mg, 1.74 mmol) was dissolved in dimethylsulfoxide (6 ml), and pyridinium trifluoroacetate (171.3 mg, 890 mmol) and 1-(3-dimethylaminopropyl)-3-ethylcarbodiimide hydrochloride (1.00 g, 5.23 mmol) were added to it in this order and stirred for 6 hours and 20 minutes. Ethyl acetate was added to the reaction solution, followed by washing successively with water and saturated saline. The organic layer was dried over anhydrous sodium sulfate, then the drying agent was removed by filtration, and the filtrate was concentrated under reduced pressure. The resulting residue was purified by silica gel column chromatography (chloroform/methanol=60/1) whereby the title compound (720.4 mg, 80% yield) was obtained.
$^1$H-NMR (CDCl$_3$): 1.54 (9H, s), 2.33 (3H, s), 2.99 (1H, dd, J=8.0, 14.1 Hz), 3.22 (1H, dd, J=5.6, 14.1 Hz), 4.48 (2H, s)H 5.17–5.31 (1 H, m), 6.48 (1H, d, J=6.3 Hz), 6.99–7.53 (11H, complex), 8.71 (1H, s); MS:m/z=519 (M+1)
(4) 2-(5-Amino-6-oxo-1,6-dihydro-2-phenyl-1-pyrimidinyl)-N-(2,3-dioxo-1-phenylmethyl)butylacetamide hydrochloride (Compound No. 38)

2-(5-t-Butyloxycarbonylamino-6-oxo-1,6-dihydro-2-phenyl-1-pyrimidinyl)-N-(2,3-dioxo-1-phenylmethyl)-butylacetamide (623.4 mg, 1.2 mmol) was dissolved in 4 N hydrogen chloride/1,4-dioxane solution (9 ml, 36.2 mmol) and stirred at room temperature for 3 hours. Diethyl ether was added to the reaction solution, and the resulting solid was collected by filtration whereby the title compound (51.8 mg, 9% yield) was obtained.
MS; m/z=419 (M+1)

Example 2

Synthesis of 2-(5-t-butyloxycarbonylamino-6-oxo-2-phenyl-1,6-dihydropyrimidine-1-yl)-N-2,3-dioxo-1-(3-fluoro-4-hydroxyphenylmethyl)butylacetamide (Compound No. 49) was conducted in the following manner.
(1) (2S,3R)-3-Benzyloxycarbonylamino-2-hydroxy-4-(3-fluoro-4-hydroxy)phenylbutyric acid-N,O-dinethylhydroxylamide (2S,3R)-3-Benzyloxycarbonylamino-2-hydroxy-4-(4-hydroxy)phenylbutyric acid-N,O-dimethylhydroxylamide (2.15 g, 5.54 mmol).was dissolved in methylene chloride (37 ml), and tetrafluoroborate acid-N-fluoro-3,5-dichloropyridinium (Onoda Florinate FP-B700, 2.11 g, 8.31 mmol) was added to it and stirred at 50° C. for 2 days under argon atmosphere. The reaction solution was left to be cooled to room temperature, diluted with methylene chloride, and washed successively with 20% aqueous citric acid and saturated aqueous sodium bicarbonate. The organic layer was dried over anhydrous sodium sulfate, then the drying agent was removed by filtration, and the filtrate was concentrated under reduced pressure. The resulting residue was purified by silica gel column chromatography (hexane/ethyl acetate/methanol=10/10/1) whereby the title compound (686.8 mg, 30% yield) was obtained.
$^1$H-NMR (CDCl$_3$): 2.73–2.98 (2H, m) 3.15 (3H, s), 3.46 (3H, s), 3.67 (1H, d, J=5.6 Hz), 4.19 (1H, d, J=5.5 Hz), 4.31–4.47 (1H, m), 4.97–5.12 (3H, complex), 6.77–7.21 (3H, m), 7.22–7.42 (5H, m); MS: m/z=407 (M+1)
(2) (2S,3R)-3-t-Butyloxycarbonylamino-2-hydroxy-4-(3-fluoro-4-hydroxy)phenylbutyric acid -N,O-dimethylhydroxylamide (2S,3R)-3-Benzyloxycarbonylamino-2-hydroxy-4-(3-fluoro-4-hydroxy)phenylbutyric acid-N,O-dimethylhydroxylamide (674.8 mg, 1.66 mmol) was dissolved in methanol (50 ml) and 4 N hydrogen chloride/1,4-dioxane solution (0.42 ml), and palladium black (67 mg) was added to it and stirred overnight in hydrogen atmosphere. After the catalyst was removed by filtration, the reaction solution was concentrated under reduced pressure, and the resulting residue was dissolved in 1,4-dioxane (3.3 ml), and then distilled water (1.6 ml), sodium hydrogen carbonate (168 mg, 1.99 mmol) and di-t-butyl dicarbonate (435 mg, 1.99 mmol) were added to it and stirred a at room temperature for 1 hour. The reaction solution was diluted with ethyl acetate and washed successively with saturated aqueous ammonium chloride and saturated aqueous sodium bicarbonate. The organic layer was dried over anhydrous sodium sulfate, then the drying agent was removed by filtration, and the filtrate was concentrated under reduced pressure. The resulting residue was purified by silica gel column chromatography (hexane/ethyl acetate/methanol= 10/10/1) whereby the title compound (557 mg, 90% yield) was obtained.

$^1$H-NMR (CDCl$_3$): 1.39 (9H, s), 2.72–2.93 (2H, m), 3.17 (3H, s), 3.46 (3H, s), 3.63 (1H, d, J=5.9 Hz), 4.14 (1H, d, J=5.1 Hz), 4.29 –4.46 (1H, m), 5.34 (1H, d, J=3.4 Hz), 6.74–7.19 (3H, m)

(3) (4R,5S)-3-t-Butyloxycarbonyl-5-(N-methoxy-N-methyl)carbamoyl-2,2-dimethyl-4-(3-fluoro-4hydroxphenylmethyl)oxazolidine (2S,3R)-3-t-Butyloxycarbonylamino-2-hydroxy-4-(3-fluoro-4-hydroxy)phenylbutyric acid-N,O-dimethylhydroxylamide (512.1 mg, 1.38 mmol) was dissolved in toluene (5.1 ml), and 2,2-dimethoxypropane (1.69 ml, 13.8 mmol) and p-toluenesulfonic acid.1H$_2$O (26 mg, 0.14 mmol) were added to it and stirred at 80° C. overnight. The reaction solution was diluted with ethyl acetate and washed with saturated aqueous sodium bicarbonate. The organic layer was dried over anhydrous sodium sulfate, then the drying agent was removed by filtration, and the filtrate was concentrated under reduced pressure. The resulting residue was purified by silica gel column chromatography (hexane/ethyl acetate=1/1) whereby the title compound (346 mg, 61% yield) was obtained.

$^1$H-NMR (CDCl$_3$): 1.38–1.68 (15H, complex), 2.55–2.87 (1H, m), 3.02–3.25 (4H, complex), 3.32–3.64 (3H, complex) 4.54 (1H, br. d), 4.64 (1H, br. s), 5.37 (1H, br. s), 6.83–7.04 (3H, m)

(4) (4R,5S)-3-t-Butyloxycarbonyl-5-(1-oxoethyl)-2,2-dimethyl-4-(3-fluoro-4-hydroxyphenyl) methyloxazolidine (Intermediate No. 7).

(4R,5S)-3-t-Butyloxycarbonyl-5-(N-methoxy-N-methyl) carbamoyl-2,2-dimethyl-4-(3-fluoro-4-hydroxyphenyl) methyloxazolidine (424.4 mg, 1.03 mmol) was dissolved in tetrahydrofuran (10 ml) under argon atmosphere and cooled at −30° C. Methyl magnesium bromide (0.9 M tetrahydrofuran solution, 3.43 ml, 3.09 mmol) was added dropwise to this solution. After addition, the temperature was naturally raised to room temperature, and after 30 minutes, it was diluted with ethyl acetate and saturated aqueous ammonium chloride. After the organic layer was splited, it was washed successively with saturated aqueous sodium bicarbonate and saturated saline. The organic layer was dried over anhydrous sodium sulfate, the drying agent was removed by filtration, and the filtrate was concentrated under reduced pressure using an evaporator. The resulting residue was purified by silica gel column chromatography (hexane/ethyl acetate=2/1) whereby the title compound (354.3 mg, 94% yield) was obtained.

MS; m/z=368 (M+1)

(5) 2-(5-t-Butyloxycarbonylamino-6-oxo-2-phenyl-1,6-dihydropyrimidine-1-yl)-N-{(1R, 2S)-2-hydroxy-1-(3-fluoro-4-hydroxyphenyl)methyl-3-oxo}butylacetamide (Compound No. 19).

(4R,5S)-3-t-Butyloxycarbonyl-5-(1-oxoethyl)-2,2-dimethyl-4-(3-fluoro-4-hydroxyphenyl) methyloxazolidine (354.3 mg, 0.96 mmol) was dissolved in 4 N hydrogen chloride/1,4-dioxane (2.4 ml), and distilled water (0.24 ml) was added to it and the mixture was stirred at room temperature for 30 minutes. The reaction solution was concentrated under reduced pressure, and toluene was added to the resulting residue, and the mixture was concentrated again whereby white solid (256.9 mg) was obtained. This compound was subjected without further purification to the subsequent reaction.

The white solid (256.9 mg) obtained by the above reaction and 5-t-butyloxycarbonylamino-6-oxo-2-phenyl-1,6-dihydro-1-pyrimidinylacetic acid (334.4 mg, 0.97 mmol) were dissolved in a mixed solvent of dimethylformamide (1.2 ml) and tetrahydrofuran (1.2 ml), and 1-(3-dimethylaminopropyl)-3-ethylcarbodiimide hydrochloride (243 mg, 1.27 mmol), 1-hydroxybenzotriazole.1H$_2$O (194 ml, 1.27 mmol) and 4-methylmorpholine (0.15 ml, 1.50 mmol) were added successively to it in this order, and the mixture was stirred overnight at room temperature. The reaction solution was diluted with ethyl acetate and washed successively with 20% aqueous citric acid, saturated aqueous sodium bicarbonate, distilled water and saturated saline. After the organic layer was dried by adding anhydrous sodium sulfate, the drying agent was removed by filtration, and the filtrate was concentrated under reduced pressure. The resulting residue was purified by preparative silica gel thin layer chromatography (hexane/ethyl acetate/methanol= 10/10/1), whereby the title compound (112 mg, 21% yield) was obtained.

$^1$H-NMR (CDCl$_3$); 1.53 (9H, m), 2.20 (3H, s), 2.86 (2H, d, J=7.8 Hz), 3.93 (1H, br. s), 4.05 (1H, br. s), 4.31 (1H, d, J=15.4 Hz), 4.41 (1H, d, J=15.2 Hz), 4.62–4.76 (1H, m), 6.45–7.00 (5H, complex), 7.38–7.50 (6H, complex), 8.68 (1H, br. s):MS;m/z=555 (M+1)

(6) 2-(5-t-Butyloxycarbonylamino-6-oxo-2phenyl-1,6-dihydropyrimidine-1-yl)-N-{(1R, 2S )-2-hydroxy-1-(4-acetyloxy-3-fluorophenyl)methyl-3-oxo}butylacetamide (Compound No. 7).

2-(5t -Butyloxycarbonylamino-6-oxo-2-phenyl-1,6-dihydropyrimidine-1-yl)-N-{(1R,2S)-2-hydroxy-1-(3-fluoro-4-hydroxyphenyl)methyl-3-oxo}butylacetamide (105.3 mg, 0.19 mmol) was dissolved in 2-propanol (1.26 ml), and aqueous sodium hydroxide (7.6 mg/1.25 ml) and acetic anhydride (17.9 μl, 0.19 mmol) were added to it at 0° C. After stirring at 0° C. for 10 minutes, acetic anhydride was added to it until the yellow reaction solution turned colorless. This solution was diluted with ethyl acetate and washed successively with saturated aqueous sodium bicarbonate and saturated saline. After the organic layer was dried over anhydrous sodium sulfate, the drying agent was removed by filtration, and the filtrate was concentrated under reduced pressure. The resulting residue was purified by silica gel column chromatography (methylene chloride/methanol=20/1), whereby the title compound (98.4 mg, 87% yield) was obtained.

$^1$H-NMR (CDCl$_3$): 1.53 (9H, m), 2.20 (3H, s), 2.33 (3H, s), 2.95 (2H, d, J=8.0 Hz), 3.83 (1H, br. s) 4.05 (1H, br. d), 4.32–4.57 (1H, m), 4.64–4.79 (1H, m), 6.24 (1H, d, J=9.5 Hz), 6.91–7.13 (3H, m), 7.29 (1H, s), 7.39–7.56 (5H, m), 8.23 (1H, s)

(7) 2-(5-t-Butyloxycarbonylamino-6-oxo-2-phenyl-1,6-dihydropyrimidine-1-yl)-N-{2,3-dioxo-1-(4-acetyloxy-3-fluorophenyl)methyl}butylacetamide (Compound No. 65).

Oxalyl chloride (35 μl) was added to methylene chloride (1.7 ml) at room temperature under argon atmosphere and cooled at −78° C. A mixed solution of dimethylsulfoxide (0.057 ml) and methylene chloride (0.5 ml) was added to this solution, and 15 minutes later, a solution of 2-(5-t- butyloxycarbonylamino-6-oxo-2-phenyl-1,6-dihydro pyrimidine-1-yl)-N-{(1R,2S)-2-hydroxy-1-(4-acetyloxy-3-fluorophenyl)methyl-3-oxo}butylacetamtamide (98.9 mg, 0.17 mmol) in methylene chloride (1.7 ml) was added dropwise to it. After addition, the mixture was stirred for 40 minutes, and triethylamine (0.12 ml) was added to it. The reaction solution was diluted with methylene chloride and washed successively with distilled water and saturated saline. After the organic layer was dried over anhydrous sodium sulfate, the drying agent was removed by filtration, and the filtrate was concentrated under reduced pressure. The resulting residue was purified by silica gel column chromatography (chloroform/methanol=80/1), whereby the title compound (57.8 mg, 59% yield) was obtained.

$^1$H-NMR (CDCl$_3$); 1.53 (9H, s), 2.32 (3H, S) 2.34 (3H, s), 2.55–3.01 (1H, m), 3.08–3.37 (1H, m), 4.12–4.48 (2H, complex), 4.70–5.12 (1H, m), 6.20–6.80 (1H, m) 6.82–7.11 (3H, complex), 7.23–7.58 (6 H, complex), 8.72 (1H, br. s)

(8) 2-(5-t-Butyloxycarbonylamino-6-oxo-2-phenyl-1,6-dihydropyrimidine-1-yl) N-{2,3-dioxo-1-(3-fluoro-4-hydroxyphenyl)methyl}butylacetamide (Compound No. 49).

2-(5-t-Butyloxycarbonylamino-6-oxo-2-phenyl-1,6-dihydropyrimidine-1-yl)-N-{2,3-dioxo-1-(4-acetyloxy-3-fluorophenyl)methyl}butylacetamide (54 mg, 0.091 mmol) was dissolved in methanol (1.3 ml) and water (0.65 ml), and after saturated aqueous sodium bicarbonate (0.65 ml) was added, it was stirred for 1 hour at room temperature. The reaction solution was concentrated under reduced pressure and extracted with ethyl acetate, and the organic layer was washed with saturated saline. The organic layer was dried over anhydrous sodium sulfate, and the drying agent was removed by filtration, and the filtrate was concentrated under reduced pressure. The resulting residue was purified by silica gel column chromatography (methylene chloride/methanol=20/1) whereby the title compound (16.1 mg, 32% yield) was obtained.

$^1$H-NMR (CDCl$_3$): 1.53 (9H, m), 2.34 (3H, s), 2.87 (1H, dd, J=8.1, 14.4 Hz), 3.14 (1H, d d. J=5.2, 14.1 Hz), 4.48 (1H, s), 6.09–5.22 (1H, m), 6.23–6.88 (5H, complex), 7.21–7.56 (6H, complex), 8.60–8.76 (1H, br. s); MS: m/z=5 53 (M+1)

Example 3

Synthesis of 2-(5-t-butyloxycarbonylamino-6-oxo-2-phenyl-1,6-dihydropyrimidine-1-yl) -N-(2-hydroxy-3-oxo-6-phenyl-1-phenylmethyl)hexylacetamide (Compound No. 39) was conducted in the following manner.

(1) (2R,3S)-2-Amino-1,7-diphenyl-3-hydroxy-4-oxoheptane p-toluenesulfonate (p-toluenesulfonic acid salt compound of formula (III) wherein R$^0$=phenyl, R$^2$=phenylpropyl, R$^{3\prime}$=R$_d$=hydrogen, and Z=methylene).

(4R, 5S)-3-t-Butyloxycarbonylamino-5-(1-oxo-3-phenyl) butyl-2,2-dimethyl-4-phenylmethyloxazolidine (758.5mg, 1.73 mmol) was dissolved in methanol (9 ml), and p-toluenesulfonic acid.1H$_2$O (330 mg, 1.73 mmol) was added to it, and the mixture was heated under reflux for 4 hours. The reaction solution was concentrated under reduced pressure, and hexane (10 ml) and diethyl ether (10 ml) were added to the resulting residue. The precipitated solid was collected by filtration whereby the title compound (631.5 mg, 75% yield) was obtained.

$^1$H-NMR (DMSO-d6): 1.72 (2H, quint, J=7.3 Hz), 2.29 (3H, s), 2.59 (2H, overlapped with solvent peak), 2.83–2.92 (2H, complex), 3.50–3.70 (2H, overlapped with solvent peak), 3.85 (1H, br. d), 7.09–7.35 (12H, complex), 7.51 (2H, d, J=8.1 Hz), 7.78–7.88 (2H, br. s)

(2) 2-(5-t-Butyloxycarbonylamino-6-oxo-2-phenyl-1,6-dihydropyrimidine-1-yl)-N-(2-hydroxy-3-oxo-6-phenyl-1-phenylmethyl)hexylacetamide (Compound No. 2).

5-t-Butyloxycarbonylamino-6-oxo-2-phenyl-1,6-dihydro-1-pyrimidinylacetic acid (447 mg, 1.30 mmol) and (2R,3S)-2-amino-1,7-diphenyl-3-hydroxy-4-oxoheptane p-toluenesulfonate (651 mg, 1.30 mmol) were dissolved in a mixed solvent of dimethylformamide (2 ml) and tetrahydrofuran (1 ml) and cooled at 0° C. To this solution were added 1-(3-dimethylaminopropyl)-3-ethylcarbodiimide hydrochloride (248 mg, 1.30 mmol), 1-hydroxybenzotriazole.1H$_2$O (198 mg, 1.30 mmol) and 4-methylmorpholine (0.14 ml, 1.30 mmol) in this order, and while the temperature was naturally raised to room temperature, the mixture was stirred overnights The reaction solution was diluted with ethyl acetate and washed successively with 20% aqueous citric acid, saturated aqueous sodium bicarbonate and saturated saline,. The organic layer was dried by adding anhydrous sodium sulfate, and the drying agent was removed by filtration, and the filtrate was concentrated under reduced pressure. The resulting residue was purified by silica gel column chromatography (hexane/ethyl acetate/methanol=30/10/1) whereby the title compound (439.7 mg, 54% yield) was obtained.

$^1$H-NMR (CDCl$_3$); 1.53 (9H, s), 1.86 (2H, complex), 2.26–2.44 (1H, m), 2.50–2.73 (3H, complex), 2.94 (2H, d, J=7.8 Hz), 3.84 (1H, d, J=3.7 Hz), 3.95 (1 H, br. d), 4.31 (1H, d, J=15.3 Hz), 4.49 (1H, d, J=15.3 Hz), 4.68 (1H, br. dd), 6.39 (1H, d, J=9.2 Hz), 7.06–7.47 (15H, complex, overlapped with solventpeak), 8.73 (1H, br. s)

Example 4

Synthesis of 2-(5-amino-6-oxo-2-phenyl-1,6-dihydropyrimidine-1-yl)-N-{2,3-dioxo-6-(2-oxo-1,2-dihydropyridine-1-yl)-1-phenylmethyl}hexylacetamide hydrochloride (Compound No. 73) was conducted in the following manner.

2-(5-Amino-6-oxo-2-phenyl-1,6-dihydropyrimidine-1-yl)-N-{2,3-dioxo-1-phenylmethyl-6-(2-oxo-1,2-dihydropyridine- 1-yl)}hexylacetamide hydrochloride (Compound No. 73).

2-{(5-t-Butyloxycarbonylamino-2-phenyl-1,6-dihydro-6-oxo)pyrimidine-1-yl}-N-{2,3-dioxo-6-(2-oxo-1,2-dihydropyridine-1-yl)-1-phenylmethyl}hexylacetamide (Compound No. 72, 197 mg, 0.31 mmol) was dissolved in methanol (1 ml), and 4 N hydrogen chloride/1,4-dioxane (2.3 ml) was added to it and the mixture was stirred at room temperature for 2 hours. The reaction solution was concentrated under reduced pressure, and chloroform was added to the resulting residue, and the precipitated solid was collected by filtration whereby the title compound (167 mg, 93% yield) was obtained.

$^1$H-NMR (CD$_3$OD): 1.95–2.21 (2H, complex), 2.53–2.96 (4H, complex), 3.98–4.70 (5H, complex), 6.87–8.09 (14H, complex); MS:m/z=540 (M+1)

Example 5

Synthesis of 2-{5-(3-tetrahydrofuroyl)amino-6-oxo-2-phenyl-1,6-dihydropyrimidine-1-yl}-N-{2,3-dioxo-6-phenyl-1-phenylmethyl}hexylacetamide (Compound No. 81) was conducted in the following manner.

(1) 2-(5-t-Butyloxycarbonylamino-6-oxo-2-phenyl-1,6-dihydropyrimidine-1-yl)-N-{(1R,2S)-2-acetyloxy-3-oxo-6-phenyl-1-phenylmethyl}hexylacetamide (Compound No. 34)

2-(5-t -Butyloxycarbonylamino-6-oxo-2-phenyl-1,6-dihydropyrimidine-1-yl)-N-{(1R,2S)-2-hydroxy-3-oxo-6-phenyl-1-phenylmethyl}hexylacetamide (Compound No. 2) (2.65 g, 4.34 mmol) was dissolved in pyridine (5.5 ml), and acetic anhydride (0.82 ml, 8.68 mmol) was added dropwise to it under cooling on ice. After addition, the mixture was stirred at room temperature for 6 hours. The reaction solution was diluted with ethyl acetate and then washed successively with 10% citric acid, saturated aqueous sodium bicarbonate and saturated saline. The organic layer was dried over anhydrous sodium sulfate, and the drying agent was removed by filtration, and the filtrate was concentrated under reduced pressure. The resulting residue was purified by silica gel column chromatography (chloroform/ethyl acetate=3/1 to 1/1) whereby the title compound was obtained (2.70 g, 95% yield).

$^1$H-NMR (CDCl$_3$): 1.53 (9H, s), 1.74–1.93 (2H, m), 2.19 (3H, s), 2.26–2.59 (4H, complex), 2.81 (1H, dd, J=8.8, 13.5 Hz), 3.12 (1H, dd, J=6.45, 13.5Hz), 4.38 (1H, d, J=15.3 Hz), 4.48 (1H, d, J=15.3 Hz), 4.75 (1H, m), 4.91 (1H, d, J=2.0 Hz), 6.3 4 (1H, d, J=9.2 Hz), 7.09–7.35 (11H, overlapped with solventpeak), 7.35–7.45 (5H, complex), 8.75 (1H, s)

(2) 2-{5-(3-Tetrahydrofuroyl)amino-6-oxo-2-phenyl-1,6-dihydropyrimidine-1-yl}-N-{(1R,2s)-2-acetyloxy-3-oxo-6-phenyl-1-phenylmethyl}hexylacetamide (Compound No. 32)

2-(5-t -Butyloxycarbonylamino-6-oxo-2-phenyl-1,6-dihydropyrimidine-1-yl)-N-{(1R,2S)-2-acetyloxy-3-oxo-6-phenyl-1-phenylmethyl}hexylacetamide (2.69 g, 4.12 mmol) was dissolved in 4 N hydrogen chloride/1,4-dioxane (31 ml) and stirred at room temperature for 3 hours. The reaction solution was concentrated under reduced pressure, and hexane was added to the resulting residue, and the resulting solid (2.39 g) was collected by filtration. This solid was subjected without further purification to the subsequent reaction. 3-Tetrahydrofurancarboxylic acid (0.57 ml, 6.0 mmol) was dissolved in methylene chloride (9 ml), and thionyl chloride (4.38 ml, 60.0 mmol) was added dropwise to it at room temperature in argon atmosphere. After addition, the mixture was stirred for 3 hours at room temperature and then the reaction solution was concentrated under reduced pressure. Methylene chloride (10 ml) was added to the resulting residue and cooled on ice, and the previously obtained solid (2.39 g) and triethylamine (3.12 ml, 22.4 mmol) were successively added to it and stirred overnight at room temperature. The reaction solution was diluted with methylene chloride and washed successively with distilled water and 5% citric acid. The organic layer was dried over anhydrous sodium sulfate, then the drying agent was removed by filtration, and the filtrate was concentrated under reduced pressure. The resulting residue was purified by silica gel column chromatography (chloroform/methanol=30/1) whereby the title compound (2.15 g, 86% yield) was obtained.

$^1$H-NMR (CDCl$_3$): 1.74–1.93 (2H, m) 2.19 (3H, s, overlapped with 2H), (2.35–2.60 (4H, complex), 2.82 (2H, dd, J=9.2, 13.6 Hz), 2.93–3.14 (2H, complex), 3.78–4.05 (4H, complex), 4.46 (2H, s), 4.70–4.84 (1H, m), 4.90 (1H, d, J=1.5 Hz), 6.25 (1H, d, J=9.4 Hz), 7.09–7.32 (11H, complex, overlapped with solvent peak), 7.32–7.51 (5H, complex), 8.13 (1H, s)

(3) 2-{5-(3-Tetrahydrofuroyl)amino-6-oxo-2-phenyl-1,6-dihydropyrimidine-1yl}-N-{(1R,2S)-2-hydroxy-3-oxo-6-phenyl-1-phenylmethyl}hexylacetamide (Compound No. 33)

2-{5-(3-Tetrahydrofuroyl) amino-6-oxo-2-phenyl-1,6-dihydropyrimidine-1-yl}-N-{(1R,2S)-2-acetyloxy-3-oxo-6-phenyl-1-phenylmethyl}hexylacetamide (2.15 g, 3.49 mmol) was dissolved in a mixed solvent of methanol (9 ml) and distilled water (1 ml), and potassium carbonate (2.41 g, 17.5 mmol) was added to it and stirred at room temperature for 1 day. The reaction solution was concentrated under reduced pressure, and ethyl acetate was added to it, followed by washing successively with distilled water and saturated saline. The organic layer was dried over anhydrous sodium sulfate, then the drying agent was removed by filtration, and the filtrate was concentrated under reduced pressure. The resulting residue was purified by silica gel column chromatography (chloroform/methanol=30/1) whereby the title compound (555.6 mg, 28% yield) was obtained.

$^1$H-NMR (CDCl$_3$): 1.86 (2H, quint, J=7.5 Hz), 2.12–2.75 (7H, complex) 2.95 (2H, d, overlapped with 1H), 3.80–4.05 (6H, complex), 4.28–4.51 (2H, m), 4.61–4.78 (1H, m), 6.23 (1H, br. d), 7.01–7.27 (11H, complex, overlapped with solvent peak), 7.28–7.45 (5H, complex), 8.12 (1H, br. s)

(4) 2-{5-(3-Tetrahydrofuroylamino-6-oxo-2-phenyl-1,6-dihydropyrimidine-1-yl}-N-(2,3-dioxo-6-phenyl-1-phenylmethyl)hexylacetamide (Compound No. 81)

2-{5-(3-Tetrahydrofuroyl)amino-6-oxo-2-phenyl-1,6-dihydropyrimidine-1-yl}-N-{(1R,2S)-2-hydroxy-3-oxo-6-phenyl-1-phenylmethyl}hexylacetamide obtained above was subjected to the same procedure as in Example 1(3), so that the title compound was obtained by oxidation reaction of the alcohol corresponding to formula 2.

$^1$H-NMR(CDCl$_3$); 1.91 (1H, quint, J=7.5 Hz), 2.24 (1H, m), 2.54–3.28 (7H, complex), 3.85 (2H, m), 3.99 (2H, d, J=6.6 Hz), 4.45 (2H, s), 5.30 (1H, q, J=6.6 Hz), 6.40 (1H, d, J=6.6 Hz), 6.95–7.08 (2H, complex), 7.08–7.34 (8H, complex), 7.46 (5H, s), 8.12 (1H, s), 9.08 (1H, s)

Example 6

Synthesis of 2-t-Butyloxycarbonylamino-3-oxo-5-phenyl-3,4-dihydripyrazine-4-yl acetic acid as the compound of formula 5 was conducted in the following manner.

(1) 1-Benzyloxycarbonylamino-2,2-dimethyloxy-1-phenylethane

N-Benzyloxycarbonylphenylglycinal (1.38 g, 5.12 mmol) was dissolved in methanol (2.6 ml), and trimethyl orthoformate (1.12 ml, 10.24 mmol) and camphor sulfonic acid (59.5 mg, 0.256 mmol) were added to it and stirred overnight at room temperature. The reaction solution was concentrated under reduced pressure, and the resulting residue was purified by column chromatography on alumina (50 g alumina, hexane/ethyl acetate=2/1) whereby the title compound (1.21 g, 77% yield) was obtained.

$^1$H-NMR (CDCl$_3$): 3.35 (3H, s), 3.41 (3H, s), 4.40 (1H, d, J=4.4 Hz), 4.80–4.96 (1H, m), 5.07 (1H, d, J=1.1 Hz), 5.53–5.74 (1H, m); MS: m/z=316 (M+1)

(2) 2,2-Dimethyloxy-1-phenylethylamine hydrochloride

1-Benzyloxycarbonylamino-2,2-dimethyloxy-1-phenylethane (1.21 g, 3.84 mmol) was dissolved in methanol (38.4ml), and 4 N hydrogen chloride/1,4-dioxane (0.96 ml, 3.84 mmol) and palladium black (121 mg) were added to it and hydrogenolyzed overnight at room temperature in hydrogen atmosphere. After the palladium black was removed by filtration, the filtrate was concentrated under reduced pressure, and methylene chloride and diethyl ether were added to the resulting residue. The precipitated solid was collected by filtration whereby the title compound (760.3 mg, 91% yield) was obtained.

$^1$H-NMR (CDCl$_3$): 3.25 (3H s), 3.40 (3H$_3$ s)H 4.17–4.34 (1H, m), 4.78 (1H, d, J=6.4 Hz), 7.27–7.57 (5H, m), 8.86 (2H, br. s)

(3) N-{(N-t-Butyloxycarbonyl-2-ethoxycarbonyl)glycyl}-2,2-dimethyloxy-1-phenylethylamine (N-t-Butyloxycarbonyl-2-ethoxycarbonyl)glycine (7.19 g, 29.1 mmol) and 2,2-dimethyloxy-1-phenylethylamine hydrochloride (6.33 g, 29.1 mmol) were dissolved in a mixed solvent of dimethylformamide (72 ml) and tetrahydrofuran (72 ml), and to this solution were added 1-hydroxybenzotriazole.1H$_2$O (5.11 g, 37.8 mmol), 1-(3-dimethylaminopropyl)-3-ethylcarbodiimide hydrochloride (7.25 g, 37.8 mmol), and 4-methylmorpholine (4.52 ml, 44.8 mmol) in this order, and the mixture was stirred overnight at room temperature. The reaction solution was diluted with ethyl acetate and washed successively with distilled water and saturated saline. After the organic layer was dried over anhydrous sodium sulfate, the drying agent was removed by filtration, and the filtrate was concentrated under reduced pressure. Toluen was added to the resultant residue, and then azeotropic distillation was carried out. Thereafter, the resulting residue was purified by silica gel column chromatography (hexane/ethyl acetate=1/1) whereby the title compound (10.6 g, 93% yield) was obtained.

$^1$H-NMR (CDCl$_3$): 1.20–1.37 (3 H, m), 1.43–1.48 (9H, m), 3.34–3.43 (6H, m), 4.06–4.35 (2H, m), 4.43 (1H, d, J=3.4 Hz), 4.81–4.93 (1H, m), 5.03–5.14 (1H, m), 5.68–5.82 (1H, m), 7.24–7.38 (5H, complex); MS:m/z=411 (M+1)

(4) 2-Ethyloxycarbonyl-3-hydroxy-5-phenylpyrazine.

N-{(N-t-butyloxycarbonyl-2-ethbxycarbonyl) glycyl}-2,2-dimethyloxy-1-phenylethylamine (10.6 g, 25.7 mmol) was dissolved in trifluoroacetic acid (100 ml) and stirred overnight at room temperature. The residue obtained by concentrating the reaction solution under reduced pressure was dissolved in acetonitrile (130 ml) and further stirred overnight at room temperature. The residue obtained by concentrating the reaction solution under reduced pressure was purified by silica gel column chromatography (hexane/ethyl acetate/methanol=10/10/1) whereby the title compound (1.93 g, 31% yield) was obtained.

$^1$H-NMR (CDCl$_3$): 1.51 (3H, t, J=7.1 Hz), 4.58 (2H, q, J=7.1 Hz), 7.48–7.58 (3H, m), 8.08–8.19 (2H, m), 8.78 (1H, s); MS:m/z=245 (M+1)

(5) 4-Allyl-2-ethyloxycarbonyl-3-oxo-5-phenyl-3,4-dihydropyrazine

2-Ethyloxycarbonyl-3-hydroxy-5-phenylpyrazine (214.4 mg, 0.88 mmol) was dissolved in dimethylformamide (2.1 ml), and sodium hydride (60% in oil, 42.1 g, 1.05 mmol) was added to it under cooling on ice and stirred for 30 minutes. After allyl bromide (0.11 ml, 1.32 mmol was added, the mixture was stirred at room temperature for 1 hour and then at 80° C. for 1 hour. The reaction solution was left to be cooled to room temperature, thereafter the reaction was terminated by adding distilled water, and the product was extracted twice with ethyl acetate. The organic layer was dried over anhydrous sodium sulfate, and the drying agent was removed by filtration, and the filtrate was concentrated under reduced pressure. The resulting residue was purified by silica gel column chromatography (hexane/ethyl acetate=2/1) whereby the title compound was obtained (24 mg, 9.6% yield).

$^1$H-NMR (CDCl$_3$): 1.44 (3H, t, J=7.1 Hz), 4.46 (2H, d, J=7.1 Hz), 4.49–4.56 (2H, m), 4.88–5.01 (1H, m), 5.15–5.24 (1H, m), 5.76–5.96 (1H, m), 7.35–7.61 (6H, complex)

(6) 4-Allyl-2-t-butyloxycarbonylamino-3-oxo-5-phenyl-3,4-dihydropyrazine

4-Allyl-2-ethyloxycarbonyl-3-oxo-5-phenyl-3,4-dihydro pyrazine (1.09 g, 3.85 mmol) was dissolved in a mixed solvent consisting of methanol (25 ml) and tetrahydrofuran (10 ml), and 1 N aqueous sodium hydroxide (4.2 ml, 4.20 mmol) was added to it under cooling on ice and the mixture was stirred at room temperature for 2 hours. The reaction solution was neutralized with hydrochloric acid and concentrated under reduced pressure. After distilled water was added to the resulting residue, it was extracted with methylene chloride. The organic layer was dried over anhydrous magnesium sulfate, and the drying agent was removed by filtration, and the filtrate was concentrated under reduced pressure whereby 1.02 g solid was obtained.

The resulting solid (1.02 g) was dissolved in t-butyl alcohol (10.2 ml), 1,4-dioxane (2.6 ml) and triethylamine (1.11 ml), and diphenylphosphoryl azide (0.86 ml, 3.98 mmol) was added to it at room temperature in argon atmosphere and stirred under heating at 90° C. for 8 hours. After left to be cooled to room temperature, distilled water was added to the reaction solution, and the product was extracted with ethyl acetate. The organic layer was dried over anhydrous magnesium sulfate, then the drying agent was removed by filtration, and the filtrate was concentrated under reduced pressure. The resulting residue was purified by silica gel column chromatography (hexane/ethyl acetate=1/1) whereby the title compound (850 mg, 68% yield in the 2 steps) was obtained.

$^1$H-NMR (CDCl$_3$): 1.54 (9H, s), 4.45–4.52 (2H, m), 4.83–4.97 (1H, m), 5.13–5.22 (1H, m), 5.67–5.88 (1H, m), 7.27 (1H, m), 7.30–7.55 (5H, complex), 8.32 (1H, s); MS:m/z=328 (M+1)

(7) 2-t-Butyloxycarbonylamino-3-oxo-5-phenyl-4-(2,3-dihydroxy)propyl-3,4-dihydropyrazine 4-Allyl-2-t-butyloxycarbonylamino-3-oxo-5-phenyl-3,4-dihydropyrazine (850 mg, 2.60 mmol) was dissolved in tetrahydrofuran (10.4 ml), and 4-methylmorpholine N-oxide (1.22 ml, 5.19 mmol) and 4% aqueous osmium tetroxide (0.83 mol. 0.13 mmol) was added to it, and the mixture was stirred overnight at room temperature. The reaction solution was diluted with ethyl acetate and then washed successively with saturated aqueous sodium thiosulfate, distilled water and saturated saline. The organic layer was dried over anhydrous magnesium sulfate, and the drying agent was removed by filtration, and the filtrate was concentrated under reduced pressure. The resulting residue was purified by silica gel column chromatography (chloroform/methanol=50/1) whereby title compound (750 mg, 80% yield) was obtained.

$^1$H-NMR (CDCl$_3$): 1.55 (9H, s), 2.66 (1H, dd, J=5.7, 7.7 Hz), 3.26–3.42 (1H, m, overlapped with 1H), 3.68–3.85 (1H, m), 4.06 (2H, d, J=6.2 Hz), 7.14 (1H, s), 7.29–7.53 (5H, complex), 8.29 (1H, s); MS:m/z=362 (M+1)

(8) 2-t-Butyloxycarbonylamino-1,2,3-oxo-5-phenyl-3,4-dihydropyrazine-4-yl acid 2-t-Butyloxycarbonylamino-3-oxo-5-phenyl-4-(2,3-dihydroxy)propyl-3,4-dihydropyrazine (750 mg, 2.01 mmol) was dissolved in tetrahydrofuran (10 ml), and aqueous sodium periodate (solution of 533 mg (2.49 mmol) sodium periodate in 6.7 ml distilled water) was added to it, and the mixture was -stirred at room temperature for 4 hours. The tetrahydrofuran was distilled off under reduced pressure and then the reaction solution was diluted with ethyl acetate and then washed successively with distilled water and saturated saline. After the organic layer was dried over anhydrous magnesium sulfate, and the drying agent was removed by filtration, and the filtrate was concentrated under reduced pressure to give a colorless foamed substance (710.7 mg).

The resulting substance (710 mg) was dissolved in t-butanol (10.8 ml), followed by successively adding 2-methyl-2-butene (1.01 ml, 9.50 mmol), aqueous sodium hydrogen phosphate {solution of 306.3 mg (2.16 mmol) sodium hydrogen phosphate in 3 ml distilled water} and aqueous sodium chlorite (solution of 683.1 mg (7.56 mmol) sodium chlorite in 6.8 ml distilled water), and the mixture was stirred overnight at room temperature. The reaction solution was diluted with diethyl ether and then extracted 3 times with saturated aqueous sodium bicarbonate. The aqueous layer was acidified with anhydrous citric acid and extracted 3 times with ethyl acetate. The organic layer was dried over anhydrous sodium sulfate, and then the drying agent was removed by filtration, and the filtrate was concentrated under reduced pressure whereby the title compound (502.5 mg, 70% yield in the 2 steps) was obtained.
$^1$H-NMR (CDCl$_3$): 1.53 (9H, s), 4.53 (2H, s), 7.15 (1H, s), 7.30–7.54 (5H, complex), 8.14–8.34 (1H, m); MS:m/z=346 (M+1)

Examples 7 to 18

5-t-Butyloxycarbonylamino-6-oxo-2-phenyl-1,6-dihydro-1-pyrimidinylacetic acid as the compound of formula (V) and the compound of formula (III) wherein $R^{3'}$ is t-butyloxycarbonyl, Z is methylene, and $R^0$ and $R^2$ are the groups defined below were condensed in the same manner as described in Example 1(1) to (2), whereby the compounds of formula (II) wherein $R^1$ is phenyl, $R^3$ is t-butyloxycarbonyl, X is carbon, Y is nitrogen, Z is methylene, $R^0$ and $R^2$ are the groups defined below were synthesized.

The compounds of formula (III) are formed in the reaction system from their corresponding oxazolidine derivatives.

The physical properties of the objective compounds of formula (II) are as follows.

Example 7: $R^0$=phenyl, $R^2$=butyl (Compound No. 4)

$^1$H-NMR (CDCl$_3$); 0.85 (3H, t, J=7.1 Hz), 1.14–1.35 (2H, m), 1.42–1.58 (2H, m), 1.53 (9H, s), 2.33 (1H, dt, J=7.4, 17.4 Hz), 2.58 (1H, dt, J=7.4, 17, 4 Hz), 2.95 (2H, d, J=8.0 Hz), 3.87 (1H, d, J=3.6 Hz), 4.03 (1H, dd, J=1.1, 3.5 Hz), 4.31 (1H, d, J=15.3 Hz), 4.47 (1H, d, J=15.3 Hz), 4.70 (1H, ddt, J=1.4, 8.1, 8.4 Hz), 6.40 (1H, d, J=9.5 Hz), 7.15–7.55 (1H, complex), 8.72 (1H, s)

Example 8: $R^0$=$R^2$=phenyl (Compound No. 5)

$^1$H-NMR (CDCl$_3$); 1.53 (9H, s), 2.98 (1H, dd, J=9.5, 13.1 Hz), 3.08 (1H, dd, J=6.0, 13.1 Hz), 3.95 (1H, d, J=4.8 Hz). 4.32–4.89 (3H, complex), 4.97 (1H, d, J=3.7 Hz), 6.36 (1H, d, J=9.2 Hz), 6.80–6.91 (1H, m), 7.03–7.13 (1H, m), 7.18–7.69 (14H, complex), 7.98–8.07 (1H, m), 8.65–8.77 (1H, m)

Example 9; $R^0$=phenyl, $R^2$=3-ethoxycarbonylpropyl (Compound No. 6)

$^1$H-NMR (CDCl$_3$); 1.21 (3H, t, J=7.1 Hz), 1.53 (9H, s), 1.87 (2H, quint, J=7.0 Hz), 2.28 (1H, t, J=7.0 Hz), 2.29 (1H, t, J=7.4 Hz), 2.40–2.49 (1H, t, J=7.4 Hz), 2.67–2.76 (1H, t, J=7.1 Hz), 2.96 (2H, d, J=7.8 Hz), 3.70–4.20 (1H, br, s), 4.04 (1H, br. s), 4.08 (2H, q, J=7.1 Hz), 4.34,(1H, d, J=15.3 Hz), 4.44 (1H, d, J=15.3 Hz), 4.60–4.76 (1H, m), 6.42 (1H, d, J=9.4 Hz), 6.87–7.07 (3H, m), 7.19–7.33 (2H, m), 7.39–7.50 (5H, complex), 8.72 (1H, s)

Example 10: $R^0$=3-fluorophenyl, $R^2$=3-ethoxycarbonylpropyl (Compound No. 9)

$^1$H-NMR (CDCl$_3$); 1.21 (3H, t, J=7.1 Hz), 1.53 (9H, s), 1.87 (2H, quint, J=17.1 Hz), 2.28 (1H, t, J=7.0 Hz), 2.29 (1H, t, J=7.4 Hz), 2.49 (1H, t, J=7.4 Hz), 2.67 (1H, t, J=7.0 Hz), 2.96 (2H; d, J=7.8 Hz), 3.70–4.20 (1H, br. s), 4.04 (1H, br. s), 4.08 (2H, q, J=7.1 Hz), 4.34 (1H, D, J=15.3 Hz), 4.44 (1H, d, J=15.3 Hz), 4.60–4.76 (1H, m), 6.42 (1H, d, J=9.4 Hz), 6.87–7.07 (3H, m), 7.19–7.33 (2H, m), 7.39–7.50 (2H, complex), 8.72 (1H, s): IR (KBr); 3700–2800, 1720, 1677, 1512, 1492, 1370, 1252, 1221, 1154, 1087 cm-1.

Example 11: $R^0$=phenyl, $R^2$=2-phenylethyl (Compound No. 3)

MS; m/z=548 (M+1)

Example 12

Synthesis of 2-(5-t-butyloxycarbonylamino-6-oxo-2-phenyl-1,6-dihydropyrimidine-1-yl)-N-{2-hydroxy-3-oxo-6-(2-oxo-1,2-dihydropyridine-1-yl)-1-phenylmethyl}hexylacetamide (Compound No. 12)

(1) (4R,5S)-3-(N-t-butyloxycarbonyl)-2,2-dimethyl-5-methoxycarbonyl-4-phenylmethyloxazolidine Methyl (2S,3R)-3-t-butyloxycarbonylamino-2-hydroxy-4-phenylbutyrate (43 g, 0.14 mol) was suspended in 2,2-dimethoxypropane (510 ml), and p-toluenesulfonic acid.1H$_2$O (2.6 g, 0.015 mol) was added to it, and then the mixture was heated under argon atmosphere, and the reaction solvent was distilled off gradually. Heating was stopped 6 hours later when the solvent was absent by distilling it off, and it was left to be cooled to room temperature. The residue was dissolved in ethyl acetate and washed successively with saturated aqueous sodium bicarbonate and saturated saline. The organic layer was dried over anhydrous sodium sulfate and concentrated under reduced pressure, and then the resulting residue was purified by silica gel column chromatography (hexane/ethyl acetate=9/1) whereby the title compound (43 g, 88% yield) was obtained.
$^1$H-NMR (CDCl$_3$); 1.28–1.80 (15H, complex), 2.72– 3.08 (1H, m), 2.86 (1H, br. s), 3.25 (2H br. d, J=6.3 Hz), 3.67 (3H, s), 4.37 (1H, d, J=4.0 Hz), 4.50 (1H, br. d, J=13.5 Hz), 7.10–7.40 (5H, m)

(2) (4R,5S)-3-(N-t-Butyloxycarbonyl)-2,2-dimethyl-5-hydroxymethyloxazolidine (4R,5S)-3-(N-t-Butyloxycarbonyl)-2,2-dimethyl-5-methoxycarbonyl-4-phenylmethyloxazolidine (43 g, 0.12 mol) was dissolved in tetrahydrofuran (610 ml), and lithium aluminum hydride (7.0 g, 0.18 mol) was added to it under cooling on ice and stirred for 30 minutes. Distilled water (10 ml), 3 N aqueous sodium hydroxide (10 ml) and distilled water (30 ml) were added dropwise to it in this order, and then the precipitated solid was removed by filtration through Celite and washed with methylene chloride. The organic layer was collected, washed with distilled water and saturated saline, and then dried over anhydrous sodium sulfate. The organic layer was concentrated under reduced pressure, and the resulting residue was purified by silica gel column chromatography (hexane/ethyl acetate=4/1) whereby the title compound (35 g, 88% yield) was obtained.
$^1$H-NMR (CDCl$_3$); 1.21–1.73 (15H, complex), 1.80 (1H, t, J=6.3 Hz), 2.78 (1H, br. s), 3.14–3.43 (2H, complex), 3.33 (1H, dd, J=3.2, 13.0 Hz), 3.83– 4.08 (2H, complex), 7.14–7.36 (5H, m)

(3) (4R,5S)-3-(N-t-Butyloxycarbonyl)-2,2-dimethyl-5-formyl-4-phenylmethyloxazolidine Methylene chloride (530 ml) and distilled water (53 ml) were added to (4R,5S)-3-(N-t-butyloxycarbonyl)-2,2-dimethyl-5-hydroxymethyloxazolidine (35 g, 0.11 mol), 2,2,6,6-tetramethyl-1-piperidinyloxy free radical (185 mg, 0.01 mmol), sodium bromide (12 g, 0.12 mol) and sodium hydrogen carbonate (26 g, 0.31 mol) to make a 2-phase system. After the reaction system was cooled on ice, 0.62 M aqueous sodium hypochlorite (200 ml, 0.12 mol) was added dropwise to it under vigorous stirring. After addition, the reaction solution was stirred for 10 minutes and then washed successively with 10% aqueous potassium hydrogen sulfate containing 0.6% aqueous potassium iodide, 10% aqueous sodium thiosulfate, and saturated saline. The organic layer was dried over anhydrous sodium sulfate and then concentrated under reduced pressure, and the resulting residue was purified by silica gel column chromatography (hexane/ethyl acetate=4/1) whereby the title compound (21 g, 62% yield) was obtained.

¹H-NMR (CDCl₃); 1.10–1.80 (15H, complex), 2.62–3.45 (2H, m), 4.05–4.28 (1H, m), 4.28–4.60 (1H, br. d, J=4.1 Hz), 6.95–7.48 (5H, m), 9.64 (1H, s)

(4) (4R,5S)-3-(N-t-Butyloxycarbonyl)-5-(1-hydroxy-4-phenylmethyloxybutyl)-4-phenylmethyloxazolidine (4R,5S)-3-(N-t-Butyloxycarbonyl)-2,2-dimethyl-5-formyl-4-phenylmethyloxazolidine (19 g, 0.6 mol) was dissolved in tetrahydrofuran and cooled to −30° C., and then 0.63 M 3-phenylmethyloxypropyl magnesium bromide in tetrahydrofuran (140 ml, 0.8 mol) was added dropwise to it. After addition, the cooling bath was removed and the mixture was stirred at room temperature for 2 hours. After saturated aqueous ammonium chloride was added to the reaction solution, the precipitated solid was removed by filtration through Celite. After ethyl acetate was added to the filtrate, it was washed with saturated saline. The organic layer was dried over anhydrous sodium sulfate and then concentrated under reduced pressure, and the resulting residue was purified by silica gel column chromatography (hexane/ethyl acetate=4/1), whereby the title compound (28 g, 90% yield) was obtained. This compound is present as a mixture of stereoisomers due to the configuration of the hydroxyl group, and a spectrum was taken of this mixture. The signals of only the major isomer are as follows.

¹H-NMR (CDCl₃, major isomer); 0.97–1.80 (17H, complex), 2.51 (1H, d, J=4.8 Hz), 2.60–3.00 (1H, br. s), 3.15 (1H, dd, J=3.0, 13.1 Hz), 3.23–3.56 (4H, complex), 3.66–3.85 (1H, m), 4.12– 4.26 (1H, m), 4.46 (2H, s), 7.12–7.40 (10H, complex): MS; m/z=470 (M+1)

(5) (4R,5S)-5-(1-t-Butyldimethylsilyloxy-4-phenylmethyloxybutyl)-3-(N-t-butyloxycarbonyl)-2,2-dimethyl-4-phenylmethyloxazolidine (4R,5S)-3-(N-t-Butyloxycarbonyl)-5-(1-hydroxy-4-phenylmethyloxybutyl)-4-phenylmethyloxazolidine (28 g, 0.06 mol) and imidazole (10 g, 0.15 mol) were dissolved in N,N-dimethylformamide (120 ml), and t-butyldimethylsilyl chloride (12 g, 0.08 mol) was added to it under cooling on ice and then stirred overnight at room temperature. Diethyl ether was added to the reaction solution, followed by washing successively with distilled water and saturated saline. The organic layer was dried over anhydrous sodium sulfate and concentrated under reduced pressure, and the resulting residue was purified by silica gel column chromatography (hexane/ethyl acetate=9/1), whereby the title compound (26 g, 72% yield) was obtained. This compound is present as a mixture of stereoisomers due to the configuration of the t-butyldimethylsilyoxy group, and a spectrum was taken of this mixture. The signals of only the major isomer are as follows.

¹H-NMR (CDCl₃, major isomer): 0.02 (6H, s), 0.77 (9H, s), 1.35–1.80 (19H, complex), 2.88 (1H, dd, J=9.4, 12.8 Hz), 3.04 (1H, dd, J=3.6, 12.8 Hz), 3.45 (1H, t, J=6.2 Hz), 3.63–3.76 (1H, m), 3.76–3.94 (1H, m), 4.11–4.22 (1H, m), 4.52 (2H, s), 7.16–7.40 (10H complex)

(6) (4R,5S)-5-(1-t-Butyldimethylsilyloxy-4-hydroxybutyl-3-(N-t-butyloxycarbonyl)-2,2-dimethyl-4-phenylmethyl oxazolidine (4R,5S)-5-(1-t-Butyldimethylsilyloxy-4-phenylmethyloxybutyl)-3-(N-t-butyloxycarbonyl)-2,2-dimethyl-4-phenylmethyloxazolidine (32 g, 0.54 mol) was dissolved in methanol (270 ml), and after palladium black (1.6 g) was added to it, the mixture was stirred at room temperature for 4 hours under hydrogen atmosphere. The palladium black was removed by filtration, and then the filtrate was concentrated under reduced pressure, and the resulting residue was purified by silica gel column chromatography (hexane/ethyl acetate=14/1) whereby the title compound (26 g, 98% yield) was obtained. This compound is present as a mixture of stereoisomers due to the configuration of the t-butyldimethylsilyloxy group, and a spectrum was taken of this mixture. The signals of only the major isomer are as follows.

¹H-NMR (CDCl₃, major isomer):0.02 (6H, s), 0.76 (9H, s), 1.38–1.85 (19H, complex), 2.86 (1H, dd, J=9.3, 12.9 Hz), 3.04 (1H, dd, J=3.9, 12.9 Hz), 3.25–3.78 (3H, complex), 3.85–4.00 (1H, m), 4.08–4.21 (1 H, m), 7.1 5–7.3 4 (5H, m)

(7) (4R,5S)-5-{4-Bromo-1-(t-butyldimethylsilyloxy)butyl}-3-(N-t-butyloxycarbonyl)-2,2-dimethyl-4-phenylmethyloxazolidine (4R,5S)-5-(1-t-Butyldimethylsilyloxy-4-hydroxybutyl)-3-(N-t-butyloxycarbonyl)-2,2-dimethyl-4-phenylmethyloxazolidine (26 g, 0.052 mol) was dissolved in toluene (50 ml), and after triphenyl phosphine (14 g, 0.052 mol) and N-bromosuccinimide (9.3 g, 0.052 mol) were added to it under cooling on ice, the temperature was raised and the mixture was stirred at room temperature for 2 hours. The precipitated solids were removed by filtration through Celite, and the filtrate was washed successively with 5% aqueous sodium thiosulfate, 1 N aqueous sodium hydroxide, and saturated saline. The organic layer was dried over anhydrous sodium sulfate and then concentrated under reduced pressure, and hexane was added to the resulting residue, and the precipitated solids were removed by filtration, and the filtrate was concentrated again under reduced pressure. The resulting residue was purified by silica gel column chromatography (hexane/ethyl acetate=14/1) where by the title compound (24 g, 82% yield) was obtained. This compound is present as a mixture of stereoisomers due to the configuration of the t-butyldimetylsilyloxy group, and a spectrum was taken of this mixture. The signals of only the major isomer are as follows.

¹H-NMR (CDCl₃, major isomer): 0.02 (6H, s), 0. 76 (9H, s), 1.40–2.00 (19H, complex), 2.85 (1H, dd, J=9.1, 13.0 Hz), 3.05 (1H, dd, J=3.9, 13.0 Hz), 3.38 (2H, m), 3.78 (1H, br. d, J=8.5 Hz), 4.07–4.21 (1H, m), 7.11–7.41 (5H, m);Ms:m/z= 556 (M+1)

(8) (4R,5S)-5-{1-t-Butyldimethylsilyloxy-4-(2-oxo-1,2-dihydropyridine-1-yl)butyl}-3-(N-t-butyloxycarbonyl)-2,2-dimethyl-4-phenylmethyloxazolidine Sodium hydride (0.72 g, 0.018 mol) was suspended in N,N-dimethylformamide (45 ml), and a solution of 2-hydroxypyridine (1.7 g, 0.018 mol) in N,N-dimethylformamide (15 ml) was added dropwise to it under cooling on ice. After addition, the mixture was stirred at room temperature for 1 hour, and the reaction system was cooled again on ice. A solution of (4R,5S)-5-{4-Bromo-1-(t-butyldimethylsilyloxy)butyl}-3-(N-t-butyloxycarbonyl)-2,2-dimethyl-4-phenylmethyloxazolidine (5 g, 9 mmol) in N,N-dimethylformamide (30 ml) was added dropwise to it, and the mixture was stirred overnight at room temperature. The reaction solution was diluted with ethyl acetate and washed successively with distilled water, 10% aqueous citric acid and saturated saline. The organic layer was dried over anhydrous sodium sulfate and then concentrated under reduced pressure, and the resulting residue was purified by silica gel column chromatography (hexane/ethyl acetate=7/1) whereby the title compound (3.7 g, 71% yield) was obtained.

¹H-NMR (CDCl₃); 0.04 (6H, s) 0.71 (9H, br. s), 1.34–1.89 (19H, complex), 2.73–2.92 (1H, m), 3.01 (1H, dd, J=3.6, 12.9 Hz), 3.55–3.97 (3H, complex), 4.01–4.16 (1H, m), 6.13 (1H, dt, J=1.3, 6.7 Hz), 6.50–6.59 (1H, m), 7.10–7.35 (7H, complex):IR (K Br);2930, 1690, 1660, 1590, 1535, 1455, 1380, 1250, 1170, 1080, 1030 cm-1

As the by product, (4R,5S)-5-{1-t-butyldimethylsilyloxy-4-(2-pyridyloxy) butyl}-3-(N-t-butyloxycarbonyl)-2,2-dimethyl-4-phenylmethyloxazolidine (1.3 g, 24% yield) was obtained.

$^1$H-NMR (CDCl$_3$); 0.00 (6H, s, overlapped with internal standard peak), 0.64–0.97 (9H, m), 1.38–1.90 (19H, complex), 2.77–3.16 (2H, m), 3.66–4.34 (5H, complex), 6.70 (1H, d, J=8.4 Hz), 6.83 (1H, ddd, J=1.9, 5.1, 8.4 Hz), 7.09–7.34 (5H, m), 7.54 (1H, ddd, J=0.9, 7.0, 8.4 Hz), 8.13 (1H, ddd, J=0.9, 1.9, 5.1 Hz)

(9) (4R,5S)-5-{1-oxo-4-(2-oxo-1,2-dihydropyridine-1-yl)butyl}-3-(N-t-butyloxycarbonyl)-2,2-dimethyl-4-phenylmethyloxazolidine (Intermediate No. 12)

(4R,5S)-5-{1-t-Butyldimethylsilyloxy-4-(2-oxo-1,2-dihydropyridine-1-yl)butyl}-3-(N-t-butyloxycarbonyl)-2,2-dimethyl-4-phenylmethyloxazolidine (3.8 g, 6.6 mmol) was dissolved in 1.0 M tetrabutylammonium fluoride in tetrahydrofuran (10 ml) under cooling on ice and stirred for 4 hours. The reaction solution was diluted with ethyl acetate and washed successively with 10% aqueous citric acid and saturated saline. The organic layer was dried over anhydrous sodium sulfate and then concentrated under reduced pressure, and the resulting residue was purified by silica gel column chromatography to give a crude product.

Oxalyl chloride (1.5 ml, 17 mmol) was added to methylene chloride (2.4 ml) under argon atmosphere and cooled at −60° C. A mixture of dimethylsulfoxide (2.4 ml, 34 mmol) and methylene chloride (2.4 ml) was added dropwise to it. After addition, the mixture was stirred for 15 minutes, and then a solution of the above crude product in methylene chloride (20 ml) was added dropwise to it. After addition, the mixture was stirred for 1 hour, and the reaction temperature was raised to −40° C., and then triethylamine (9.5 ml, 68 mmol) was added to it. The reaction solution was diluted with methylene chloride and washed with distilled water. The organic layer was dried over anhydrous sodium sulfate and then concentrated under reduced pressure, and the resulting residue was purified by silica gel column chromatography (chloroform/methanol=30/1) whereby the title compound (2.6 g, 89% yield) was obtained.

$^1$H-NMR (CDCl$_3$); 1.17–1.65 (15H, complex), 1.92 (2H, dq, J=2.2, 7.3 Hz), 2.25–2.71 (2H, m), 2.73–3.12 (1H, m), 3.21 (1H, dd, J=3.0, 13.3 Hz), 3.85 (2H, dt, J=2.2, 7.3 Hz), 4.21 (1H, br. s), 4.30–4.50 (1H, m), 6.13 (1H, dt, J=1.3, 6.7 Hz), 6.52 (1H, d, J=9.2 Hz), 7.13–7.45 (7H, complex)

(10) 2-(5-t-Butyloxycarbonylamino-6-oxo-2-phenyl-1,6-dihydropyrimidine-1-yl)-N-{2-hydroxy-3-oxo-6-(2-oxo-1,2-dihydropyridine-1-yl)-1-phenylmethyl}hexylacetamide, (Compound No. 12)

(4R,5S)-5-{1-oxo-4-(2-oxo-1,2-dihydropyridine-1-yl)butyl}-3-(N-t-butyloxycarbonyl)-2,2-dimethyl-4-phenylmethyloxazolidine (2.6 g, 5.8 mmol) was dissolved in methanol (28 ml), and p-toluenesulfonic acid.1H$_2$O (2.4 g, 13 mmol) was added to it, and the mixture was heated under reflux for 1.5 hours. The reaction solution was concentrated under reduced pressure, and the resulting residue was dissolved in a mixed solvent of N,N-dimethylformamide (8 ml) and tetrahydrofuran (8 ml), and 5-t-butyloxycarbonylamino-6-oxo-2-phenyl-1,6-dihydro-1-pyrimidinylacetic acid (2.4 g, 7.0 mmol), 1-hydroxybenzotriazole.1H$_2$O (1.3 g, 8.2 mmol), 1-(3-dimethylaminopropyl)-3-ethylcarbodiimide hydrochloride (1.6 g, 8.3 mmol) and N-methylmorpholine (1.5 ml, 14 mmol) were successively added to it, and then the temperature was raised to room temperature, and the mixture was stirred overnight. The reaction solution was diluted with ethyl acetate and washed successively with distilled water, saturated aqueous sodium bicarbonate, 10% aqueous citric acid and saturated saline. The organic layer was dried over anhydrous sodium sulfate and then concentrated under reduced pressure, and diethyl ether was added to the resulting residue whereby solids were precipitated. The precipitated solids were collected by filtration and recrystallized from chloroform/methanol/diethyl ether whereby the title compound (2.3 g, 56% yield) was obtained.

$^1$H-NMR (CDCl$_3$); 1.60: (9H, s), 1.99 (2H, quint, J=7.0 Hz), 2.43 (1H, dt, J=7.0, 1 8.1 Hz), 2.74 (1H, dt, J=7.0, 18.1 Hz), 2.97 (1H, d, J=7.8 Hz), 3.88 (1H, q, J=7.0 Hz), 4.03–4.18 (2H, complex), 4.41 (2H, d, J=3.3 Hz), 4.62 (1H, q, J=7.8 Hz), 6.16 (1H, d t, J=1.4, 6.7 Hz), 6.45–6.54 (1H, m), 6.70 (1H, d, J=9.5 Hz), 7.13–7.53 (12H, complex), 8.68 (1H, s)

Example 13

Synthesis of 2-(5-t-butyloxycarbonylamino-6-oxo-2-phenyl-1,6-dihydropyrimidine-1-yl)-N-{2-hydroxy-3-oxo-1-phenylmethyl-6-(2-pyridyloxy)}hexylacetamide (Compound No. 13)

(1) (4R,5S)-5-{1-oxo-4-(2-pyridyloxy)butyl}-3-(N-t-butyloxycarbonyl)-2,2-dimethyl-4-phenylmethyloxazolidine (Intermediate No. 13)

(4R,5S)-5-{1-t-Butyldimethylsilyloxy-4-(2-pyridyloxy)-butyl}-3-(N-t-butyloxycarbonyl)-2,2-dimethyl-4-phenylmethyloxazolidine (1.3 g, 2.2 mmol) obtained as the by product in Example 12(8) was dissolved in 1.0 M tetrabutyl ammonium fluoride in tetrahydrofuran (6.3 ml, 6.3 mmol) under cooling on ice and stirred overnight at room temperature. The reaction solution was diluted with ethyl acetate and washed successively with 10% aqueous citric acid, saturated aqueous sodium bicarbonate, and saturated saline. The organic layer was dried over anhydrous sodium sulfate and then concentrated under reduced pressure, and the resulting residue was purified by silica gel column chromatography (hexane/ethyl acetate=3/1 to 2/1) to give a crude product. Oxalyl chloride (0.38 ml, 4.4 mmol) was added to methylene chloride (10 ml) under argon atmosphere and cooled at −60° C. A mixture of dimethylsulfoxide (0.62 ml, 8.7 mmol) and methylene chloride (0.62 ml) was added dropwise to it. After addition, the reaction solution was stirred for 15 minutes, and a solution of the above crude product in methylene chloride (20 ml) was added dropwise to it. After addition, the mixture was stirred for 35 minutes, and the reaction temperature was raised to −40° C., and then triethylamine (9.5 ml, 68 mmol) was added to it. The reaction solution was diluted with methylene chloride and washed with distilled water. The organic layer was dried over anhydrous sodium sulfate and then concentrated under reduced pressure, and the resulting residue was purified by silica gel column chromatography (chloroform/ethyl acetate=1/1 to 1/1.5) whereby the title compound (874 mg, 88% yield) was obtained.

$^1$H-NMR (CDCl$_3$); 1.09–1.80 (15H, complex), 1.88–2.09 (2H, m), 2.38–3.34 (4H, complex), 4.14–4.34 (3H, complex), 4.34–4.57 (1H, m), 6.53–6.72 (1H, m), 6.77–6.93 (1H, m), 7.11–7.38 (5H, m), 7.45–7.62 (1H, m), 8.04–8.16 (1H, m)

(2) 2-(5-t-Butyloxycarbonylamino-6-oxo-2-phenyl-1,6-dihydropyrimidine-1-yl)-N-{2-hydroxy-3-oxo-1-phenylmethyl-6-(2-pyridyloxy)}hexylacetamide (Compound No. 13)

(4R,5S)-5-{1-oxo-4-(2-pyridyloxy)butyl}-3-(N-t-butyloxycarbonyl)-2,2-dimethyl-4-phenylmethyloxazolidine (867 mg, 1.9 mmol) was dissolved in methanol (9 ml), and p-toluenesulfonic acid.1H$_2$O (762 mg, 4.2 mmol) was added to it, and the mixture was heated under reflux for 1.5 hours. The reaction solution was concentrated under reduced pressure, and the resulting residue was dissolved in a mixed solvent of N,N-dimethylformamide (2.5 ml) and tetrahydrofuran (2.5 ml), and under cooling on ice 5-t-butyloxycarbonylamino-6-oxo-2-phenyl-1,6-dihydro-1-pyrimidinylacetic acid (763 mg, 2.2 mmol), 1-hydroxybenzotriazole.1H$_2$O (402 mg, 2.6 mmol), 1-(3-dimethylaminopropyl)-3-ethylcarbodiimide hydrochloride (503 mg, 2.6 mmol) and N-methylmorpholine (0.49 ml, 4.4 mol) were successively added to it, and then the temperature was raised to room temperature, and the mixture was stirred overnight. The reaction solution was diluted with ethyl acetate and washed successively with distilled water, saturated aqueous sodium bicarbonate, 10% aqueous citric acid and saturated saline. The organic layer was dried over anhydrous sodium sulfate and then concentrated under reduced pressure, and the resulting residue was purified by silica gel column chromatography (chloroform/methanol=40/1 to 30/1). Solid was precipitated by adding diethyl ether and hexane to this purified material. The precipitated solid was collected by filtration whereby the title compound (2.3 g, 56% yield) was obtained.

$^1$H-NMR (CDCl$_3$); 1.52 (9H, s), 1.91–2.16 (2H, m), 2.54 (1H, dt, J=7.2, 17.8 Hz), 2.79 (1H, dt, J=7.2, 17.8 Hz), 2.97 (2H, d, J=8.0 Hz), 3.90 (1H, d, J=3.4 Hz), 4.04–4.12 (1H, m), 4.13–4.37 (3H, complex), 4.48 (1H, d, J=15.3 Hz), 6.40 (1H, d, J=9.4 Hz), 6.64 (1H, dt, J=0.9, 8.4 Hz), 6.82 (1H, ddd, J=0.9, 5.1, 7.1 Hz), 7.13–7.59 (12H, complex), 8.07 (1H, ddd, J=0.9, 2.2, 5.1 Hz), 8.72 (1H, s)

(3) In this example, it was confirmed that 2 products were formed by thermal treatment of (4R,5S)-5-{1-oxo-4-(2-pyridyloxy)butyl}-3-(N-t-butyloxycarbonyl)-2,2-dimethyl-4-phenylmethyloxazolidine and p-toluenesulfonic acid in methanol. Accordingly, after thermal treatment was finished, a part of the reaction solution was subjected in a usual manner to t-butyloxycarbonylation. As a result, these 2 products were estimated to be the following compounds: (2S,3R)-2-t-Butyloxycarbonylamino-3-hydroxy-4-oxo-1-phenyl-7-(2-pyridyloxy)heptane $^1$H-NMR (CDCl$_3$); 1.38 (9H, s), 1.79–2.12 (2H, complex), 2.38–2.81 (4H, complex), 4.10 (1H br. s), 4.18–4.39 (4H, complex), 5.03 (1H, d, J=8.4 Hz), 6.69 (1H, dt, J=0.8, 8.4 Hz), 6.85 (1H, m), 7.10–7.29 (5H, complex), 7.55 (1H, ddd, J=2.1, 7.2, 8.4 Hz), 8.12 (1H, m)

(2S,3S)-2-t-Butyloxycarbonylamino-3-hydroxy-4-oxo-1-phenyl -7-(2-pyridyloxy)heptane $^1$H-NMR (CDCl$_3$); 1.35 (9H, s), 1.96–2.12 (2H, complex), 2.44–2.67 (1H, m), 2.73–2.98 (3H, complex)3.83 (1H, br. d), 4.03 (1H, br. s), 4.19–4.43 (3H, complex), 4.76 (1H, d, J=9.9 Hz), 6.65 (1H, br. d, J=8.3 Hz), 6.83 (1H, m), 7.24–7.53 (5H, complex), 7.53 (1H, ddd, J 2.0, 7.1, 8.7 Hz) 8.09 (1H, m)

Example 14; R$^0$=3-methylphenyl, R$^2$=methyl (Compound No.17)

$^1$H-NMR (CDCl$_3$): 1.53 (9H, s), 2.20 (3H, s), 2.32 (3H, s), 2.92 (2H, d, J=8.0 Hz), 3.82 (1H, d, J=3.5 Hz), 4.05 (1H, dd, J=1.3, 3.5 Hz), 4.31 (1H, d, J=15.4 Hz), 4.49 (1H, d, J=15.4 Hz), 4.65–4.81 (1H, m), 6.29 (1H, d, J=9.5 Hz), 7.01–7.12 (2H, complex), 7.16 (1H, d, J=7.3 Hz), 7.25–7.32 (1H, overlapped with solvent peak), 7.36–7.50 (6H, complex), 8.73 (1H, s)

Example 15; R$^0$=3-chlorophenyl, R$^2$=methyl (Compound No. 18)

$^1$H-NMR (CDCl$_3$): 1.53 (9H, s), 2.13 (3H, s), 2.57 (1 H, dd, J=6.1, 14.4 Hz), 2.71 (1H, dd, J=8.6, 14.4 Hz), 4.13 (1H, d, J=4.5 Hz), 4.31–4.37 (1H, m), 4.47 (2H, d, J=2.3, 15.3 Hz), 4.63–4.78 (1H, m), 6.79 (1H, d, J=8.8 Hz), 6.94–7.00 (1H, m) 7.12.–7.50 (9H, complex, overlapped with solvent peak), 7.43 (1H, s)

Example 16; R$^0$=4-fluorophenyl, R$^2$=methyl (Compound No. 15)

$^1$H-NMR (CDCl$_3$); 1.53 (9H, s), 2.19 (3H, s), 2.93 (2H, d, J=8.0 Hz), 3.85 (1H, br. s), 4.02 (1H, dd, J=1.2 Hz), 4.33 (1H, d, J=15.4 Hz), 4.46 (1H, d, J=15.4 Hz), 4.62–4.80 (1H, m), 6.26 (1H, d, J=9.5Hz), 6.93–7.06 (2H, m), 7.20–7.32 (5H, complex), 7.39–7.48 (5H, complex), 8.71 (1H, s):MS;m/z=539 (M+1)

Example 17; R$^0$=4-chlorophenyl, R$^2$=methyl (Compound No. 16)

$^1$H-NMR (CDCl$_3$); 1.52 (9H, s), 2.19 (3H, s), 2.93 (2H, d, J=7.8 Hz), 3.87 (1H, br. s), 4.02 (1H, d, J=15.4 Hz), 4.46 (1H, d, J=15.4 Hz), 4.64–4.79 (1H, m), 6.29 (1H, d, J=9.4 Hz), 7.17–7.32 (6H, complex), 7.39–7.56 (5H, complex), 8.72 (1H, s):MS;m/z=556 (M+1)

Example 18; R$^0$=3-fluorophenyl, R$^2$={4-(4-methylpiperazine-1-yl)-4-oxo}propyl (Compound No. 10)

$^1$H-NMR (CDCl$_3$); 1.53 (9H, s) 1.81–1.97 (3H, complex), 2.26–2.80 (11H, complex), 2.95 (2H, d, J=7.6 Hz), 3.41 (2H, br. dd), 3.57 (2H, br, dd), 4.08 (1H, br, d), 4.35 (1H, d, J=15.4 Hz), 4.45 (1H, d, J=15.4 Hz), 4.65 (1H, m), 6.59 (1H, br. d), 6.87–7.51 (3H, complex), 8.72 (1H, s)

Example 19; R$^0$=2-fluorophenyl, R$^2$=methyl (Compound No. 20)

$^1$H-NMR (CDCl$_3$); 1.53 (9H, s), 2.25 (3H, s), 2.53 (1H, dd, J=4.7, 14.3 Hz), 3.20 (1H, m), 3.93 (1H, dd, J=4.6, 6.3 Hz), 4.10–4.58 (3H, complex), 4.70– 4.90 (1H, m), 6.47 (0.5H, d, J=9.5 Hz), 6.75 (0.5H, d, J=7.9 Hz), 6.97–7.43 (9H, complex)

Example 20; R$^0$=3-fluoro-4-hydroxyphenyl, R$^2$=methyl (Compound No. 19)

$^1$H-NMR (CDCl$_3$); 1.53 (9H m), 2.20 (3H, s), 2.86 (2H, d, J=7.8 Hz) 3.93 (1H, br. s), 4.05 (1H, br. s), 4.31 (1H, d, J=15.4 Hz), 4.41 (1H, d, J=15.2 Hz), 4.62–4.76 (1H, m), 6.45–7.00 (5H, complex), 7.38–7.50 (6H, complex), 8.68 (1H, br. s):MS; m/z=555 (M+1)

Example 21; R$^0$=phenyl, R$^2$=methoxy (Compound No. 14)

2-t-Butyloxycarbonylamino-5-phenyl-3,4-dihydropyrazine-4-yl acetic acid as the compound of formula (V) and the compound of formula (III) wherein R$^{3'}$ is an amino group, Z is methylene, R$^0$ is a phenyl group, and R$^2$ is a methoxy group were condensed in the same manner as in Example 1(1) to (2), whereby the compounds of formula (II) wherein R$^1$ is phenyl, R$^3$ is t-butyloxycarbonyl, X is nitrogen, Y is carbon, Z is methylene, R$^0$ and R$^2$ are the groups defined below were synthesized. The compounds of formula (III) are formed in the reaction system from their corresponding oxazolidine derivatives.

The physical properties of the objective compounds of formula (II) are as follows.

R$^0$=phenyl, R$^2$=methoxy (Compound No. 14);
$^1$H-NMR (CDCl$_3$); 1.54 (9H, s), 2.92 (2H, d, J=8.1 Hz), 3.34 (1H, d, J=4.5 Hz), 3.72 (3H, s), 4.07–4.14 (1H, m), 4.26 (1H, d, J=15.1 Hz), 4.39 (1H, d, J=15.1 Hz), 4.53–4.68 (1H, m), 6.52 (1H, d, J=9.2 Hz), 7.13 (1H, s), 7.14–7.53 (11H, complex), 8.23 (1H, s):MS;m/z=537 (M+1)

Examples 22 to 34

The same procedure as in, Example 1(3) was conducted for the oxidation reaction of the alcohol of formula (II) to give the compounds of formula (I) wherein $R^1$ is phenyl, $R^3$ is t-butyloxycarbonyl, X is carbon, Y is nitrogen, Z is methylene, $R^0$ and $R^2$ are groups shown below. The physical properties of the compounds of formula (I) are as follows.

Example 22(1): $R^0$=phenyl, $R^2$=3-phenylpropyl (Compound No. 39)

$^1$H-NMR (CDCl$_3$): 1.53 (9H, s), 1.83–2.00 (2H, m), 2.59–2.82 (4H, complex), 2.91–3.02 (1H, dd, J=7.8, 14.1 Hz), 3.13–3.25 (1H, dd, J=7.8, 14.1 Hz), 4.47 (2H, br. d), 5.22–5.33 (1H, m), 6.47 (1H, br. d, J=6.6 Hz), 7.00–7.50 (16H, complex, overlapped with solvent peak), 8.72 (1H, s)

Example 22(2): $R^0$=phenyl, $R^2$=2-phenylethyl (Compound No. 41)

$^1$H-NMR (CDCl$_3$): 1.53 (9H, s), 2.85–3.20 (4H, complex), 4.47 (2H, br. d), 5.27 (1H, m), 6.47 (1H, br. d, J=6.2 Hz), 6.95–7.50 (16H, complex), 8.72 (1H, s)

Example 23: $R^0$=phenyl, $R^2$=butyl (Compound No. 43)

$^1$H-NMR (CDCl$_3$): 0.92 (3H, t, J=7.1 Hz), 1.22–1.43 (2H, m), 1.47–1.65 (2H, m), 1.54 (9H, s), 2.61–2.83 (2H, m), 2.99 (1H, dd, J=7.8, 14.0 Hz), 3.21 (1H, dd, J=5.3, 14.1 Hz), 4.48 (2H, d, J=1.3 Hz) 6.21–5.34 (1H, m), 6.50 (1H, d, J=6.5 Hz), 7.01–7.54 (11H, complex), 8.71 (1H, s);MS:m/z=561 (M+1)

Example 24: $R^0$=$R^2$=phenyl (Compound No. 45)

$^1$H-MNR (CDCl$_3$): 1.55 (9H, s), 3.16 (1H, dd, J=8.7, 14.2 Hz), 3.38 (1H, dd, J=5.1, 14.2 Hz), 4.42 (2H, s), 5.13 (1H, ddd, J=5.1, 6.4, 8.7 Hz), 6.72 (1H, d, J=6.4 Hz), 7.00–7.70 (14H, complex), 7.93–8.03 (2H, m), 8.67 (1H, s); MS:m/z= 581 (M+1)

Example 25: $R^0$=phenyl, $R^2$=3-carboxypropyl (Compound No. 47)

$^1$H-NMR (CD$_3$OD): 1.34 (1.5H, s), 1.36 (1.5H, s), 1.49 (3H, s), 1.51 (3H, s), 1.60–2.00 (2H, m), 2.24–3.24 (6H, complex), 4.10–4.29 (1H, m), 4.38–4.68.(2H, complex), 6.80–7.56 (10H, complex), 8.43–8.63 (1H, m);MS:m/z=589 (M−H)

Example 26: $R^0$=3-fluorophenyl, $R^2$=3-ethoxycarbonylpropyl (Compound No. 53)

$^1$H-NMR (CDCl$_3$): 1.25 (3H, t, J=7.1 Hz), 1.54 (9H, s), 1.92 (2H, quint, J=7.1 Hz), 2.34 (2H, t, J=7.1 Hz), 2.8 1 (1H, t, J=7.1 Hz), 2.82 (1H, t, J=7.3 Hz), 2.97 (1H, dd, J=9.1, 14.0 Hz), 3.22 (1H, dd, J=5.3, 14.1 Hz) 4.12 (2H, q, J=7.2 Hz), 4.49 (2H, s), 5.16–5.28 (1H, m), 6.62 (1H, d, J=6.2 Hz), 6.78–6.99 (3H, m), 7.16–7.29 (2H, m), 7.43–7.50 (5H, m), 8.71 (1H, s); IR (KBr): 3410, 2990, 1727, 1655, 1510, 1490, 1369, 1250, 1152cm−1;MS:m/z=581 (M+H−56)

Example 27: 2-(5-t-Butyloxycarbonylamino-6-oxo-2-phenyl-1,6-dihydropyrimidine-1-yl)-N-{2,3-dioxo-6-(2-oxo-1,2-dihydropyridine-1-yl)-1-phenylmethyl}hexylacetamide (Compound No. 72)

2-(5-t-Butyloxycarbonylamino-6-oxo-2-phenyl-1,6-dihydropyrimidine-1-yl)-N-{2-hydroxy-3-oxo-6-(2-oxo-1,2-dihydropyridine-1-yl)-1-phenylmethyl}hexylacetamide (115 mg, 0.18 mmol) was dissolved in dimethylsulfoxide (2 ml), under argon atmosphere, and 1-(3-dimethylaminopropyl)-3-ethylcarbodiimide hydrochloride (103 mg, 0.54 mmol) and pyridinium trifluoroacetate (17 mg, 0.1 mmol) were added to it, and the mixture was stirred for 3.5 hours. The reaction solution was diluted with ethyl acetate and washed successively with distilled water and saturated saline. The organic layer was dried over anhydrous sodium sulfate and then concentrated under reduced pressure, and the resulting residue was purified by silica gel column chromatography (chloroform/methanol=30/1), and thereafter hexane was added to it to precipitate solid. The precipitated solid was collected by filtration whereby the title compound (96 mg, 83% yield) was obtained.

$^1$H-NMR (CDCl$_3$); 1.60 (9H, s), 1.99 (2H, quint, J=7.0 Hz), 2.43 (1H, dt, J=7.0, 18.1 Hz), 2.74 (1H, dt, J=7.0, 18.1 Hz), 2.97 (1H, d, J=7.8 Hz), 3.8.8 (1H, q, J=7.0 Hz) 4.03–4.18 (2H, complex), 4.41 (2H, d, J=3.3 Hz), 4.62 (1H, q, J=7.8 Hz), 6.16 (1H, d t, J=1.4, 6.7 Hz), 6.45–6.54 (1H, m), 6.70 (1H, d, J=9.5 Hz), 7.13–7.53 (12H, complex), 8.68 (1H, s)

Example 28; 2-(5-t-Butyloxycarbonylamino-6-oxo-2-phenyl-1,6-dihydropyrimidine-1-yl)-N-{2,3-dioxo-6-(2-pyridyloxy)-1-phenylmethyl}hexylacetamide (Compound No. 74)

2-(5-t -Butyloxycarbonylamino-6-oxo-2-phenyl-1,6-dihydropyrimidine-1-yl)-N-{2-hydroxy-3-oxo-1-phenylethyl-(2-pyridyloxy)}hexylacetamide (823 mg, 1.28 mmol) was dissolved in dimethylsulfoxide (0.46 ml), and 1-(3-dimethylaminopropyl)-3-ethylcarbodiimide hydrochloride (740 mg, 3.85 mmol) and pyridinium trifluoroacetate (123.6 mg, 0.64 mmol) were added to it, and the mixture was stirred for 1.5 hours. The reaction solution was diluted with ethyl acetate and washed successively with distilled water and saturated saline. The organic layer was dried over anhydrous sodium sulfate and concentrated under reduced pressure, and the resulting residue was purified by silica gel column chromatography (chloroform/ethyl acetate=2/1 to 1/1), and then diethyl ether was added to it to precipitate solid. The precipitated solid was collected by filtration whereby the title compound (401 mg, 49% yield) was obtained.

$^1$H-NMR (CDCl$_3$): 1.52 (9H, s) 2.07 (2H, quint; J=6.5 Hz), 2.75–3.29 (4H, complex), 4.30 (2H, t, J=6.5 Hz), 4.41–4.53 (2H, m), 5.22–5.38 (1H, m), 6.63 (1H, d, J=6.6 Hz), 6.69 (1H, dt, J=1.0, 8.4 Hz) 6.84 (1H, ddd, J=1.0, 5.1, 7.1 Hz), 6.94–7.50 (11H, complex), 7.55 (1H, ddd, J=2.0, 7.1, 8.4 Hz), 8.10 (1H, ddd, J=1.0, 2.0, 5.1 Hz), 8.71 (1H, s); MS:m/z=640 (M+1)

Example 29; $R^0$=3-methylphenyl, $R^2$=methyl (Compound No. 59)

$^1$H-NMR (CDCl$_3$): 1.54 (9H, s), 2.29 (3H, s), 2.33 (3H, s), 2.94 (1H, dd, J=8.1, 14.0 Hz), 3.16 (1H, dd, J=5.4, 14.0 Hz) 4.49 (2H, s), 5.21 (1H, ddd, J=5.4, 6.1, 8.1 Hz) 6.48 (1H, d, J=6.1 Hz) 6.79–7.63 (10H, complex), 8.71 (1H, s)

Example 30; $R^0$=3-chlorophenyl, $R^2$=methyl (Compound No. 61)

$^1$H-NMR (CDCl$_3$); 1.54 (9H, s), 2.35 (3H, s), 2.94 (1H, dd, J=8.2, 14.1 Hz), 3.21 (1H, dd, J=5.1, 14.1 Hz), 4.47 (2H, s), 5.17 (1H, ddd, J=5.1, 6.3, 8.2 Hz), 6.63 (1H, d, J=6.3 Hz), 6.89–7.05 (1H, m), 7.11 (1H, s), 7.15–7.24 (3H, m), 7.24–7.59 (5H, m), 8.72 (1H, s)

Example 31; $R^0$=4-fluorophenyl, $R^2$=methyl (Compound No. 55)

$^1$H-NMR (CDCl$_3$) 1.54 (9H, s), 2.34 (3H, s), 2.96 (1H, dd, J 7.8, 14.1 Hz), 3.13–3.37 (1H, m), 4.48 (2H, s), 5.15–5.27 (1H, m), 6.50 (1H, d, J=6.6 Hz), 6.83–7.58 (10H, complex), 8.72 (1H, br, s):MS;m/z=536 (M+1)

Example 32; $R^0$=4-chlorophenyl, $R^2$=methyl (Compound No. 57)

$^1$H-NMR (CDCl$_3$); 1.54 (9H, s), 2.34 (3H, s), 2.94 (1H, dd, J=7.9, 14.1 Hz), 3.21 (1H, dd, J=5.3, 14.1 Hz), 4.48 (2H, s), 5.13–5.25 (1H, m), 6.55 (1H, d, J=6.6 Hz), 6.97–7.27 (5H, complex), 7.31–7.56 (5H, complex), 8.72 (1H, br. s): IR (KBr); 3400, 1718, 1658, 1509, 1490, 1414, 1389, 1365, 1250, 1219, 1150, 1082 cm−1; MS:m/z=554 (M+1)

Example 33; $R^0$=3-fluorophenyl, $R^2$={4-(4-methylpiperazine-1-yl)-4-oxo}propyl (Compound No. 68)

$^1$H-NMR (CDCl$_3$); 1.53 (9H, s), 1.85–2.05 (2H, complex), 2.27–2.50 (9H, complex), 2.75–3.27 (4H, complex), 3.43–3.65 (4H, complex), 4.50 (2H, s), 5.10 (1H, m), 6.78–7.02 (4H, complex), 7.16–7.35 (2H, overlapped with solvent peak), 7.40–7.54 (5H, complex), 8.70 (1H, s)

Example 34; $R^0$=2-fluorophenyl, $R^2$=methyl (Compound No. 63)

$^1$H-NMR (CDCl$_3$); 1.54 (9H, s), 2.38 ((3H, s), 3.21 (2H, br. d), 4.50 (2H, s), 5.41 (1H, dd, J=5.8, 7.0 Hz), 6.46 (1H, d, J=7.0 Hz) 6.90–7.27 (4H, complex), 7.48 (1H, s)

Example 35; Synthesis of Compound No. 66

The same procedure as in Example 1(3) was conducted for oxidation reaction of the alcohol of formula (II) to give the compound of formula (I) (Compound No. 66) wherein $R^1$ is phenyl, $R^3$ is t-butyloxycarbonyl, X is nitrogen, Y is carbon, Z is methylene, $R^0$ is a phenyl group, and $R^2$ is a methoxy group.

$^1$H-NMR (CDCl$_3$); 1.56 (9H, s), 2.51–3.33 (2H, m), 3.65–3.89 (3H, m), 4.21–5.50 (3H, complex), 6.36–6.60 (1H, m), 6.98–7.52 (11H, complex), 8.12– 8.27 (1H, m); MS:m/z=535 (M+1)

Examples 36 to 49

The same procedure as in Example 1(4) was conducted for deprotection of the compound of formula (I) wherein $R^3$ is a t-butyloxycarbonyl group to give the corresponding hydrochlorides of the compounds of formula (I) wherein $R^3$ is hydrogen, $R^1$ is phenyl, X is carbon, Y is nitrogen, Z is methylene, $R^0$ and $R^2$ are the groups defined below.

Example 36: $R^0$=3-fluoro-4-hydroxyphenyl, $R^2$=methyl (Compound No. 50);

$^1$H-NMR (CD$_3$OD): 2.23–2.39 (3H, m), 3.12–3.65 (2H, m), 4.48–5.12 (3H, complex), 6.68–7.04 (3H, m), 7.22–7.90 (6H, complex)

Example 37; $R^0$=phenyl, $R^2$=butyl (Compound No. 44)

$^1$H-NMR (CDCl$_3$); 0.86 (3H, t, J=6.9 Hz), 1.17–1.58 (4H, m), 2.40–2.78 (2H, m), 2.80–3.18 (2H, m), 4.30–4.80 (2H, m), 5.12–5.53 (1H, m), 6.84–7.82 (11H, complex):MS;m/z=461 (M+1)

Example 38; $R^0$=$R^2$=phenyl (Compound No. 46)

$^1$H-NMR (CDCl$_3$); 3.16 (1H, dd, J=8.5, 14.2 Hz), 3.38 (1H, dd, J=5.1, 14.2 Hz), 3.98 (2H, br. s), 4.42 (2H, s), 5.17 (1H, ddd, J=5.1, 6.3, 8.5 Hz), 6.88 (1H, d, J=6.3 Hz), 7.08–7.72 (14H, complex), 7.94– 8.05 (2H, m):MS;m/z=481 (M+1)

Example 39; $R^0$=phenyl, $R^2$=3-phenylpropyl (Compound No. 40)

MS;m/z=560 (M+1)

Example 40; $R^0$=phenyl, $R^2$=2-phenylethyl (Compound No. 42)

MS;m/z=546 (M+1)

Example 41; $R^0$=phenyl, $R^2$=3-carboxypropyl (Compound No.48)

$^1$H-NMR (CD$_3$OD): 1.73–2.05 (11H, complex), 2.15–3.25 (6H, complex), 3.95–4.72 (3H, complex), 7.05–7.65 (11H, complex); MS:m/z=491 (M+1)

Example 42: $R^0$=3-fluorophenyl, $R^2$=3-ethoxycarbonylpropyl (Compound No. 54)

$^1$H-NMR (DMSO-d6)): 1.17 (3H, t, J=7.1 Hz), 1.72 (2H, quint, J=7.2 Hz), 2.31 (2H, t, J=7.4 Hz), 2.62–2.90 (3H, m), 3.10 (1H, dd, J=4.5, 13.9 Hz), 4.05 (2H, q, J=7.1 Hz), 4.36 (1H, d, J=16.5 Hz), 4.4 2 (1H, d, J=16.5 Hz), 4.82–4.93 (1H, m), 6.86–7.10 (3H, m), 7.21–7.65 (7H, m), 9.01 (1H, d, J=6.6 Hz); IR (K Br): 3700–2400, 1683, 1646, 1540, 1373, 1250, 1180 cm−1;M:m/z=537 (M+1)

Example 43: $R^0$=phenyl, $R^2$=3-(2-pyridyloxy)propyl (Compound No. 75);

$^1$H-NMR (DMSO-d6): 1.94 (2H, quint, J=6.7 Hz), 2.58–3.20 (4H, complex), 4.27 (2H, t, J=6.7 Hz), 4.44 (1H, br. s), 4.45 (1H, br. s), 4.88–5.01 (1H, m), 6.78–6.94 (1H, m), 6.96–7.08 (1H, m), 7.08–7.70 (11H, complex), 7.70–7.86 (1H, m), 8.10–8.20 (1H, m), 8.90–9.05 (1H, m); MS:m/z=540 (M+1)

Example 44: $R^0$=3-methylphenyl, $R^2$=methyl (Compound No. 60)

$^1$H-NMR (DMSO-d6):2.09–2.36 (6H, complex), 2.72 (1H, dd, J=9.0, 13.8 Hz), 3.02 (1H, dd, J=4.8, 13.8 Hz), 4.41 (2H, s, overlapped with solvent peak), 4.73–4.94 (1H, m), 6.82–7.24 (4H, m); 7.25–7.68 (5H, m), 8.94 (1H, d, J=6.2 Hz)

Example 45: $R^0$=3-chlorophenyl, $R^2$=methyl (Compound No. 62)

$^1$H-NMR (DMSO-d6): 2.07–2.34 (3H, m), 2.75 (1H, dd, J=9.3, 14.0 Hz), 3.09 (1H, dd, J=4.7, 14.0 Hz), 3.80–5.30 (3H, complex, overlapped with solvent peak), 6.96–7.80 (9H, complex), 9.04 (1H, d, J=6.3 Hz)

Example 46: $R^0$=4-chlorophenyl, $R^2$=methyl (Compound No. 58)

$^1$H-NMR (DMSO-d6): 2.24 (3H, s), 2.74 (1H, dd, J=9.2, 13.9 Hz), 3.07 (1H, dd, J=4.7, 13.9 Hz), 4.40 (2H, s), 4.10–5.20 (4H, complex), 7.10–7.64 (10 H, complex), 8.97 (1H, d, J=6.6 Hz); MS:m/z=454 (M+1)

Example 47: $R^0$=4-fluorophenyl, $R^2$=methyl (Compound No. 56)

$^1$H-NMR (DMSO-d6): 2.23 (3H, s), 2.74 (1H, dd, J=9.0, 13.9 Hz), 3.06 (1H, dd, J=4.9, 13.9 Hz), 4.40 (2H, overlapped with solvent peak),4.74–4.90 (1H, overlapped with solvent peak), 6.88–7.66 (10H, complex), 8.95 (1H, d, J=6.4 Hz); MS:m/z=437(M+1)

Example 48: $R^0$=3-fluorophenyl, $R^2$={4-(4-methylpiperazine-1-yl)-4-oxo}propyl (Compound No. 69)

MS:m/z=691 (M+1)

Example 49; $R^0$=2-fluorophenyl, $R^2$=methyl (Compound No. 64)

$^1$H-NMR (CDCl$_3$);2.23 (3H, s), 2.86 (1H, dd, J=8.2, 13.8 Hz), 4.42 (2H, s), 4.88–4.95 (1H, m), 7.01–7.62 (9H, complex), 8.96 (1H, d, J=6.5 Hz)

Example 50

The same procedure as in Example 1(4) was conducted for deprotection of the compound of formula (i) wherein $R^3$ is a t-butyloxycarbonyl group to give a corresponding hydrochloride of the compound (Compound No. 67) of formula (I) wherein $R^3$is hydrogen, $R^1$ is phenyl, X is nitrogen, Y is carbon, Z is methylene, $R^0$ is a phenyl group, and $R^2$ is a methoxy group.

¹H-NMR (CDCl₃): 2.95 (1H, dd, J=8.2, 14.1 Hz), 3.16 (1H, dd, J=5.7, 14.1 Hz), 3.84 (3H, s), 4.43 (2H, s), 5.18–5.35 (1H, m), 6.47–6.60 (1H, m), 7.08–7.53 (11H, complex), 8.59 (1H, d, J=7.1 Hz), 9.17 (2H, br. s); MS:m/z=435 (M+1)

Example 51

Synthesis of 2-(5-amino-6-oxo-2-phenyl-1,6-dihydropyrimidine-1-yl)-N-{2,3-dioxo-1-(3-flourophenyl)methyl-}butylacetamide (Compound No. 52) hydrochloride was conducted in the following manner.

(1) 2-(5-t-Butyloxycarbonylamino-6-oxo-2-phenyl-1,6-dihydropyrimidine-1-yl)-N-{1-(3-flourophenyl)methyl-2-hydroxy-3-oxo}butylacetamide (Compound No. 8)

3-t-Butyloxycarbonyl-2,2-dimethyl-5-(1-oxoethyl)-4-(3-fluorophenyl)methyloxazolidine (17.94 g, 51.1 mmol) was dissolved in ethanol (180 ml), and p-toluenesulfonic acid.1H₂O (10.7 g, 56.2 mmol) was added to it and the mixture was heated under reflux for 2 hours with stirring. The reaction solution was concentrated under reduced pressure, and the resulting residue was dried with a vacuum pump (2 mmHg) at 50° C., whereby crude 2-amino-1-(3-fluorophenyl)-3-hydroxy-4-oxopentane p-toluenesulfonate (21.5 g) was obtained as solid. This solid was subjected without further purification to the subsequent condensation reaction.

The solid (21.5 g) obtained by the above reaction and 5-t-butyloxycarbonylamino-6-oxo-2-phenyl-1,6-dihydro-1-pyrimidinylacetic acid (1.42 g, 4.14 mmol) were dissolved in dimethylformamide (311 ml), followed by successively adding 1-(3-dimethylaminopropyl)-3-ethylcarbodiimide hydrochloride (12.7 g, 66.4 mmol), 1-hydroxybenzotriazole.1H₂O (10.2 g, 66.4 mmol) and 4-methylmorpholine (7.6 ml, 66.4 mmol) under cooling on ice, and the mixture was stirred overnight at room temperature. The reaction solution was diluted with ethyl acetate and washed successively with 5% aqueous citric acid, saturated aqueous sodium bicarbonate, distilled water and saturated saline. After the organic layer was dried by adding anhydrous sodium sulfate, the drying agent was removed by filtration, and the filtrate was concentrated under reduced pressure. The resulting residue was purified by silica gel column chromatography. (chloroform/methanol=80/20 to 65/35), whereby the title compound (18.7 g, 68% yield) was obtained.

¹H-NMR; 1.53 (9H, s), 2.21 (3H, s), 2.97 (2H, d, J=8.0 Hz), 4.04 (1H, d, J=1.4 Hz), 4.32 (1H, d, J=15.4 Hz), 4.48 (1H, d, J=15.4 Hz), 4.67–4.82 (1H, m), 6.35 1H, d, J=9.4 Hz) 6.88–7.08 (3H, complex), 7.24–7.48 (7H, overlapped with solvent peak), 8.72 (1H, s)

3-t-Butyloxycarbonyl-2,2-dimethyl-5-(1-oxoethyl)-4-(3-fluorophenyl)methyloxazolidine (Intermediate No. 8) used above was obtained in the following manner.

According to the method reported by R. Nishizawa et al. in J. Med. Chem., 20(4), 510–515, acetamide malonic acid ester and 3-fluorobenzyl chloride were condensed, and then its ester was hydrolyzed, and it was followed by decarboxylation, and deprotected to the amino group, and the resulting 3-fluorophenyl alanine was used as the starting material to give 3-amino-2-hydroxy-4-(3-fluorophenyl) butyric acid, which was then protected at its 3-amino group with a t-butyloxycarbonyl group and subjected in a usual manner to condensation reaction with N,O-dimethylhydroxylamine whereby 3-t-butyloxycarbonylamino-2-hydroxy-4-(3-fluorophenyl) butyric acid -N,O-dimethyl-hydroxylamide was obtained.

The resulting amide is treated with a catalytic amount of p-toluenesulfonic acid in 2,2-dimethoxypropane whereby 3-t-butyloxycarbonyl-2,2-dimethyl-5-(N-methoxy-N-methyl) -4-(3-fluorophenyl)oxazolidine could be easily obtained.

The resulting oxazolidine was treated with a Grignard reagent in an inert solvent under argon atmosphere according to the method described in Example 1(1) whereby the desired compound 3-t-butyloxycarbonyl-2,2-dimethyl-5-(1-oxoethyl)-4-(3-fluorophenyl)methyloxazolidine could be synthesized.

(2) 2-(5-t-Butyloxycarbonylamino-6-oxo-2-phenyl-1,6-dihydropyrimidine-1-yl)-N-{2,3-dioxo-1-(3-fluorophenyl)methyl}butylacetamide (Compound No. 51)

Oxalyl chloride (5.06 ml, 58.0 mmol) was added to methylene chloride (566 ml) at room temperature under nitrogen atmosphere and cooled at −75° C. After dimethylsulfoxide (5.49 ml, 77.4 mmol) was added dropwise to this solution, a solution of 2-(5-t-butyloxycarbonylamino-6-oxo-2-phenyl -1,6-dihydropyrimidine-1-yl)-N-{1-(3-fluorophenyl)methyl-2-hydroxy-3-oxo}butylacetamide (20.8 g, 38.7 mmol) in methylene chloride (900 ml) was added dropwise to it. After 20 minutes, triethylamine (21.6 ml, 155 mmol) was added dropwise to the reaction mixture, and the temperature of the reaction solution was raised naturally to room temperature. The reaction solution was washed successively with 10% aqueous citric acid and distilled water, and then the organic layer was dried over anhydrous sodium sulfate. The drying agent was removed by filtration, and then the filtrate was concentrated under reduced pressure. The resulting residue was purified by silica gel column chromatography (chloroform/ethyl acetate=20/1 to 9/1), whereby the title compound (24.0 g, 58% yield) was obtained.

¹H-NMR (CDCl₃); 1.54 (9H, s), 2.34 (3H, s), 2.96 (1H, dd, J=7.8, 14.1 Hz), 3.13–3.37 (1H, m), 4.48 (2H, s), 5.15–5.27 (1H, m), 6.50 (1H, d, J=6.6 Hz), 6.83–7.55 (11H, complex), 8.67–8.77 (1H, m):MS;m/z=537 (M+1)

(3) 2-(5-Amino-6-oxo-2-phenyl-1,6-dihydropyrimidine-1-yl)-N-{1-(3-fluorophenyl)methyl-2,3-dioxo}butylacetamide (Compound No. 52) hydrochloride 2-(5-t-Butyloxycarbonylamino-6-oxo-2-phenyl-1,6-dihydropyrimidine-1-yl)-N-{1-(3-fluorophenyl)methyl-2,3-dioxo}butylacetamide (24.0 g, 44.7 mmol) was dissolved in 4 N hydrogen chloride/1,4-dioxane (9 ml, 36.2 mmol) and stirred at room temperature for 1.5 hours. The reaction solution was concentrated under reduced pressure, and diethyl ether was added to the resulting residue, and the precipitated solid was collected by filtration whereby the title compound (21.1 g, 99% yield) was obtained.

¹H-NMR (DMSO-d6); 2.24 (3H, s), 2.78 (1H, dd, J=9.1, 13.9 Hz), 3.11 (1H, dd, J=4.7, 13.9 Hz), 4.40 (2H, br. s), 4.79–4.92 (1H, m), 6.93–7.09 (3H, complex, overlapped with 1H), 7.20–7.65 (7H, complex, overlapped with 1H), 9.06 (1H, d, J=6.5):MS; m/z=437 (M+1)

Example 52

Synthesis of 2-(5-amino-6-oxo-2-phenyl-1,6-dihydropyrimidine-1-yl)-N-{2,3-dioxo-(4-morpholine-4-yl)-1-phenyl methyl}hexylacetamide (Compound No. 71) dihydrochloride was conducted in the following manner.

(1) 2-(5-t-Butyloxycarbonylamino-6-oxo-2-phenyl-1,6-dihydropyrimidine-1-yl)-N-(2R,3S)-{2-hydroxy-3-oxo-6-(4-morpholine-4-yl)-1-phenylmethyl}hexylacetamide trifluoracetate (Compound No. 11)

(4S,5R)-3-t-Butyloxycarbonyl-2,2-dimethyl-5-{4-(4-morpholine-4-yl)-1-oxobutyl-4-phenylmethyloxazolidine (130.3 g, 270 mmol) was dissolved in methanol (674 ml), and p-toluenesulfonic acid.1H₂O (51.3 g, 270 mmol) was added to it and the mixture was heated for 6 hours under reflux with stirring. The reaction solution was concentrated under reduced pressure, and the resulting residue (2-amino-3-hydroxy-7-(4-morpholine-4-yl)-4-oxo-1-phenylheptane monchydrochloride mono-p-toluenesulfonate) was subjected to the following condensation reaction without isolation and purification.

The above reaction residue and 5-t-butyloxycarbonylamino-6-oxo-2-phenyl-1,6-dihydro-1-pyrimlidinylacetic acid (60.1 g, 174 mmol) were dissolved in a mixed solvent of dimethylformamide (145 ml) and tetrahydrofuran (290 ml), followed by successively adding 1-(3-dimethylaminopropyl)-3-ethylcarbodiimide hydrochloride (37.4 g, 191 mmol), 1-hydroxybenzotriazole.1H$_2$O (26.6 g, 174 mmol) and 4-methylmorpholine (19.1 ml, 174 mmol) under cooling on ice, and then the mixture was stirred overnight at room temperature. The reaction solution was diluted with ethyl acetate and washed successively with 5% aqueous citric acid, saturated aqueous sodium bicarbonate, distilled water and saturated saline. After the organic layer was dried by adding anhydrous sodium sulfate, the drying agent was removed by filtration, and the filtrate was concentrated under reduced pressure. The resulting residue was dissolved in ethyl acetate (1500 ml), and trifluoroacetic acid (13.4 ml, 174 mmol) was added dropwise to it under cooling on ice. The precipitated solid was collected by filtration whereby the title compound (72.7 g, 56% yield) was obtained.

$^1$H-N M R (CDCl$_3$): 1.53 (9H, s) 1.60–1.76 (1H, m), 1.77–1.92 (1H, m), 2.10–2.60 (8H, complex), 2.93–2.99 (2H, complex), 3.55 (4H, t, J=4.6 Hz), 4.11 (1H, s), 4.33 (1H, d, J=15.3 Hz), 4.48 (1H, d, J=15.3 Hz), 4.63–4.77 (I H, m), 6.28 (1H, d, J=9.5 Hz), 7.22–7.34 (6H, complex), 7.35–7.49 (5H, complex), 8.25 (1H, s)

(4S,5R)-3-t-Butyloxycarbonyl-2,2-dimethyl-5-{4-(4-morpholine-4-yl)-1-oxobutyl}-4-phenylmethyloxazolidine (Intermediate No. 11) used above was obtained in the following manner.

According to the method reported by R. Nishizawa et al. in J. Med. Chem., 20(4), 510–515, (2R,3S)-3-amino-2-hydroxy-4-phenylbutyric acid was obtained using L-phenylalanine as the starting material, and protected at its 3-amino group with the t-butyloxycarbonyl group, and then subjected in a usual manner to condensation reaction with N,O-dimethylhydroxylamine whereby the corresponding (2R,3S)-3-t-butyloxycarbonylamino-2-hydroxy-4-phenylbutyric acid-N,O-dimethylhydroxylamide was obtained.

The resulting amide was treated in usual manner, for example, with a catalytic amount of p-toluenesulfonic acid in 2,2-dimethoxypropane whereby (4S, 5R)-3-t-butyloxycarbonyl-2,2-dimethyl-5-(N-methoxy-N-methyl)-4-phenylmethyloxazolidine could be easily obtained.

The resulting oxazolidine was treated with a Grignard reagent in an inert solvent under argon atmosphere according to the method described in Example 1(1) whereby the desired compound (4S,5R)-3-t-butyloxycarbonyl-2,2-dimethyl-5-{4-(4-morpholine-4-yl)-1-oxobutyl-4-phenylmethyloxazolidine could be synthesized.

(2) 2-(5-t-Butyloxycarbonylamino-6-oxo-2-phenyl-1,6-dihydropyrimidine-1-yl)-N-(2,3-dioxo-6-(4-yl)-1-phenylmethyl)hexylacetamide (Compound No. 70)

2-(5-t-Butyloxycarbonylamino-6-oxo-2-phenyl-1,6-dihydropyrimidine-1-yl)-N-(2R,3S)-{2-hydroxy-3-oxo-6-(4-morpholine-4-yl)-1-phenylmethyl}hexylacetamide trifluoroacetate (70.3 mg, 94.1 mmol) was dissolved in a mixed solvent of methylene chloride (470 ml) and dimethylsulfoxide (33.4 ml), and trifluoroacetic acid (3.6 ml, 47.0 mmol), pyridine (3.8 ml, 47.0 mmol) and 1-(3-dimethylaminopropyl)-3-ethylcarbodiimide hydrochloride (55.2 g, 282 mmol) were added to it in this order at room temperature, and the mixture was stirred for 50 minutes. The reaction solution was diluted with methylene chloride, and then washed with distilled water. The organic layer was dried over -anhydrous sodium sulfate, and then the drying agent was removed by filtration, and the solution was concentrated under reduced pressure whereby the title compound was obtained.

This compound was subjected to the subsequent deprotection reaction without isolation and purification.
MS: m/z=632 (M+1)

(3) 2-(5-Amino-6-oxo-2-phenyl-1,6-dihydropyrimidine-1-yl)-N-{2,3-dioxo-6-(4-morpholine-4-yl)-1-phenylmethyl}hexylacetamide (Compound No. 71) dihydrochloride 2-(5-t-Butyloxycarbonylamino-6-oxo-2-phenyl-1,6-dihydropyrimidine-1-yl)-N-(2,3-dioxo-6-(4-morpholine-1-yl)-1-phenylmethyllhexylacetamide obtained in the previous experiment was dissolved in a mixed solvent of ethyl acetate (235 ml) and 4 N hydrogen chloride/1,4-dioxane (235 ml), and stirred overnight at room temperature. The precipitated solid was collected from the reaction solution by filtration whereby the title compound (56.8 g, 99% yield) was obtained.

R$^0$=phenyl, R$^2$=3-(4-morpholine-4-yl)propyl (Compound No. 71); MS:m/z=532 (M+1)

Hereinafter, a synthetic method of the compound of formula I from the compound of formula (XIII), i.e. 2-(5-t-butyloxycarbonylamino-6-oxo-2-phenyl-1,6-dihydropyrimidine-1-yl)-N-{(1S,2R)-2-hydroxy-3-oxo-1-phenylmethyl-6-(2-pyridyloxy)}hexylacetamide by the synthetic route in scheme 1 is described.

Example 53

Hereinafter, a synthetic method of a common intermediate 2-(5-amino-6-oxo-2-phenyl-1,6-dithydro-pyrimidine-1-yl)-N-{(1S,2R)-2-acetyloxy-3-oxo-1-phenyl-methyl-6-(2-pyridyloxy))hexylacetamide dihydrochloride (Compound No. 23) is described.

(1) 2-(5-t-Butyloxycarbonylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (Compound No. 22)

2-(5-t-Butyloxycarbonylamino-6-oxo-2-phenyl-1,6-dihydropyrimidine-1-yl)-N-{(1S,2R)-2-hydroxy-3-oxo-1-phenylmethyl-6-(2-pyridyloxy)}hexylacetamide (1 g, 1.56 mmol) was dissolved in pyridine (1.6 ml), and acetic anhydride (0.176 ml, 1.87 mmol) was added to it under cooling on ice, and the mixture was stirred at 0° C. for 30 minutes and at room temperature for 2 hours. After saturated aqueous sodium bicarbonate was added, the reaction solution was extracted with ethyl acetate,and then it was washed with saturated saline, and dried over anhydrous sodium sulfate. The organic layer was concentrated under reduced pressure, and the resulting residue was purified by silica gel column chromatography (hexane/ethyl acetate/methanol=10/10/1) whereby the title compound (1.08 g, quant.) was obtained as white solid.

$^1$H-NMR (CDCl$_3$); 1.52 (9H, s), 1.92–2.08 (2H, m), 2.19 (3H, 8), 2.45–3.30 (4H, complex), 4.24 (2H, t, J=6.5 Hz), 4.44 (2H, d, J=7.6 Hz), 4.72–4.89 (1H, m), 4.97 (1H, d, J=2.2 Hz), 6.44 (1H, d, J=9.4 Hz), 6.68 (1H, d, J=8.3 Hz), 6.82 (1H, ddd, J=0.93, 4.0, 7.1 Hz), 7.11–7.35 (7H, complex), 7.36–7.58 (5H, complex), 8.08 (1H, ddd, J=1.0, 1.8, 4.0 Hz), 8.72 (1H, br. S):MS;m/z=684 (M+1), 1367 (2M+1)

(2) 2-(5-Amino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide dihydrochloride (Compound No. 23)

2-(5-t-Butyloxycarbonylamino-6-oxo-2-phenyl-1,6-dihydropyrimidine-1-yl)-N-{(1S,2R)-2-acetyloxy-3-3-oxo-1-phenylmethyl-6-(2-pyridyloxy)}hexylacetamide (1.08 g, 1.58 mmol) was dissolved in 2 ml dioxane, and 4 N hydrogen chloride/1,4-dioxane (7.9 ml, 31.6 mmol) was added to it under cooling on ice, and the mixture was stirred at 0° C. for 30 minutes and at room temperature overnight. The reaction solution was concentrated under reduced pressure whereby the title compound (1.08 g, quant.) was obtained as white solid.
$^1$H-NMR (CD$_3$OD);2.09–2.23 (2H, m), 2.20 (3H, s), 2.61–3.50 (4H, complex), 4.34–4.85 (5H, complex), 5.04 (1H, d), 7.15–7.31 (5H, complex), 7.43–7.67 (7H, complex), 7.69–7.79 (1H, m), 8.32–8.38 (1H, m), 8.46 (1H, ddd, J=1.7, 7.3, 10 Hz):MS;m/z=584 (M+1)

Example 54

Synthesis of 2-(5-benzylsulfonylamino-6-oxo-2-phenyl-1,6-dihydropyrimidine-1-yl)-N-{2,3-dioxo-1-phenylmethyl-6-(2-pyridyloxy)}-hexylacetamide (Compound No. 77) was conducted in the following manner.
(1) 2-(5-Benzylsulfonylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (Compound No. 24)

The common intermediate 2-(5-amino-6-oxo-2-phenyl-1, 6-dihydropyrimidine-1-yl)-N-{(1S,2R)-2-acetyoloxy-3-oxo-1-phenylmethyl-6-(2-pyridyloxy)}hexylacetamide dihydrochloride (760 mg, 1.16 mmol) was dissolved in pyridine (1.2 ml), and after benzylsulfonyl chloride (221 mg, 1.16 mmol) was added under cooling on ice, the mixture was stirred at 0° C. for 1 hour and at room temperature for 1 hour. After saturated aqueous sodium bicarbonate was added, the reaction solution was extracted with ethyl acetate, and the organic layer was washed with saturated saline. After dried over anhydrous sodium sulfate, the organic layer was concentrated under reduced pressure, and the resulting residue was purified by silica gel column chromatography (hexane/ethyl acetate/methanol=10/20/1) whereby the title compound (590 mg, 69% yield) was obtained as white solid.
$^1$H-NMR (CDCl$_3$); 1.85–2.02 (2H, m), 2.29 (3H, s), 2.42–2.75 (2H, m), 2.82–3.07 (2H, m), 4.07 (2H, d, J=4.1 Hz), 4.16 (2H, t, J=6.3 Hz), 4.75–4.92 (1H, m), 4.96 (1H, d, J=1.9 Hz), 6.64 (1H, d, J=8.4 Hz), 6.72–6.86 (2H, complex), 7.02–7.62 (16H, complex), 8.02–8.07 (1H, m), 8.04 (1H, m), 8.15–8.35 (1H, m):MS; m/z=738 (M+1)
(2) 2-(5-Benzylsulfonylamino-6-oxo-2-phenyl-1,6-dihydropyrimidine-1-yl)-N-{(1S,2R)-2-hydroxy-3-oxo-1-phenylmethyl-6-(2-pyridyloxy)}hexylacetamide (Compound No. 25)

2-(5-Benzylsulfonylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (590.4 mg, 0.8 mmol) was dissolved in methanol (3.2 ml), and after an aqueous solution (1 ml) of potassium carbonate (332 mg) was added under cooling on ice, the mixture was stirred at 0° C. for 30 minutes and at room temperature for 3 hours. After saturated aqueous ammonium chloride was added, the reaction solution was extracted with ethyl acetate, and the organic layer was washed with saturated saline. After dried over anhydrous sodium sulfate, the organic layer was concentrated under reduced pressure, and the resulting residue was purified by silica gel column chromatography (hexane/ethyl acetate/methanol=5/5/1) whereby the title compound (572 mg, quant.) was obtained as pale yellow solid.
$^1$H-NMR (CDCl$_3$); 1.85–2.07 (2H, m), 2.50 (1H, dt, J=7.2, 17.9 Hz), 2.78 (1H, dt, J=7.1, 17.9 Hz), 2.96–3.08 (2H, m), 3.90 (1H, d, J=4.6 Hz), 4.04–4.28 (5H, complex), 4.38 (2H, s), 4.58–4.75 (1H, m), 6.58 (1H, d, J=9.5 Hz), 6.60 (1H, d, J=8.4 Hz), 6.81 (1H, ddd, J=0.9, 5.0, 7.1 Hz), 7.10–7.59 (16H, complex), 7.82–8.00 (1H, br, s), 8.09–8.07 (1H, m), 8.18 (1H, s):MS;m/z=696 (M+1)
(3) 2-(5-Benzylsulfonylamino-6-oxo-2-phenyl-1,6-dihydropyrimidine-1-yl)-N-{2,3-dioxo-1-phenylmethyl-6-(2-pyridyloxy)}hexylacetamide (Compound No. 77)

2-(5-Benzylsulfonylamino-6-oxo-2-phenyl-1,6-dihydropyrimidine-1-yl)-N-{(1S,2R)-2-hydroxy-3-oxo-1-phenylmethyl-6-(2-pyridyloxy)}hexylacetamide (571.9 mg, 0.822 mmol) was dissolved in methylene chloride (1 ml) and dimethylsulfoxide (0.87 ml), followed by successively adding pyridinium trifluoroacetate (79.4 mg, 0.41 mmol) and 1-(3-dimethylaminopropyl)-3-ethylcarbodiimide hydrochloride (474 mg, 2.47 mmol), and the mixture was stirred at 0° C. for 30 minutes and at room temperature for 2 hours. After water was added, the reaction solution was extracted with ethyl acetate, and it was dried over anhydrous sodium sulfate. The organic layer was concentrated under reduced pressure, and the resulting residue was purified by silica gel column chromatography (methylene chloride/ethyl acetate= 1/1) whereby the title compound (80 mg, 14% yield) was obtained as pale yellow solid.
$^1$H-NMR (CDCl$_3$); 1.92–2.09 (m, 2H), 2.66–3.26 (4H, complex), 4.05–4.42 (6H, complex), 5.30–5.45 (1H, m), 6.63 (1H, d, J=6.6 Hz), 6.77–6.90 (1H, m), 6.96 (1H, d, J=7.0 Hz), 7.08–7.63 (16H, complex), 8.01–8.13 (2H, complex), 8.18 (1H, s):MS;m/z=694 (M+1).

Example 55

2-(5-Formylamino-6-oxo-2-phenyl-1,6-dihydropyrimidine- 1-yl)-N-{2,3-dioxo-1-phenylmethyl-6-(2-pyridyloxy)}-hexylacetamide (Compound No. 79) was synthesized in the following manner.
(1) 2-(5-Formylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (Compound No. 28)

Formic acid (0.12 ml, 3.2 mmol) was added to acetic anhydride (0.25 ml, 2.6 mmol) under cooling on ice and stirred at 60° C. for 2 hours. Thereafter, the mixture was cooled to −20° C., and a solution of the common intermediate 2-(5-amino-6-oxo-2-phenyl-1,6-dihydropyrimidine-1-yl)-N-{((1S,2R)-2-acetyloxy-3-oxo-1-phenylmethyl-6-(2-pyridyloxy)}hexylacetamide dihydrochloride (656 mg, 1.0 mmol) in a mixed solvent of tetrahydrofuran (2 ml) and triethylamine (0.29 ml, 2.1 mmol) was added to it, and the mixture was stirred for 1 hour during which the temperature was raised to 0° C. The reaction solution was concentrated as such under reduced pressure, and the resulting residue was purified by silica gel column chromatography (hexane/ethyl acetate/methanol=10/10/1) whereby the title compound (570 mg, 93% yield) was obtained as white solid.
$^1$H-NMR (CDCl$_3$); 1.92–2.09 (2H, m), 2.18 (3H, s), 2.49–2.71 (2H, m), 2.85 (1H, dd, J=8.8, 13.5 Hz), 3.00 (1H, dd, J=6.5, 13.5 Hz), 4.15–4.36 (2H, m), 4.48 (2H, dd, J=8.4, 15.3 Hz), 4.70–4.90 (1H, m), 4.98 (1H, d, J=2.2 Hz), 6.52 (1H, d, J=9.2 Hz), 6.69 (1H, dt, J=1.0, 8.3 Hz), 6.84 (1H, ddd, J=0.9, 5.1, 7.2 Hz), 7.10–7.61 (11H, complex), 8.08 (1H, ddd, J=7.0.8, 2.0, 5.1 Hz), 8.7 (1H, s), 8.49 (1H, s), 9.11 (1H, s):MS;m/z=612 (M+1)
(2) 2-(5-Formylamino-6-oxo-2-phenyl-1,6-dihydropyrimidine-1-yl)-N-{(1S,2R)-2-hydroxy-3-oxo-1- phenylmethyl-6-(2-pyridyloxy)}hexylacetamide (Compound No. 29)

2-(5-Formylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (570.4 mg, 0.93 mmol) was dissolved in methanol (3.7 ml), and an aqueous solution (1 ml) of potassium carbonate (3.87 mg) was added to it under cooling on ice, and the mixture was stirred at 0° C. for 30 minutes and at room temperature for 3 hours. After saturated aqueous ammonium chloride was added, the reaction solution was extracted with ethyl acetate and the organic layer was washed with saturated saline. After dried over anhydrous sodium sulfate, the organic layer was concentrated under reduced pressure whereby the title compound (379 mg, 71% yield) was obtained.
$^1$H-NMR (CDCl$_3$); 1.96–2.12 (2H, m), 2.55 (1H, dt, J=7.1, 18.0 Hz), 2.77 (1H, dt, J=7.0, 17.8 Hz), 2.97 (2H, d, J=7.9 Hz), 3.92 (d, J=3.7 Hz), 4.05–4.12 (1H, m), 4.14–4.48 (4H, complex), 4.64–4.82 (1H, m), 6.21 (1H, d, J=9.2 Hz), 6.64 (1H, d, J=8.4 Hz), 6.79–6.88 (1H, m), 7.15–7.58 (1 1H, complex), 8.07 (1H, dd, J=1.8, 5.2 Hz), 8.27 (1H, s), 8.44 (1H, s), 9.09 (1H, s):MS;mm/z=570 (M+1)

(3) 2-(5-Formylamino-6-oxo-2-phenyl-1,6-dihydropyrimidine-1-yl)-N-{2,3-dioxo-1-phenylmethyl-6-(2-pyridyloxy)}hexylacetamide (Compound No. 79)

2-(5-Formylamino-6-oxo-2-phenyl-1,6-dihydropyrimidine-1-yl)-N-{(1S,2R)-2-hydroxy-3-oxo-1-phenylmethyl-6-(2-pyridyloxy)}hexylacetamide (374 mg, 0.66 mmol) was dissolved in methylene chloride (0.7 ml) and dimethylsulfoxide (0.7 ml), and pyridinium trifluoroacetate (64 mg, 0.33 mmol) and 1-(3-dimethylaminopropyl)-3-ethylcarbodiimide hydrochloride (378 mg, 1.97 mmol) were added to it, and the mixture was stirred at room temperature for 1 hour. After water was added, the reaction solution was extracted with ethyl acetate and dried over anhydrous sodium sulfate. The organic layer was concentrated under reduced pressure, and the resulting residue was purified by silica gel column chromatography (methylene chloride/ethyl acetate=1/2) whereby the title compound (257 mg, 69% yield) was obtained.
$^1$H-NMR (CDCl$_3$); 2.00–2.16 (2H, m), 2.76–3.09 (3H, complex), 3.23 (1H, dd, 5.4, 14.1 Hz), 4.32 (2H, t, J=6.4 Hz), 4.50 (2H, d, J=1.3 Hz) 5.21–5.33 (1H, m), 6.50 (1H, d, J=6.6 Hz), 6.70 (1H, d, J=8.3 Hz), 6.85 (1H, ddd, J=0.9, 5.1, 7.1 Hz), 7.00–7.11 (2H, m), 7.14–7.65 (9H, complex), 8.10 (1H, ddd, J=0.7, 2.0, 5.0 Hz), 8.24 (1H, br, s), 9.10 (1H, s):MS;m/z=568 (M+1)

Example 56

2-(5-Benzylaminosulfonylamino-6-oxo-2-phenyl-1,6-dihydropyrimidine-1-yl)-N-{2,3-dioxo-1-phenylmethyl-6-(2-pyridyloxy)}hexylacetamide (Compound No. 82) was synthesized in the following manner.

(1) 2-(5-Benzylaminosulfonylamino-6-oxo-2-phenyl-1,6-dihydropyrimidine-1-yl)-N-{(1S,2R)-2-acetyloxy-3-oxo-1-phenylmethyl-6-(2-pyridyloxy)hexyl}acetamide (Compound No. 35)

2,6-Lutidine (0.62 ml, 5.32 mmol) and 1 M benzylaminosulfonyl chloride/tetrahydrofuran solution(1.52 ml, 1.52 mmol) were added to a solution of 2-(5-amino-6-oxo-2-phenyl-1,6-dihydropyrimidine-1-yl)-N-{(1S,2)-2-acetyloxy-3-oxo-1-phenylmethyl-6-(2-pyridyloxy)}hexylacetamide dihydrochloride (1.0 g, 1.52 mmol) in tetrahydrofuran (3 ml) under cooling on ice, and the mixture was stirred at 0° C. for 1 hour and at room temperature for 1 hour. After saturated aqueous sodium bicarbonate was added, the reaction solution was extracted with ethyl acetate, and it was washed with saturated saline. After dried over anhydrous sodium sulfate, the organic layer was concentrated under reduced pressure, and the resulting residue was purified with using hexane/ethyl acetate=1/1 to 0/1) whereby 2-(5-benzylaminosulfonylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (602 mg, 53% yield) was obtained.
$^1$H-NMR (CDCl$_3$); 1.91–2.02 (2H, m), 2.05 (3H, s), 2.44–2.71 (2H, m), 2.75–3.03 (2H, m), 4.14–4.29 (4H, complex), 4.41 (2H, s), 4.71–4.88 (1H, m), 4.97 (1H, d, J=2.1 Hz), 5.50 (1H, t, J=5.9 Hz), 6.47 (1H, d, J=9.4 Hz), 6.66 (1H, d, J=8.4 Hz), 6.78–6.86 (1H, m), 7.08–7.62 (17H, complex), 8.06 (1H, dd, J=1.5, 5.1 Hz), 8.15 (1H, s):MS; m/z=7S3 (M+1)

(2) 2-(5-Benzylaminosulfonylamino-6-oxo-2-phenyl-1,6-dihydropyrimidine-1-yl)-N-{(1S,2R)-2-hydroxy-3-oxo-1-phenylmethyl-6-(2-pyridyloxy)}hexylacetamide (Compound 36)

2-(5-Benzylaminosulfonylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (601 mg, 0.8 mmol) was dissolved in methanol (3.2 ml), and an aqueous solution (1 ml) of potassium carbonate (332 mg) was added to it under cooling on ice, and the mixture was stirred at 0° C. for 1 hour. After saturated aqueous ammonium chloride was added, the reaction solution was extracted with ethyl acetate and the organic layer was washed with saturated saline. After dried over anhydrous sodium sulfate, the organic layer was concentrated under reduced pressure, whereby the title compound (405 mg, 71%) was obtained.
$^1$H-NMR (CDCl$_3$); 1.84–2.02 (2H, m), 2.46 (1H, dt, J=7.2, 18.0 Hz), 2.78 (1H, dt, J=7.0, 17.9 Hz), 2.95 (2H, d, J=3.0 Hz), 4.02–4.18 (4H, m), 4.27 (2H, s), 4.34–4.43 (1H, br, s), 4.50–4.75 (1H, m), 6.58 (1H, d, J=8.3 Hz), 6.73–6.87 (2H, complex), 7.12–7.54 (16H, complex), 8.01 (1H, ddd, J=0.7, 1.5, 5.1 Hz), 8.16 (1H, s) MS;m/z=711 (M+1)

(3) 2-(5-Benzylaminosulfonylamino-6-oxo-2-phenyl-1,6-dihydropyrimidine-1-yl)-N-{2,3-dioxo-1-phenylmethyl-6-(2-pyridyloxy)}hexylacetamide (Compound No. 82)

2-(5-Benzylaminosulfonylamino-6-oxo-2-phenyl-1,6-dihydropyrimidine-1-yl)-N-(1S,2R)-2-hydroxy-3-oxo-1-phenylmethyl-6-(2-pyridyloxy)}hexylacetamide (405 mg, 0.57 mmol) was dissolved in methylene chloride (0.6 ml) and dimethylsulfoxide (0.6 ml), followed by adding pyridinium trifluoracetate (55 mg, 0.29 mmol) and 1-(3-dimethylaminopropyl)-3-ethylcarbodiimide hydrochloride (328 mg, 1.71 mmol), and the mixture was stirred at room temperature for 1.5 hours. After water was added, the reaction solution was extracted with ethyl acetate and dried over anhydrous sodium sulfate. The organic layer was concentrated under reduced pressure, and the resulting residue was purified by silica gel column chromatography (methylene chloride/ethyl acetate=1/1) whereby the title compound (180 mg, 45% yield) was obtained.
$^1$H-NMR (CDCl$_3$); 1.95–2.10 (2H, m), 2.68–2.92 (2H, m), 2.99 (1H, dd, J=7.7, 14.0 Hz), 3.18 (1H, dd, J=5.6, 14.1 Hz), 4.21–4.29 (4H, complex), 4.46 (2 h, s), 5.24–5.34 (1H, m), 5.47 (1H, t, J=6.1 Hz), 6.64–6.72 (2H, complex), 6.83 (1H, ddd, J=0.9,–5.1, 7.2 Hz), 7.02–7.09 (1H, m), 7.14–7.66 (16H, complex), 8.06–8.11 (1H, m), 8.15 (1H, s):MS;m/z= 709 (M+1)

Example 57

Synthesis of 2-{6-oxo-2-phenyl-5-(4-pyridylmethyloxycarbonylamino)-1,6-dihydropyrimidine- 1-yl)-N-{2,3-dioxo-1-phenylmethyl-6-(2-pyridyloxy)}hexylacetamide (Compound No. 78) was conducted in the following manner.

(1) 2-{6-oxo-2-phenyl-5-(4-pyridylmethyloxycarbonylamino)-1,6-dihydropyrimidine-1-yl}-N-{(1S,2R)-2-acetyloxy-3-oxo-1-phenylmethyl-6-(2-pyridyloxy)}hexylacetamide (Compound No. 26)

A solution of triphosgene (445 mg, 1.5 mmol) in methylene chloride (1 ml) was added slowly to a solution of the common intermediate 2-(5-amino-6-oxo-2-phenyl-1,6-dihydropyrimidine-1-yl)-N-{(1S,2R)-2-acetyloxy-3-oxo-1-phenylmethyl-6-(2-pyridyl-oxy)}hexylacetamide dihydrochloride (656.5 mg, 1.0 mmol) in methylenechloride (10 ml) under cooling on ice under argon atmosphere, and the mixture was stirred for 45 minutes. Further, 4-pyridine methanol (349 mg, 3.2 mmol) was added to it, and the mixture was stirred at 0° C. for 1 hour and at room temperature overnight. After saturated aqueous sodium bicarbonate was added, the reaction solution was extracted with ethyl acetate, and it was washed with saturated saline. After dried over anhydrous sodium sulfate, the organic layer was concentrated under reduced pressure, and the resulting residue was purified by silica gel column chromatography (ethyl acetate/methanol=20/1) whereby 2-{6-oxo-2-phenyl-5-(4-pyridylmethyl)oxycarbonylamino-1,6-dihydropyrimidine-1-yl}-N-{(1S,2R)-2-acetyloxy-3-oxo-1-phenylmethyl-6-(2-pyridyloxy)}hexylacetamide (544 mg, 76%) was obtained as white solid.

$^1$H-NMR (CDCl$^3$); 1.92–2.10 (2H, m), 2.19 (3H, s), 2.46–2.67 (2H, m), 2.84 (1H, dd, J=8.5, 13.7 Hz), 2.98 (1H, dd, J=6.6, 13.6 Hz), 4.25 (2H, dt, J=1.1, 6.2 Hz), 4.47 (2H, d, J=3.3 Hz), 4.74–4.89 (1H, m), 4.98 (1H, d, J=2.1 Hz), 5.23 (2H, s), 6.35 (1H, d, J=9.2 Hz), 6.67 (1H, d, J=8.4 Hz), 6.82 (1H, ddd, J=0.9, 5.2, 7.1 Hz), 7.11–7.63 (13H, complex), 8.04–8.11 (1H, m), 8.62 (1H, dd, J=1.6, 4.5 Hz), 8.76 (1H, br, s):MS;m/z=719 (M+1)

(2) 2-{6-oxo-2-phenyl-5-(4-pyridylmethyloxycarbonylamino)-1,6-dihydropyrimidine-1-yl}-N-{(1D,2S)-2-hydroxy-3-oxo-1-phenylmethyl-6-(2-pyridyloxy)}hexylacetamide (Compound 27)

The title compound was synthesized in the same manner as in Example 56(2) using 2-{6-oxo-2-phenyl-5-(4-pyridylmethyloxycarbonylamino)-1,6-dihydropyrimidine-1-yl}-N-{(1S,2R )-2-acetyloxy-3-oxo-1-phenylmethyl-6-(2-pyridyloxy)}hexylacetamide as the starting material.

$^1$H-NMR (CDCl$_3$); 1.91–2.16 (2H, m), 2.40–2.91 (2H, m), 2.97 (2H, d, J=8.1 Hz), 3.88 (1H, d, J=3.7 Hz), 4.03–4.11 (1H, br, s), 4.18–4.32 (2H, m), 4.33 (1H, d, J=15.5 Hz), 4.48 (1H, d, J=15.3 Hz), 4.64–4.82 (1H, m), 5.23 (2H, s), 6.24 (1H, d, J=9.4 Hz), 6.62 (1H, d, J=8.3 Hz), 6.77–6.89 (1H, m), 7.15–7.65 (14H, complex), 8.06 (1H, dd, J=1.8, 5.1 Hz), 8.62 (1H, dd, J=1.6, 4.5 Hz), 8.76 (1H, s):MS;m/z=677 (M+1).

2-{6-oxo-2-phenyl-5-(4-pyridylmethyloxycarbonylamino)-1,6-dihydropyrimidine-1-yl}-N-{2,3-dioxo-1-phenylmethyl-6-(2-pyridyloxy)}hexylacetamide (Compound 78)

(3) The title compound was synthesized in the same manner as in Example 56(3) using 2-{6-oxo-2-phenyl-5-(4-pyridylmethyloxycarbonylamino)-1,6-dihydropyropyrimidine-1-yl}-N-{(1S,2R)-2-hydroxy-3-oxo-1-phenylmethyl-6-(2-pyridyloxy)}hexylacetamide as the starting material.

$^1$H-NMR (CDCl$_3$); 2.01–2.16 (2H, m), 2.74–3.09 (3H, complex), 3.22 (1H, dd, J=5.5, 14.0 Hz), 4.31 (2H, t, J=6.2 Hz), 4.50 (2H, s), 5.24 (2H, s), 5.26–5.38 (1H, m), 6.59 (1H, d, J=6.8 Hz), 6.64–6.74 (1H, m), 6.84 (1H, ddd, J=0.9, 6.0, 7.2 Hz), 7.00–7.69 (14H, complex), 8.06–8.14 (1H, m), 8.62 (1H, dd, J=1.6, 4.5 Hz), 8.75 (1H, s):M;m/z=675 (M+H)

Example 58

Synthesis of 2-(5-acetylamino-6-oxo-2-phenyl-1,6-dihydropyrimidine-1-yl)-N-{2,3-dioxo-1-phenylmethyl-6-(2-pyridyloxy)}hexylacetamide (Compound No. 80) was conducted in the following manner.

(1) 2-(5-Acetylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide (Compound No. 30)

The common intermediate, 2-(5-amino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide dihydrochloride (0.62 g, 1.0 mmol), was suspended in a mixed solvent of tetrahydrofuran (3 ml) and methylene chloride (2 ml), and triethylamine (0.44 ml, 3.2 mmol) and acetylchloride (0.08 ml, 1.1 mmol) were added to it under cooling on ice and stirred at room temperature for 2 hours. After acetyl chloride (0.03 ml) was added and the mixture was further stirred for 1 hour, the reaction solution was diluted with ethyl acetate, and it was washed successively with distilled water and saturated saline. The organic layer was dried over anhydrous sodium sulfate and then concentrated under reduced pressure, and the resulting residue was purified by silica gel column chromatography (hexane/ethyl acetate/methanol=10/10/1) whereby the title compound (506 mg, 81% yield) was obtained.

$^1$H-NMR (CDCl$_3$); 1.93–2.10 (2H, m), 2.19 (3H, s), 2.21 (3H, s), 2.49–2.69 (2H, m), 2.77–3.04 (2H, m), 4.24 (2H, t, J=6.3 Hz), 4.46 (2H, d, J=4.5 Hz), 4.74–4.89 (1H, m), 4.98 (1H, d, J=2.2 Hz), 6.34 (1H, d, J=9.2 Hz), 6.68 (1H, d, J=8.3 Hz), 6.82 (1H, ddd, J=1.0, 5.1, 6.0 Hz), 7.12–7.58 (1H, complex), 8.01 (1H, br. s), 8.05–8.10 (1H, m), 9.09 (1H, m): MS:m/z=626 (M+1)

(2) 2-(5-Acetylamino-6-oxo-2-phenyl-1,6-dihydropyrimidine-1-yl)-N-{(1S,2R)-2-hydroxy-3-oxo-1phenylmethyl-6-(2-pyridyl oxy)}hexylacetamide (Compound No. 31)

The title compound was synthesized in the same manner as in Example 56(2) using 2-(5-acetylamino-6-oxo-2-phenyl-1,6-dihydropyrimidine-1-yl)-N-{(1S,2R)-2-acetyloxy-3-oxo-1-phenylmethyl-6-(2-pyridyloxy)}hexylacetamide as the starting material.

$^1$H-NMR (CDCl$_3$); 1.96–2.13 (2H, m), 2.21 (3H, s), 2.45–2.89 (2H, m), 2.98 (2H, d, J=8.1 Hz), 3.89 (1H, d, J=3.8 Hz), 4.09 (1H, d, J=3.4 Hz), 4.18–4.52 (4H, complex), 4.65–4.80 (1H, m), 6.24 (1H, d, J=9.5 Hz), 6.63 (1H, d, J=8.3 Hz), 6.83 (1H, ddd, J=0.98, 5.1, 6.0 Hz), 7.06–7.60 (11H, complex), 8.01 (1H, br. s), 8.04–8.10 (1H, m), 9.09 (1H, s): MS (FAB) m/z=584 (M+1)

(3) 2-(5-Acetylamino-6-oxo-2-phenyl-1,6-dihydropyrimidine1-yl)-N-{2,3-dioxo-1-phenylmethyl-6-(-2-pyridyloxy)}hexyl-acetamide (Compound 80)

The title compound was synthesized in the same manner as in Example X4(3) using 2-(5-acetylamino-6-oxo-2-phenyl-1,6-dihydropyrimidine-1-yl)-N-{(1S,2R)-2-hydroxy-3-oso-1-phenylmethyl-6-(2-pyridyloxy)}hexylacetamide as the starting material.

$^1$H-NMR (CDCl$_3$); 2.00–2.18 (2H, m), 2.21 (3H, s), 2.75–3.28 (4H, complex), 4.31 (2H, t, J=6.2 Hz), 4.50 (2H, s), 5.27–5.39 (1H, m), 6.57 (1H, d, J=6.5 Hz), 6.69 (1H, d, J=8.4 Hz), 6.85 (1H, ddd, J=0.93, 4.0, 7.1 Hz), 7.01–7.09 (2H, complex), 7.15–7.30 (3H, complex), 7.35–7.61 (6H, complex), 7.98 (1H, br. s), 8.10 (1H, ddd, J=0.77, 2.0, 6.0 Hz) 9.08 (1H, s):MS;m/z=582 (M+1)

Example 59

Synthesis of 2-(5-acetylamino-6-oxo-2-phenyl-1,6-dihydropyrimidine-1-yl)-N-{(2,3-dioxo-6-(2-oxo-1,2-dihydropyridine-1-yl)-1-phenylmethyl}hexylacetamide (Compound No. 76) was conducted in the following manner.

(1) 1-Allyl-5-amino-6-oxo-2-phenyl-1,6-dihydropyrimidine

4 N hydrogen chloride/dioxane (31 ml, 122.2 mmol) was added to a solution of 1-allyl-5-t-butyloxycarbonylamino-6-oxo-2-phenyl-1,6-dihydropyrimidine (2 g, 6.11 mmol) in methanol (12 ml) under cooling on ice and stirred at 0° C. for 30 minutes and at room temperature overnight. The reaction solution was concentrated under reduced pressure whereby the title compound (1.49 g, 93%) was obtained as white solid.

$^1$H-NMR (CD$_3$OD); 4.62 (2H, dt, J=1.6, 3.5 Hz), 4.90–5.06 (1H, m), 5.18–5.27 (1H, m), 5.77–5.97 (1H, m), 7.68 (1H, s), 7.57–7.82 (5H, m)

(2) 5-Acetylamino-1-allyl-6-oxo-2-phenyl-1,6-dihydropyrimidine

1-Allyl-5-amino-6-oxo-2-phenyl-1,6-dihydropyrimidine hydrochloride was dissolved in tetrahydrofuran (27 ml) and triethylamine (1.16 ml, 8.33 mmol), and acetyl chloride (0.284 ml, 3.99 mmol) was added to it under cooling on ice, and the mixture was stirred at 0° C. for 30 minutes and at room temperature for 2 hours. After saturated aqueous sodium bicarbonate was added, the reaction solution was extracted with ethyl acetate, and it was washed with saturated saline. After dried over anhydrous sodium sulfate, the organic layer was concentrated under reduced pressure, and the resulting residue was purified by silica gel column chromatography (hexane/ethyl acetate=1/2) whereby the title compound (617 mg, 69%) was obtained.

$^1$H-NMR (CDCl$_3$); 2.24 (3H, s), 4.59 (2H, dt, J=1.6, 5.2 Hz), 4.8 8–5.0 2 (1H, m), 5.18–5.27 (1H, m), 5.86 (1H, ddt, J=5.2, 10.3, 17.2 Hz), 7.48 (5H, s), 8.05 (1H, br, s), 9.07 (1H, s):MS;m/z=270 (M+H), 539 (2M+H)

(3) 3-(5-Acetylamino-6-oxo-2-phenyl-1,6-dihydropyrimidine-1-yl)-1,2-propanediol

50% aqueous N-methylmorpholine-N-oxide (1.55 ml, 6.6 mmol) and 0.157 N aqueous osmium tetroxide (1.06 ml, 0.165 mmol) were added to a solution of 5-acetylamino-1-allyl-6-oxo-2-phenyl-1,6-dihydropyrimidine (888.6 mg, 3.3 mmol) in tetrahydrofuran (13 ml), and the mixture was stirred at room temperature for 2 days. After saturated aqueous sodium thiosulfate was added, the reaction solution was extracted with ethyl acetate, and the organic layer was washed with saturated saline. After dried over anhydrous sodium sulfate, the organic layer was concentrated under reduced pressure, and the resulting residue was purified by silica gel column chromatography (methylene chloride/methanol=10/1) whereby the title compound (1.06 g, quant) was obtained as white solid. $^1$H-NMR (CDCl$_3$); 2.25 (3H, s), 2.40–2.58 (1H, m), 3.29–3.63 (3H, complex), 3.78–3.95 (1H, m), 4.08–4.26 (2H, m), 7.41–7.54 (5H, s), 8.04 (1H, m), 9.00 (1H, s); MS (FAB) m/z=304 (M+1)

(4) (5-Acetylamino-6-oxo-2-phenyl-1,6-dihydropyrimidine-1-yl)acetaldehyde

An aqueous solution (11.2 ml) of sodium periodate (897 mg, 4.19 mmol) was added to a solution of 3-(5-acetylamino-6-oxo-2-phenyl-1,6-dihydropyrimidine-1-yl)-1,2-propanediol (1.06 g, 3.50 mmol) in tetrahydrofuran (100 ml), and the mixture was stirred overnight at room temperature. The reaction solution was concentrated as such, and after water was added, the product was extracted 3 times with ethyl acetate, and it was washed with saturated saline. After dried over anhydrous sodium sulfate, the organic layer was concentrated under reduced pressure whereby the title compound (800 mg, 84%) was obtained as white solid.

$^1$H-NMR (CDCl$_3$); 2.23 (3H, s), 4.80 (2H, s), 7.38–7.57 (5H, m), 7.95 (1H, br, s), 9.11 (1H, s), 9.61 (1H, s):MS;m/z=272 (M+1).

(5) (5-Acetylamino-6-oxo-2-phenyl-1,6-dihydropyrimidine-1-yl) acetic acid

2-Methyl-2-butene (1.38 ml, 12.98 mmol), an aqueous solution (4.2 ml) of sodium dihydrogen phosphate.1H$_2$O (419 mg, 2.95 mmol) and an aqueous solution (9.3 ml) of sodium chlorite (934 mg, 10.32 mmol) were added to a solution of (5-acetylamino-6-oxo-2-phenyl-1,6-dihydropyrimidine-1-yl)acetaldehyde(800mg,2.95 mmol) in2-methyl-2-propanol (14.8 ml), and the mixture was stirred overnight at room temperature. The reaction solution was washed with diethyl ether, and then the aqueous layer was adjusted to pH, 4 with citric acid and extracted 6 times with methylene chloride. After dried over anhydrous sodium sulfate, the organic layer was concentrated under reduced pressure whereby 5-acetylamino-6-oxo-2-phenyl-1,6-dihydro-1-pyrimidyl acetic acid (537 mg, 63%) was obtained as white solid.

$^1$H-NMR (CDCl$_3$); 2.23 (3H, s), 4.20–4.80 (1H, br, s), 4.64 (2H, s), 7.45–7.55 (5H, br, s), 8.16 (1H, s), 9.11 (1H, s):MS;m/z=288 (M+1), 575 (2M+1)

(6) Synthesis of 2-(5-acetylamino-6-oxo-2-phenyl-1,6-dihydropyrimidine-1-yl)-N-{(1S,2R)-2-hydroxy-3-oxo-6-(2-oxo-1,2-dihydropyridine-1-yl)-1-phenylmethyl}hexylacetamide (Compound No. 21) was conducted in the following manner.

(4R,5S)-5-{1-oxo-4-(2-oxo-1,2-dihydropyridine-1-yl)butyl}-3-(N-t-butyloxycarbonyl)-2,2-dimethyl-4-phenylmethyloxazolidine (Intermediate No. 12) (684 mg, 1.5 mmol) was dissolved in methanol (7.5 ml), and p-toluenesulfonic acid.1H$_2$O (573 mg, 3.0 mmol) was added to it, and the mixture was heated for 1.5 hours under reflux. The reaction solution was concentrated under reduced pressure, and the resulting residue was dissolved in a mixed solvent of N,N-dimethylformamide (7.5 ml) and tetrahydrofuran (7.5 ml), followed by successively adding (5-acetylamino-6-oxo-2-phenyl-1,6-dihydropyrimidine-1-yl)acetic acid (400 mg, 1.4 mmol), 1-hydroxybenzotriazole.1H$_2$O (245 mg, 1.8 mmol), 1-(3-dimethylaminopropyl)-3-ethylcarbodiimide hydrochloride (347 mg, 1.8 mmol), and N-methylmorpholine (0.46 ml, 4.5 mmol) under cooling on ice, and then the temperature was raised to room temperature and the mixture was stirred overnight. The reaction solution was diluted with ethyl acetate, and it was washed successively with 10% aqueous citric acid, saturated aqueous sodium bicarbonate, distilled water and saturated saline. The organic layer was dried over anhydrous sodium sulfate and concentrated under reduced pressure, and ethyl acetate/methanol/diethyl ether were added to the resulting residue so that the solid was precipitated. The precipitated solid was collected whereby the title compound (536 mg, 66% yield) was obtained.

$^1$H-NMR (CDCl$_3$); 1.88–2.07 (2H, m), 2.22 (3H, s), 2.46 (1H, dt, J=7.0, 18.6 Hz), 2.77 (1H, dt, J=6.8, 18.4 Hz), 2.98 (21H, d, J=7.7 Hz), 3.78–4.02 (2H, m), 4.02–4.06 (1H, m), 4.17 (1H, d, J=4.8 Hz), 4.46 (2H, s), 4.55–4.72 (11H, m), 6.16 (1H, dt, J=1.3, 6.7 Hz), 6.48 (1H, d, J=8.5 Hz), 6.56 (1H, d, J=9.2 Hz), 7.16–7.55 (12H, complex), 8.29 (1H, s), 9.06 (1H, s):MS;m/z=584 (M+1), 1167 (2M+1)

(7) 2-(5-Acetylamino-6-oxo-2-phenyl-1,6-dihydropyrimidine-1-yl)-N-{(2,3-dioxo-6-(2-oxo-1,2-dihydropyridine-1yl)-1-phenylmethyl}hexylacetamide (Compound No. 76)

The title compound was synthesized in the same manner as in Example 56(3) using 2-(5-acetylamino-6-oxo-2-phenyl-1,6-dihydropyrimidine-1-yl)-N-{(1S,2R)-2-acetyloxy-3-oxo-6-(2-oxo-1,2-dihydropyridine-1-yl)-1-phenylmethyl}hexyl-acetamide {in formula (II), R$^0$=phenyl, R$^1$=phenyl, R$^2$=(2-oxo-1,2-dihydropyridine-1-yl)propyl, R$^3$=acetyl, X=carbon, Y=nitrogen, Z=methylene} as the starting material.

$^1$H-NMR(CDCl$_3$); 1.88–2.14 (2H, m), 2.21 (31H, s), 2.60–2.91 (2H, m), 3.00 (1H, dd, J=8.1, 13.9 Hz), 3.21 (1H, dd, J=5.9, 14.1 Hz), 3.89 (2H, t, J=7.1 Hz), 4.51 (2H, d, J=1.9 Hz), 5.02–5.15 (1H, m), 6.17 (1H, dt, J=1.3, 6.6 Hz), 6.46 (1H, d, J=8.9 Hz), 7.10–7.53 (12H, complex), 7.83 (1H, d, J=6.6 Hz), 8.35 (1H, s), 9.02 (1H, s):MS;m/z=582 (M+1)

Example 60

The following compounds were synthesized according to Example 1 or the other examples previously described.

That is, the same procedure as in Example 1(3) was conducted for the oxidation reaction of the corresponding alcohol of formula (II) to give the compounds of formula (I) wherein R$^1$ is phenyl, R$^3$ is t-butyloxycarbonyl, X is carbon, Y is nitrogen, Z is methylene, R$^0$ and R$^2$ are the following groups.

The physical properties of the compounds of formula (I) are as follows.

(1) R$^0$=phenyl, R$^2$=benzylamino (Compound No. M1);
$^1$H-NMR (DMSO-d6): 1.48 (9H, s)N 2.8 6 (1H, dd, J=8.5, 13.9 Hz), 3.10 (1H, dd, J=4.1, 13.9 Hz), 4.35 (1H, d, J=6.4 Hz), 4.47 (1H, d, J=3.3 Hz), 5.26 (1H, ddd, J=4.1 Hz, 6.9, 8.5 Hz), 6.98–7.57 (15H, complex), 8.02 (1H, s), 8.40 (1H, s), 8.67 (1H, d, J=6.9 Hz), 9.28 (1H, t, J=6.4 Hz); MS:m/z=610 (M+1).

(2) : R$^0$=4-methoxyphenyl, R$^2$=methoxy (Compound No. M2);
$^1$H-NMR (CDCl$_3$): 1.54 (9H, s), 3.02 (1H, dd, J=6.4, 14.2 Hz), 3.20 (1H, dd, J=5.9, 14.2 Hz), 3.75 (3H, s), 3.89 (3H, s), 4.50 (2H, d, J=2.2 Hz), 5.43 (1H, dd, J=6.4, 13.3 Hz), 6.49 (1H, d, J=7.0 Hz), 6.77 (2H, d, J=8.8 Hz), 6.97 (2H, d, J=8.8 Hz), 7.27 (solvent peak, over lapped with 1H), 7.46 (5H, s), 8.72 (1H, s).

Example 61

The following compounds were synthesized according to Example 1 or the other examples previously described.

That is, the same procedure as in Example 1(4) was conducted for the deprotection of the compounds of formula (I) wherein R$^3$ is a t-butyloxycarbonyl group to give the corresponding hydrochlorides of the compounds of formula (I) wherein R$^3$is hydrogen, R$^1$ is phenyl, X is carbon, Y is nitrogen, Z is methylene, R$^0$ and R$^2$ are the groups described below.

(1): R$^0$=phenyl, R$^2$=benzylamino (Compound No. M3);
$^1$H-NMR (CDCl$_3$): 2.73–2.90 (1H, m), 3.0 4–3.16 (1H, m), 4.28–4.50 (4H, m), 5.20–5.35 (1H, m), 7.01–7.51 (16H, complex), 8.61 (1H, d, J=7.0 Hz), 9.28 (1H, t, J=6.3 Hz);MS:m/z=510 (M+1)

(2): R$^0$=4-methoxyphenyl, R$^2$=methoxy (Compound No. M4);
$^1$H-NMR (DMSO-d6): 2.77 (1H, dd, J=8.6, 14.1 Hz), 3.02 (1H, dd, J=5.4, 14.1 Hz), 3.57 (3H, s), 4.35–4.97 (solvent peak, overlapped with 3H), 6.80 (2H, d, J=8.6 Hz), 7.50 (2H, d, J=8.6 Hz), 7.34–7.62 (5H, complex, overlapped with 1H), 9.06 (1H, d, J=6.5 Hz).

Example 62. Pharmaceutical Composition Example (Injection)

Purified water was added to 30 parts by weight of the present compound and 18 parts by weight of sodium chloride (100 parts by weight of glucose) to give a solution of a total volume of 2000 parts by weight and then filtered through Millipore filter GS type to remove bacteria. 2 g of the filtrate was pipetted to a vial and capped to give an injection containing 30 mg of the present compound.

Example 63.Pharmaceutical Composition Example (Tablets)

10 parts by weight of the present compound, 30 parts by weight of potato starch, 150 parts by weight of crystalline lactose, 108 parts by weight of crystalline cellulose and 2 parts by weight of magnesium stearate were mixed in a V-shaped mixer and tabletted at 60 mg per tablet to give tablets each containing 2 mg of the present compound.

Hereinafter, the bioactivity of the present compounds is specifically described with reference to Test Examples.

Test Example 1

(1) Inhibitory activity on chymase

It is known that chymase is present in tissues of various animals, and its isolation and purification methods are described in Anal. Biochem., 137, 449 (1984) and FEBS Letters, 323, 119 (1993). In the present invention, chymase was purified by the methods described in these literatures, and the present compounds were examined for inhibitory activity on chymase, inhibitory action on activation of mast cells and eosinophils, and pharmacological action in animals. Hereinafter, specific methods are described.

(A) Preparation of rat chymase 50 g rat tongue was finely divided by scissors and a scalpel, suspended in 0.1 M phosphate buffer (pH 8.0), and disrupted by a Polytron homogenizer for 5 minutes to prepare a crude chymase enzyme solution. It was centrifuged at 23500×g for 20 minutes, and the precipitates were used as a chymase enzyme fraction. The precipitates were washed by repeating the above procedure twice, then suspended in 0.1 M phosphate buffer (pH 8.0) containing 2 M sodium chloride and 5% ammonium sulfate, and centrifuged at 100000×g for 45 minutes to give a supernatant as a chymase fraction. The supernatant was applied to an octyl Sepharose 4B column (40×100 mm) previously equilibrated with 0.1 M phosphate buffer (pH 8.0) containing 2 M sodium chloride and 5% ammonium sulfate, and the protein was eluted with a linear concentration gradient of from 2 M to 0 M sodium chloride. An active fraction decomposing succinyl leucyl leucyl valyl tyrosyl methylcumarylamide (hereinafter referred to as the synthetic chymase substrate, a product of Peptide Kenkyusho) was recovered and concentrated and this product was used as a purified rat chymase in the following activity measurement. (B) Preparation of human chymase 60 g human tonsils were finely divided by scissors and a scalpel, suspended in 0.1 M phosphate buffer (pH 8.0), and A-disrupted by a Polytron homogenizer for 5 minutes to prepare a crude chymase enzyme solution. It was centrifuged at 22000×g for 30 minutes, and the precipitates were used as a chymase enzyme fraction. The precipitates were washed by repeating the above procedure twice, then suspended in 0.1 M phosphate buffer (pH 8.0) containing 2 M sodium chloride and 5% ammonium sulfate, and centrifuged at 27000×g for 20 minutes to give a supernatant as a chymase fraction. The supernatant was concentrated by an ultrafiltration membrane, then applied to a G2000 SW-XL column (6.0×300 mm), and eluted with 0.1 M phosphate buffer (pH 8.0). An active fraction decomposing the synthetic chymase substrate was recovered and concentrated and this product was used as a purified human chymase in the following activity measurement.

(c) Preparation of dog chymase 60 g dog heart was finely divided by scissors and a scalpel, suspended in 0.1 M phosphate buffer (pH 8.0), and disrupted by a Polytron homogenizer for 5 minutes to prepare a crude chymase enzyme solution. It was centrifuged at 22000×g for 15 minutes, and the precipitates were used as a chymase enzyme fraction. The precipitates were washed by repeating the above procedure twice, then suspended in 0.1 M phosphate buffer (pH 8.0) containing 2 M sodium chloride and 5% ammonium sulfate, and centrifuged at 27000×g for 40 minutes to give a supernatant as a chymase fraction. For removal of macromolecular compounds and concentration, the chymase fraction was passed through an ultrafiltration membrane, and the concentrate was then applied to a Superdex 200HR 10/30 column (10×300 mm) and eluted with 0.1 M phosphate buffer (pH 8.0). An active fraction decomposing the synthetic chymase substrate was recovered and concentrated and this product was used as a purified dog chymase in the following activity measurement.

(D) Measurement of inhibitory activity on chymase (a) Measurement using the synthetic substrate The synthetic chymase substrate was used for measurement of the inhibitory activity on the rat chymase as a subtrate, and the fluorescence of formed aminomethylcoumarin after reaction was measured by a spectrophotometer. That is, 200 µl of 0.15 M Tris-HCl buffer (pH 8.0) containing 0.1 mM the synthetic chymase substrate, 0.0002 µl rat chymase solution and 2 µl of the present compounds in dimethylsulfoxide solution were added into a 0.5 ml measurement cuvette and incubated at 37° C. for 15 minutes. After the end of the reaction, produced aminomethylcoumarin was immediately measured at an excitation wavelength of 370 nm and a detection wavelength of 460 nm to determine the activity of the chymase, and the 50% inhibitory concentration (IC50: nM) was calculated.

(b) Measurement using angiotensin I as substrate

The inhibitory activity on the human chymase and dog chymase was measured using angiotensin I (Peptide Kenkyusho) as substrate besides the above synthetic substrate. That is, 200 µl of 0.15 M Tris-HCl buffer (pH 8.0) containing 0.1 mM angiotensin I, 0.0002 µl human or dog chymase solution and 2 µl of the present compounds in dimethylsulfoxide solution were added into a 1.5 ml test tube and incubated at 37° C. for 60 minutes. After the end of the reaction, produced angiotensin II was immediately measured by high performance liquid chromatography to determine the activity of the chymase to calculate 50% inhibitory concentration (IC50: nM).

(E) Measurement of inhibitory activity on proteases other than chymase

The inhibitory activity of the present compounds on human elastase, human cathepsin G, human urokinase, human thrombin, human plasmin, and human factor Xa was determined using their corresponding synthetic substrates in the same manner as for chymase. All the above proteases were those commercially available from Boehringer Mannheim or purified by a combination of known methods. The synthetic substrates were those produced by Peptide Renkyusho. The synthetic substrates for the respective proteases are as follows.

| Proteases | Synthetic Substrates |
| --- | --- |
| Human elastase | Succinyl alanyl propyl alanyl methylcoumarylamide |
| Human cathepsin G | Succinyl alanyl alanyl propyl phenylmethylcoumarylamide |
| Human urokinase | Pyridyl glycyl arginyl methylcoumarylamide |
| Human thrombin | Benzyloxycarbonyl asparginyl prolyl arginyl metylcoumarylamide |
| Human plasmin | Benzyloxycarbonyl valyl leucyl lyzyl methylcoumarylamide |
| Human factor Xa | Phenylmethyloxycarbonyl pyridyl glycyl arginyl methylcoumarylamide |

The test was conducted several times. Chymase was prepared for each test in the manner described above. The compounds examined were compounds prepared in the above-described examples. The 50% inhibitory concentration (IC50: nM) of each compound toward chymase and the other proteases was calculated, and the results are shown in Tables 13 and 14.

Table 13

50% Inhibitory concentration (IC50: nM) of each compound toward rat chymase, dog chyinase and human chyinase Substrate: Succinyl leucyl leucyl valyl tyrosyl methylcoumarylamide (for rat chymnase) and angiotensin I (for human and dog chymase)

| Compound No. | Rat Chymase (IC50: nM) | Dog Chymase (IC50: nM) | Human Chymase (IC50: nM) |
| --- | --- | --- | --- |
| 37 | 2900 | 22 | 673 |
| 40 | 46 | 13 | 190 |
| 41 | 740 | 13 | 148 |
| 44 | 79 | 16 | 146 |
| 46 | 2800 | 494 | 1587 |
| 48 | — | 33 | 314 |
| 50 | 690 | 19 | 73 |
| 52 | 190 | 27 | 120 |
| 54 | 45 | 3.6 | 36 |
| 69 | 54 | 24 | 302 |
| 72 | 2100 | 1.6 | 90 |
| 73 | 550 | 2.9 | 46 |
| 74 | 510 | 0.92 | 11 |
| 75 | 220 | 1.0 | 2.6 |
| 55 | 920 | 98 | — |
| 58 | 340 | 71 | 2851 |
| 60 | 450 | 9.1 | 101 |
| 62 | 200 | 5.0 | 131 |
| 76 | 190 | 0.19 | 122 |
| 77 | 48 | 1.4 | 7.0 |
| 78 | 42 | 0.32 | 1.6 |
| 79 | 19 | 0.32 | 2.4 |
| 80 | 52 | 0.35 | 0.90 |
| 81 | 150 | 0.29 | 114 |
| 82 | 19 | 0.14 | 0.74 |

("-" indicates that 50% inhibitory concentration (IC50: nM) is 10,000 nM or more.)

TABLE 14

50% Inhibitory concentration (IC50: µM) of each compound toward proteases other than chymase

| | Compound No. | | | | | | |
| --- | --- | --- | --- | --- | --- | --- | --- |
| Proteases | 40 | 52 | 72 | 74 | 79 | 80 | 82 |
| Human cathepsin G | — | 350 | 540 | 90 | 420 | 18 | 19 |
| Human elastase | 1900 | — | 5500 | 6000 | — | 2100 | 4000 |
| Human urokinase | — | — | — | — | — | — | — |
| Human thrombin | — | — | — | — | — | — | — |
| Human plasmin | — | — | — | — | — | — | — |
| Human factor Xa | — | — | — | — | — | — | — |

("-" indicates that 50% inhibitory concentration (IC50: nM) is 10,000 nM or more.)

As is evident from Tables 13 and 14, the compounds of the present invention inhibited rat chymase, dog chymase and human chymase at a low concentration of the compounds, and further exhibited selectivity between other proteases and chymase. Further, the activity of the human chymase and dog chymase was inhibited similarly at a low concentration, also using angiotensin I which is one of chymase substrates in vivo. Further, Compound 50, Compound 54, Compound 72, Compound 73, Compound 74, Compound 75, Compound 77, Compound 78, Compound 79, Compound 80 and Compound 82 had a strong inhibitory activity on human chymase but had no inhibitory activity on other human proteases, so they are expected as therapeutic agents having no side effects on thrombolysis, blood coagulation etc. In particular, the compounds in Table 14 have particularly highly potent in inhibitory activity on chymase and are thus considered as the most preferable compounds.

Test Example 2
Inhibitory action on degranulation of mast cells
(A) Preparation of mast cells 30 ml of mast cell buffer solution (150 mM sodium chloride, 3.7 mM potassium chloride, 3.0 mM disodium hydrogen phosphate, 3.5 mM sodium dihydrogen phosphate, 5.6 mM dextrose, pH 7.0) was injected into the abdomen of a rat(SD, male, 8 to 10 week-old), and intra peritoneal cavity cells were recovered and centrifuged at 800 rpm for 5 minutes, and then the abdomen infiltration cells were recovered as precipitates. The precipitated cells were further washed twice with the mast cell buffer solution, suspended again at a predetermined density, and used in the objective experiment.

(B) Inhibitory action on degranulation of mast cells (inhibitory action on histamine release from rat mast cells)

The mast cells obtained in the procedure in (A) above were suspended at $1 \times 10^5$ cells in the mast cell buffer solution and kept at 37° C. 2 μl of each drug and 200 μl of the cell suspension were added into a 1.5 ml test tube previously kept at 37° C. and incubated at 37° C. for 10 minutes. After incubation, 2 μl anti-IgE antibody (BETHYL Lab. Inc.) was added to it and further incubated at 37° C. for 15 minutes. After the end of the reaction, the reaction mixture was immediately cooled on ice and centrifuged at 4° C. at 4000 rpm for 5 minutes, and then the supernatant was stored. Histamine in the supernatant was modified with ortho-phthalaldehyde and measured by high performance liquid chromatography to determine 50% inhibitory concentration (IC50: μM). The results are shown in Table 15.

TABLE 15

50% Inhibitory concentration (IC50: μM) of each compound on histamine release from mast cells

| Compound | Inhibitory activity on histamine release (IC50: μM) |
|---|---|
| 40 | 1.8 |
| 44 | 14 |
| 52 | 50 |
| 54 | 35 |
| 71 | 13 |

Test Example 3
Inhibitory activity on eosinophil activation
(A) Preparation of eosinophils Polymyxin B (produced by Sigma) was administered intraperitoneally into a guinea pig (Hartley, male, 6-week-old) at a dosage of 1 mg once every week for 6 to 8 weeks. After the final administration of polymyxin B. 50 ml of PBS (phosphate-buffered saline) was injected into the intraperitoneal cavity of the guinea pig, and cells were recovered. The cells were centrifuged at 800 rpm for 5 minutes and the abdomen infiltration cells were collected as precipitates and then suspended in 1 ml of 40% Ficoll (40% Ficoll (produced by Pharmacia), HBSS (Hanks' balanced salt solution) and layered on a Ficoll discontinuous density gradient (40 to 90%). It was centrifuged at 1500 rpm for 40 minutes, and the eosinophil fraction was recovered. In this operation, eosinophils of 99% or more purity were usually obtained. Further, the cells were washed twice with RPMI 1640 medium (10% BSA (bovine serum albumin available from Boehringer Mannheim), suspended again at a predetermined density, and used in the objective experiment.

(B) Inhibitory action on eosinophils (inhibitory action on release of active oxygen from guinea pig eosinophils)

The eosinophils (99% or more purity) obtained by the Ficoll density gradient method in (A) above were suspended at a cell density of $4 \times 10^5$ in a buffer solution (0.136 M sodium chloride, 2.7 mM potassium chloride, 1.8 mM calcium chloride, 1.0 mM magnesium chloride, 11.9 mM sodium hydrogen carbonate, 5.5 mM D-glucose, 5.0 mM HEPES, 0.36 mM sodium dihydrogen phosphate, pH 7.2). Each drug (2 μl) and 180 μl of the cell suspension were put to a 96-well multi-well plate (for chemiluminescence measurement, white type) previously kept at 37° C., and incubated at 37° C. for 10 minutes. After incubation, 20 μl of PAF (platelet-activating factor) ($5 \times 10^{-6}$ M) and 20 μl of a luminol solution were added to it and immediately examined for its chemiluminescence (Luminoskan Labosystem). The chemiluminescence for 5 minutes were measured to calculate 50% inhibitory concentration (IC50: μM). The results are shown in Table 16.

TABLE 16

50% Inhibitory concentration (IC50: μM) of each compound on release of active oxygen from eosinophils

| Compound | Inhibitory activity on release of active oxyqen (IC50: μM) |
|---|---|
| 40 | 5.6 |
| 44 | 18 |
| 52 | 26 |
| 54 | 62 |
| 69 | 2.5 |
| 71 | 2.6 |
| 73 | 3.0 |

As can be seen from Tables 15 and 16, the present compounds having the inhibitory activity on chymase inhibited the activation of mast cells and eosinophils at a low concentration, and mast cells and eosinophils were simultaneously inhibited.

Industrially Applicability

As described above, the present compounds having the inhibitory activity on chymase inhibit not only rat chymase but also human chymase at a low concentration of the compounds without inhibiting other proteases. Further, the present compounds also inhibit the conversion of angiotensin I into angiotensin II by chymase, and have also inhibitory action on mast cell activation as well as inhibitory action on eosinophil activation, so they are expected as agents for treating or preventing diseases such as asthma, allergy, inflammations, rheumatism, hypertension, heart failure, myocardial infarction, cardiac hypertrophy, vascular injuries accompanied by angiogenesis and atheroma, nephritis and renal insufficiency etc.

What is claimed is:

1. Novel acetamide compounds represented by the following chemical formula (I) or pharmacologically acceptable salts thereof:

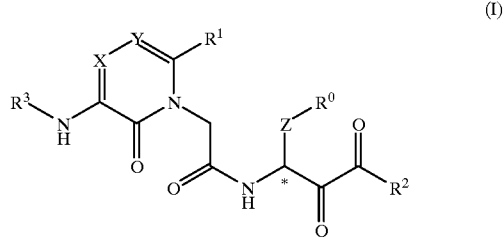

(I)

wherein $R^0$ is a phenyl group whose ring may have one or more substituent groups selected from group A defined below (group A; group A represents halogen, nitro, a hydroxyl group, a lower alkoxy group, a lower alkyl group, or a halogen-substituted lower alkyl group);

$R^1$ is (i) aryl or (ii) heteroaryl which may independently have one or more substituent groups defined with respect to group A; or $R^1$ may independently have one or more substituent groups selected from OH, COOH, $NH_2$, $CONH_2$, NHCHO and group B consisting of $OR_a$, $COOR_a$, $CONR_bR_c$, $NR_bR_c$, $NR_bCHO$ and $NR_b$-$COR_a$ on the above groups (i) or (ii) (among which $R_a$ to $R_c$ are independently lower alkyl or substituted lower alkyl; or $R_a$ to $R_c$ are independently aryl (1–7C) alkyl, heteroaryl (1–7C) alkyl, aryl and heteroaryl, among which the aryl or heteroaryl ring may have one or more, usually 1 to 3, substituent groups selected from the above-defined group A; the substituted lower alkyl has 1 to 3 atoms or groups selected from halogen and nitro group as substituent group; or $R^1$ may have one or more of the following defined cyclic group G on the above groups (i) or (ii) (cyclic group G; cyclic group G represents a heterocyclic group consisting of a 5- or 6-membered ring containing 1 to 3 oxygen or nitrogen atoms and may have a substituent group);

$R^2$ represents (1–8C) alkyl, aryl (1–7C) alkyl, heteroaryl (1–7C) alkyl, and aryl; or $R^2$ represents OH, $NH_2$, NHCHO, the above-defined group B or (1–8C) alkyl having group B as a substituent group; or (1–8C) alkyl having the above-defined cyclic group G as a substituent group;

$R^3$ is hydrogen; or $R^3$ is (i) $D(CH_2)_{0-3}CO$, (ii) DCOECO or (iii) $DSO_2ECO$ as an acyl group; or $R^3$ is $D(CH_2)_{0-3}SO_2$ or $DCOESO_2$ as a sulfonyl group (wherein group D represents hydrogen, a C1–6 straight-chain, branched or cyclic alkyl group, aryl group, halogeno lower alkyl, halogeno lower alkoxy, lower alkoxyamino, halogeno lower alkylamino, $R_bR_cN$, $R_bR_cNO$, $R_aO$, $R_a$, $R_aOCO$, $R_bR_cNCO$, $R_aSO_2NR_b$, $R_aS$ and the above-defined group G; and group E represents a divalent crosslinking group containing 1 to 6 carbon atoms); or $R^3$ is thiourea represented by $R_bR_cNCS$; or $R^3$ is $R_a$;

X represents a carbon atom, which may be substituted by groups represented by $R_a$ to $R_c$, and Y represents a nitrogen atom; and Z represents a polymethylene group wherein hydrogen atoms on the polymethylene group may independently be replaced by $R_a$ and $R_b$.

2. Novel acetamide compounds, represented by the formula(I), according to claim 1 or pharmacologically acceptable salts thereof, wherein $R^2$ represents the following:

$R^2$ is a (1–8C) alkyl, aryl (1–7C) alkyl, heteroaryl (1–7C) alkyl and aryl; or $R^2$ is the above-defined group B (provided that when Y is a nitrogen atom and X is a carbon atom in formula (I), $R^2$ represents groups other than $OR_a$ or $NR_bR_c$), or (1–8C) alkyl having the group B as a substituent group; or (1–8C) alkyl having the above-defined cyclic group G as a substituent group.

3. Novel acetamide compounds according to claim 1 or 2 or pharmacologically acceptable salts thereof, wherein the cyclic group G represents a group selected from the group consisting of pyridyloxy, 2-oxo-1,2-dihydro-pyridine-1-yl, pyrimidyloxy, pyrazyloxy, pyridazyloxy, piperazine-1-yl optionally having a lower alkyl or aryl lower alkyl group at the 4-position, pyrrolidine-1-yl, piperidine-1-yl, 4-morpholine-4-yl, and pyrrole-1-yl.

4. Novel acetamide compounds according to claim 1 or pharmacologically acceptable salts thereof, wherein $R^0$, $R^1$, $R^2$, $R^3$, X, Y and Z in formula (I) represent the following:

$R^0$ is a phenyl group whose ring may have 1 to 5 substituent groups selected from group A consisting of halogen, a hydroxyl group, a lower alkoxy group, a lower alkyl group, and a trifluoromethyl group;

$R^1$ is phenyl, thienyl, furyl, pyridyl or pyrrolyl which may independently have one or more substituent groups defined above for group A; or $R^1$ may have one or more substituent groups selected from OH, $NH_2$, COOH, $CONH_2$, NHCHO and group B consisting of $OR_a$, $COOR_a$, $CONR_bR_c$, $NR_bR_c$, $NR_bCHO$ and $NR_bCOR_a$ on the above phenyl, thienyl, furyl, pyridyl or pyrrolyl (among which $R_a$ to $R_c$ are independently lower alkyl; or $R_a$ to $R_c$ are independently aryl (1–7C) alkyl, heteroaryl (1–7C) alkyl, aryl and heteroaryl, wherein the aryl or heteroaryl ring may have one or more substituent groups selected from group A; or $R^1$ may have one or more of cyclic group G selected from the group consisting of pyridyloxy, 2-oxo-1,2-dihydropyridine-1-yl, pyrimidyloxy, pyrazyloxy, pyridazyloxy, piperazine-1-yl optionally having a lower alkyl or aryl lower alkyl group at the 4-position, pyrrolidine-1-yl, piperidine-1-yl, 4-morpholine-4-yl, 2-oxo-1,2-dihydropyridine-1-yl, and pyrrole-1-yl as a substituent group on the above phenyl, thienyl, furyl, pyridyl or pyrrolyl;

$R^2$ represents (1–4C) alkyl, aryl (1–3C) alkyl, heteroaryl (1–3C) alkyl, and aryl; or $R^2$ represents OH $NH_2$, NHCHO, the above-defined group B or (1–3C) alkyl having group B as a substituent group; or (1–3C) alkyl having the above-defined cyclic group G as a substituent group;

$R^3$ is hydrogen; or $R^3$ is (i) $D(CH_2)_{0-3}CO$, (ii) DCOECO or (iii) $DSO_2ECO$ as an acyl group; or $R^3$ is $D(CH_2)_{0-3}SO_2$ or $DCOESO_2$ as a sulfonyl group; or $R^3$ is thiourea represented by $R_bR_cNCS$; or $R^3$ is $R_a$ (wherein group D represents hydrogen, a C1–6 straight-chain, branched or cyclic alkyl group, trifluoromethyl, 2,2,2-trifluoroethoxy, methoxyamino, 2,2,2-trifluoroethylamino, $R_bR_cN$, $R_bR_cNO$, $R_a$ O, $R_a$, $R_a$ OCO, $R_bR_cNCO$, $R_a$ $SO_2NR_b$, $R_aS$ or the above-defined group G; Group E represents a divalent benzene nucleus, a divalent heteroaryl nucleus, 1,4-piperazine-di-yl, and a C1–6 straight-chain, branched or cyclic divalent aliphatic crosslinking group);

X represents a carbon atom, which may be substituted by groups represented by $R_a$ to $R_c$, and Y represents a nitrogen atom; and Z represents —$CH_2$— wherein the 2 hydrogen atoms may independently be replaced by $R_a$ and $R_b$.

5. Novel acetamide compounds according to claim 1 or 2 or pharmacologically acceptable salts thereof, wherein $R^0$, $R^1$, $R^2$, $R^3$, X, Y and Z in formula (I) represent the following:

$R^0$ is a phenyl group whose ring may have 1 to 3 substituent groups selected from halogen, a hydroxyl group, a lower alkoxy group a lower alkyl group, and a trifluoromethyl group as group A on the ring;

$R^1$ is a phenyl group which may independently have one or more of the above-defined group A on the ring; or $R^1$ may have one or more substituent groups selected from group B consisting of $OR_a$, $COOR_a$, $CONR_bR_c$, $NR_bR_c$, $NR_bCHO$ and $NR_bCOR_a$;

$R^2$ represents (1–4C) alkyl, aryl (1–3C) alkyl, heteroaryl (1–3C) alkyl, and aryl; or $R^2$ represents the above-defined group B or (1–3C) alkyl having group B as a substituent group; or (1–3C) alkyl having the following defined cyclic group G as a substituent group. Here, group G represents cyclic group G selected from the group consisting of pyridyloxy, 2-oxo-1,2- dihydropyridine-1-yl, pyrimidyloxy, pyrazyloxy, pyridazyloxy, piperazine-1-yl optionally having a lower alkyl group or an aryl (1–7C) alkyl group at the 4-position, pyrrolidine-1-yl, piperidine-1-yl, 4-morpholine-4-yl, and pyrrole-1-yl;

$R^3$ is hydrogen; or $R^3$ is (i) $D(CH_2)_{0-3}CO$, (ii) DCOECO or (iii) $DSO_2ECO$ as an acyl group; or $D(CH_2)_{0-3} SO_2$ and $DCOESO_2$ as a sulfonyl group (wherein group D represents hydrogen, a C1–6 straight-chain, branched or cyclic alkyl group, trifluoromethyl, 2,2,2-trifluoroethoxy, 2,2,2-trifluoroethylamino, $COOR_a$, $CONR_bR_c$, $NR_bR_c$, or group G defined above); or $R^3$ is thiourea represented by $R_bR_cNCS$; or group E independently represents a divalent benzene nucleus, a divalent heteroaryl nucleus, 1,4-piperazine-di-yl, a divalent cyclohexyl group, and a divalent 1,4-cyclohexadienyl group); or $R^3$ is $R_a$ ;

X represents an unsubstituted carbon atom and Y represents a nitrogen atom; and z represents —$CH_2$— wherein the 2 hydrogen atoms may independently be replaced by $R_a$ and $R_b$.

6. Novel acetamide compounds according to claim 1 or 2 or pharmacologically acceptable salts thereof, wherein $R^0$, $R^1$, $R^2$, $R^3$, X, Y and Z in formula (I) represent the following:

$R^0$ is an unsubstituted phenyl group or a substituted phenyl group with 1 or 2 substituent groups selected from halogen, lower alkyl, hydroxy, lower alkoxy, and lower acyloxy, $R^1$ is an unsubstituted phenyl group, $R^2$ is an unsubstituted phenyl group, unsubstituted (1–8C) alkyl, or a substituted (1–8C) alkyl group having a substituent group selected from carboxyl, a lower acyloxy, phenyl, pyrrolidine-1-yl, pyridyl, pyridyloxy, 2-oxo-1,2-dihydropyridine-1-yl, pyrimidyloxy, pyrazyloxy, pyridazyloxy, or a lower alkyl-substituted piperazine-1-yl or a lower alkyl-substituted piperazine-1-yl-carbonyl, and morpholino, $R^3$ is hydrogen, a lower acyl group, formyl, sulfamoyl, lower alkylsulfonyl, aryl lower alkylsulfonyl, heteroarylsulfonyl, trifluoromethylsulfonyl or tetrahydrofuroyl, X is an unsubstituted carbon atom, Y is a nitrogen atom, and Z is —$CH_2$—.

7. Novel acetamide compounds according to claim 1 or 2 or pharmacologically acceptable salts thereof, wherein $R^0$, $R^1$, $R^2$, $R^3$, X, Y and Z in formula (I) represent the following:

$R^0$ is an unsubstituted phenyl group, $R^1$ is an unsubstituted phenyl group, $R^2$ is an unsubstituted (1–8C) alkyl or a substituted (1–8C) alkyl group having a substituent group selected from pyrrolidine-1-yl, pyridyloxy, 2-oxo-1,2-dihydropyridine-1-yl, pyrimidyloxy, pyrazyloxy, pyridazyloxy, lower alkyl-substituted piperazine-1-yl or a lower alkyl-substituted piperazine-1-yl carbonyl, X is an unsubstituted carbon atom, Y is a nitrogen atom, and Z is —$CH_2$—.

8. Novel acetamide compounds according to claim 1 or 2 or pharmacologically acceptable salts thereof, wherein $R^3$ in formula (I) is a group selected from hydrogen, lower alkylcarbonyl, lower alkoxycarbonyl, acyl, sulfonyl and sulfamoyl.

9. Novel acetamide compounds according to claim 1 or pharmacologically acceptable salts thereof, wherein $R^0$, $R^1$, $R^2$, $R^3$, X, Y and Z in formula (I) represent the following:

$R^0$ is an unsubstituted phenyl group or a lower alkoxy-substituted phenyl group, $R^1$ is an unsubstituted phenyl group, $R^2$ is a lower alkoxy, $R^3$ is hydrogen or a lower alkoxycarbonyl, X is an unsubstituted carbon atom, Y is a nitrogen atom, and Z is —$CH_2$—.

10. Novel acetamide compounds or pharmacologically acceptable salts thereof, wherein $R^0$, $R^1$, $R^2$, $R^3$, X, Y and Z in formula (I) represent the following:

$R^0$ is an unsubstituted phenyl group, $R^1$ is an unsubstituted phenyl group, $R^2$ is 3-(2-oxo-1,2-dihydropyridine-1-yl)propyl, $R^3$ is a group selected from hydrogen, t-butyloxycarbonyl, formyl, acetyl, lower alkylsulfonyl, aryl lower alkylsulfonyl, heteroaryl-sulfonyl, trifluoromethylsulfonyl, lower alkylamino-sulfonyl, aryl lower alkylaminosulfonyl, heteroaryl lower alkylaminosulfonyl, and heteroarylaminosulfonyl, X is an unsubstituted carbon atom, Y is a nitrogen atom, and Z is —$CH_2$—.

11. Novel acetamide compounds or pharmacologically acceptable salts thereof, wherein $R^0$, $R^1$, $R^2$, $R^3$, X, Y and Z in formula (I) represent the following:

$R^0$ is an unsubstituted phenyl group, $R^1$ is an unsubstituted phenyl group, $R^2$ is 3-(2-pyridyloxy)propyl, $R^3$ is a group selected from hydrogen, t-butyloxycarbonyl, formyl, acetyl, lower alkylsulfonyl, aryl lower alkylsulfonyl, heteroarylsulfonyl, trifluoromethylsulfonyl, lower alkylaminosulfonyl, aryl lower alkylaminosulfonyl, heteroaryl lower alkylaminosulfonyl, and heteroarylaminosulfonyl, X is an unsubstituted carbon atom, Y is a nitrogen atom, and Z is —$CH_2$—.

12. 2-(5-Amino-6-oxo-2-phenyl-1,6-dihydropyrimidine-1-yl)-N-{2,3-dioxo-1-(3-fluorophenyl)methyl}butylacetamide or pharmacologically acceptable salts thereof.

13. 2-(5-Amino-6-oxo-2-phenyl-1,6-dihydropyrimidine-1-yl)-N-{2,3-dioxo-6-(4-morpholine-4-yl)-1-phenylmethyl}hexylacetamide or pharmacologically acceptable salts thereof.

14. (A) 2-(5-amino-6-oxo-2-phenyl-1,6-dihydropyrimidine-1-yl)-N-{2,3-dioxo-1-phenylmethyl-6-(2-oxo-1,2-dihydropyridine-1-yl)}hexylacetamide, (B) 2-(5-t-butyloxycarbonylamino-6-oxo-2-phenyl-1,6-dihydro-pyrimidine-1-yl)-N-1-{2,3-dioxo-1-phenylmethyl-6-(2-oxo-1,2-dihydropyridine-1-yl)}hexylacetamide, (C) 2-(5-acetylamino-6-oxo-2-phenyl-1,6-dihydropyrimidine-1-yl)-N-{2,3-dioxo-1-phenylmethyl-6-(2-oxo-1,2-dihydropyridine-1-yl)}hexylacetamide or pharmacologically acceptable salts thereof.

15. (A) 2-(5-Amino-6-oxo-2-phenyl-1,6-dihydro-pyrimidine-1-yl)-N-{2,3-dioxo-6-(2-pyridyloxy)-1-phenylmethyl}hexylacetamide, (B) 2-(5-t-butyloxycarbonylamino-6-oxo-2-phenyl-1,6-dihydro-pyrimidine-1yl)-N-{2,3-dioxo-6-(2-pyridyloxy)-1-phenylmethyl}hexylacetamide, (C) 2-(5-benzylsulfonylamino-6-oxo-2-phenyl-1,6-dihydropyrimidine-1-yl)-N-{2,3-dioxo-6-(2-pyridyloxy)-1-phenylmethyl}hexylacetamide, (D) 2-(5-formylamino-6-oxo-2-phenyl-1,6-dihydropyrimidine-1-yl)-N-{2,3-dioxo-6-(2-pyridyloxy)-1-phenylmethyl) hexylacetamide, (E) 2-(5-benzylaminosulfonylamino-6-oxo-2-phenyl-1,6-dihydropyrimidine-1-yl)-N-(2,3-dioxo-6-(2-pyridyloxy-1-phenylmethyl}hexylacetamide, (F) 2-(5-pyridylmethyloxycarbonylamino-6-oxo-2-phenyl-1,6-dihydropyrimidine-1-yl)-N-{2,3-dioxo-6-(2-pyridyloxy)-1-phenylmethyl}hexylacetamide, (G) 2-(5-acetylamino-6-oxo-2-phenyl-1,6-dihydro-pyrimidine-1-yl)-N-{2,3-dioxo-6-(2-pyridyloxy)-1- phenylmethyl hexylacetamide or pharmacologically acceptable salts thereof.

16. (A) 2-(5-t-Butyloxycarbonylamino-6-oxo-2-phenyl-1,6-dihydropyrimidine-1-yl-N-{2-methoxycarbonyl-1-(4-hydroxyphenyl)methyl-2-oxo}ethylacetamide, (B) 2-(5-t-butyloxycarbonylamino-6-oxo-2-phenyl-1,6-dihydropyrimidine-1-yl)-N-{2-methoxycarbonyl-1-(3-fluoro-4-hydroxyphenyl) methyl-2-oxo}ethylacetamide, (C) 2-(5-amino-6-oxo-2-phenyl-1,6-dihydropyrimidine-1-yl)-N-(2-oxo-2-phenylcarbamoyl-1-phenylmethyl)ethylacetamide, (D) 2-(5-amino-6-oxo-2-phenyl-1,6-dihydropyrimidine-1-yl)-N-(2-benzylcarbamoyl-2-oxo-1-phenylmethyl)ethylacetamide, (E) 2-(5-amino-6-oxo-2-phenyl-1,6-dihydropyrimidine-1-yl)-N-(2-oxo-2-phenylethylcarbamoyl-1-phenylmethyl)ethylacetamide, (F) 2-(5-t-butyloxycarbonylamino-6-oxo-2-phenyl-1,6-dihydropyrimidine-1-yl)-N-{2-methoxycarbonyl-1-(4-methyloxyphenyl)methyl-2-oxo}ethylacetamide, (G) 2-(5-t-butyloxycarbonylamino-6-oxo-2-phenyl-1,6-dihydropyrimidine-1-yl)-N-(2-oxo-2-phenyl ethylcarbamoyl-1-phenylmethyl)ethylacetamide, (H) 2-(5-aminno-6-oxo-2-phenyl-1,6-dihydropyrimidine-1-yl)-N-{2-methoxycarbonyl-1-(4-methyloxy phenyl)methyl-2-oxo}ethylacetamide, or pharmacologically acceptable salts thereof.

17. (A) 2-(5-Amino-6-oxo-2-phenyl-1,6-dihydropyrimidine-1-yl)-N-(2,3-dioxo-1-phenylmethyl) butyl-acetamide, (B) 2-(5-amino-6-oxo-2-phenyl-1,6-dihydropyrimidine-1-yl)-N-(2,3-dioxo-6-phenyl-1-phenylmethyl) hexylacetamide, (C) 2-(5-amino-6-oxo-2-phenyl-1,6-dihydropyrimidine-1-yl)-N-(2,3-dioxo-5-phenyl-1-phenylmethyl) pentylacetamide, (D) 2-(5-amino-6-oxo-2-phenyl-1,6-dihydropyrimidine-1-yl)-N-(2,3-dioxo-1-phenylmethyl)heptylacetamide, (E) 2-(5-amino-6-oxo-2-phenyl-1,6-dihydropyrimidine-1-yl)-N-(2,3-dioxo-3-phenyl-1-phenylmethyl) propylacetamide, (F) 2-(5-amino-6-oxo-2-phenyl-1,6-dihydropyrimidine-1-yl)-N-(6-carboxyl-2,3-dioxo-1-phenylmethyl)hexylacetamide, (G) 2-(5-amino-6-oxo-2-phenyl-1,6-dihydropyrimidine-1-yl)-N-{2,3-dioxo-1-(3-fluoro-4-hydroxyphenyl) methyl)butylacetamide, (H) 2-(5-amino-6-oxo-2-phenyl-1,6-dihydropyrimidine-1-yl)-N-{2,3-dioxo-1-(3-fluorophenyl) methyl}butylacetamide, (I) 2-(5-amino-6-oxo-2-phenyl-1,6-dihydropyrimidine-1-yl)-N-{2,3-dioxo-1-(3-chlorophenyl) methyl}butylacetamide, (J) 2-(5-amino-6-oxo-2-phenyl-1,6-dihydropyrimidine-1-yl)-N-{2,3-dioxo-1-(3-methylphenyl) methyl}butylacetamide, (K) 2-(5-amino-6-oxo-2-phenyl-1,6-dihydropyrimidine-1-yl)-N-{2,3-dioxo-1-(4-fluorophenyl) methyl}butylacetamide, (L) 2-(5-amino-6-oxo-2-phenyl-1,6-dihydropyrimidine-1-yl)-N-{2,3-dioxo-1-(4-chlorophenyl) methyl}butylacetamide, (M) 2-(5-amino-6-oxo-2-phenyl-1,6-dihydropyrimidine-1-yl)-N-{2,3-dioxo-6-ethoxycarbonyl-1-(3-fluorophenyl)methyl}hexylacetamide, (N) 2-(5-amino-6-oxo-2-phenyl-1,6-dihydro-pyrimidine-1-yl)-N-{1-(3-fluorophenyl)methyl-7-(4-methyl-piperazine-1-yl)-2,3,7-trioxo}heptylacetamide, (O) 2-(5-amino-6-oxo-2-phenyl-1,6-dihydropyrimidine-1-yl)-N-{2,3-dioxo-6-(4-morpholine-4-yl)1-phenylmethyl}hexylacetamide, (P) 2-(5-amino-6-oxo-2-phenyl-1,6-dihydropyrimidine-1-yl)-N-{2,3-dioxo-6-(2-oxo-1,2-dihydropyridine-1-yl)-1-phenyl-methyl}hexylacetamide, (Q) 2-(5-amino-6-oxo-2-phenyl-1,6-dihydropyrimidine-1-yl)-N-{2,3-dioxo-1-phenylmethyl-6-(2-pyridyloxy)}hexylacetamide, (T) 2-(5-t-butyloxycarbonylamino-6-oxo-2-phenyl-1,6-dihydropyrimidine-1-yl)-N-(2,3-dioxo-1-phenylmethyl)butylacetamide, (U) 2-(5-t-butyloxycarbonyl-amino-6-oxo-2-phenyl-1,6-dihydropyrimidine-1-yl)-N-(2,3-dioxo-1-phenylmethyl)hexylacetamide, (V) 2-(5-t-butyloxycarbonylamino-6-oxo-2-phenyl-1,6-dihydropyrimidine-1-yl)-N-(2,3-dioxo-1-phenylmethyl) heptylacetamide, (W) 2-{5-(3-tetrahydrofuroylamino)-6-oxo-2-phenyl-1,6-dihydropyrimidine-1-yl}-N-(2,3-dioxo-6-phenyl-1-phenylmethyl) hexylacetamide, (X) 2-(5-amino-6-oxo-2-phenyl-1,6-dihydro-pyrimidine-1-yl)-N-{2,3-dioxo-1-(2-fluorophenyl) methyl}butylacetamide, or pharmacologically acceptable salts thereof.

18. 2-(5-Formylamino-6-oxo-2-phenyl-1,6-dihyropyrimidine-1-yl)-N-{2,3-dioxo-6-(2-pyridyloxy)-1-phenylmethyl}hexylacetamide or pharmacologically acceptable salts thereof.

19. A pharmaceutical composition comprising the novel acetamide compound of claim 1, 2 or 18 or pharmacologically acceptable salt thereof as an active ingredient.

20. A process for producing the novel acetamide compounds of claim 1 or 2 or pharmacologically acceptable salts thereof, which comprises the following step (A):

(A) in synthesis of the novel acetamide compounds of formula (I), the step of oxidizing the alcohol of formula (II):

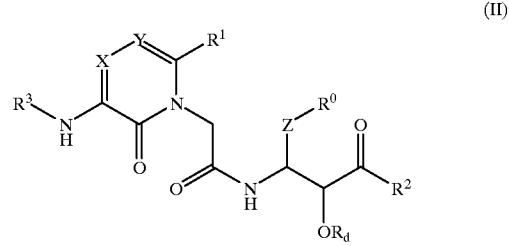

(II)

after removal of a protective group of the alcohol if present, to convert it into the novel acetamide compound of formula (I):

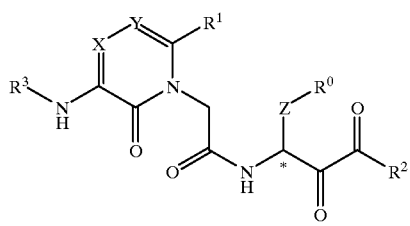
(I)
wherein $R^0$, $R^1$, $R^2$, X, Y and Z have the same meanings as defined in claim 1, and $R_d$ is a hydrogen or a protective group for a hydroxyl group.
21. Compounds of formula (II)
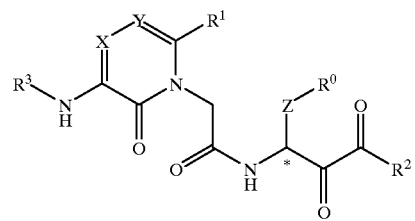
(II)
and salts thereof, wherein $R^0$, $R^1$, $R^2$, $R^3$, X, Y and Z are the groups defined in claim 1, $R_d$ is a hydrogen or a protective group for a hydroxyl group.
* * * * *